US007214780B2

(12) United States Patent
Cunningham et al.

(10) Patent No.: US 7,214,780 B2
(45) Date of Patent: May 8, 2007

(54) PROBES, COMPOSITIONS AND KITS FOR DETERMINING THE PRESENCE OF *MYCOPLASMA PNEUOMONIAE* IN A TEST SAMPLE

(75) Inventors: Melissa M. Cunningham, Gresham, OR (US); James P. Light, II, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 345 days.

(21) Appl. No.: 10/286,653

(22) Filed: Oct. 31, 2002

(65) Prior Publication Data

US 2003/0194723 A1  Oct. 16, 2003

Related U.S. Application Data

(60) Provisional application No. 60/335,015, filed on Nov. 2, 2001.

(51) Int. Cl.
*C07H 21/04* (2006.01)
*C12Q 1/68* (2006.01)

(52) U.S. Cl. ............... 536/23.1; 536/24.3; 536/24.32; 536/25.32; 435/6; 435/91.1; 435/91.2

(58) Field of Classification Search ............ None
See application file for complete search history.

(56) References Cited

U.S. PATENT DOCUMENTS

| 5,369,005 | A | | 11/1994 | Baseman et al. |
|---|---|---|---|---|
| 5,491,062 | A | | 2/1996 | Mckenzie et al. |
| 5,541,308 | A | * | 7/1996 | Hogan et al. ............ 536/23.1 |
| 5,552,279 | A | * | 9/1996 | Weisburg et al. ............ 435/6 |
| 5,656,427 | A | | 8/1997 | Hammond et al. |
| 5,677,123 | A | | 10/1997 | Montagnier et al. |
| 5,691,149 | A | | 11/1997 | Hogan et al. |
| 5,693,467 | A | | 12/1997 | Roblin, III et al. |
| 5,817,463 | A | | 10/1998 | Mullen et al. |
| 5,969,122 | A | * | 10/1999 | Hammond et al. ........ 536/23.1 |
| 6,110,681 | A | | 8/2000 | Ovyn et al. |

FOREIGN PATENT DOCUMENTS

WO    WO 88/03957 A1    6/1988

OTHER PUBLICATIONS

NCBI Blast 2 Sequences results for *M. genitalium* and *M. pneumoniae* (Genbank GI 175479 and GI 459531).*
Kong et al., "Rapid-Cycle PCR for Detection and Typing of *Mycoplasma pneumoniae* in Clinical Specimens", Journal of Clinical Microbiology, Nov. 2000, 38(11):4256-4259.
Yoshida et al., "Phylogeny-Based Rapid Identification of Mycoplasmas and Ureaplasmas from Urethritis Patients", Journal of Clinical Microbiology, Jan. 2002, 40(1):105-110.

* cited by examiner

*Primary Examiner*—Jeanine A. Goldberg
(74) *Attorney, Agent, or Firm*—Charles B. Cappellari

(57) ABSTRACT

The present invention relates to oligonucleotides useful for determining the presence of *Mycoplasma pneumoniae* and/or *Mycoplasma genitalium* in a test sample. The oligonucleotides of the present invention may be incorporated into hybridization assay probes, capture probes and amplification primers, and used in various combinations thereof.

20 Claims, 5 Drawing Sheets

SEQUENCE LISTING

<160> NUMBER OF SEQ ID NOS: 42

<210> SEQ ID NO 1
<211> LENGTH: 32
<212> TYPE: DNA
<213> ORGANISM: Artificial Sequence
<220> FEATURE:
<223> OTHER INFORMATION: Synthetic Construct

<400> SEQUENCE: 1
cattggaaac tattaatcta gagtgtggta gg          32

<210> SEQ ID NO 2
<211> LENGTH: 32
<212> TYPE: RNA
<213> ORGANISM: Artificial Sequence
<220> FEATURE:
<223> OTHER INFORMATION: Synthetic Construct

<400> SEQUENCE: 2
cauuggaaac uauuaaucua gaguguggua gg          32

<210> SEQ ID NO 3
<211> LENGTH: 32
<212> TYPE: DNA
<213> ORGANISM: Artificial Sequence
<220> FEATURE:
<223> OTHER INFORMATION: Synthetic Construct

<400> SEQUENCE: 3
cctaccacac tctagattaa tagtttccaa tg          32

<210> SEQ ID NO 4
<211> LENGTH: 32
<212> TYPE: RNA
<213> ORGANISM: Artificial Sequence
<220> FEATURE:

<223> OTHER INFORMATION: Synthetic Construct

<400> SEQUENCE: 4
ccuaccacac ucuagauuaa uaguuuccaa ug                                32

<210> SEQ ID NO 5
<211> LENGTH: 32
<212> TYPE: DNA
<213> ORGANISM: Artificial Sequence
<220> FEATURE:
<223> OTHER INFORMATION: Synthetic Construct

<400> SEQUENCE: 5
cattggaaac tatcagtcta gagtgtggta gg                                32

<210> SEQ ID NO 6
<211> LENGTH: 32
<212> TYPE: RNA
<213> ORGANISM: Artificial Sequence
<220> FEATURE:
<223> OTHER INFORMATION: Synthetic Construct

<400> SEQUENCE: 6
cauuggaaac uaucagucua gaguguggua gg                                32

<210> SEQ ID NO 7
<211> LENGTH: 32
<212> TYPE: DNA
<213> ORGANISM: Artificial Sequence
<220> FEATURE:
<223> OTHER INFORMATION: Synthetic Construct

<400> SEQUENCE: 7
cctaccacac tctagactga tagtttccaa tg                                32

<210> SEQ ID NO 8
<211> LENGTH: 32
<212> TYPE: RNA
<213> ORGANISM: Artificial Sequence
<220> FEATURE:
<223> OTHER INFORMATION: Synthetic Construct

<400> SEQUENCE: 8
ccuaccacac ucuagacuga uaguuuccaa ug                                32

<210> SEQ ID NO 9
<211> LENGTH: 29
<212> TYPE: DNA
<213> ORGANISM: Artificial Sequence
<220> FEATURE:
<223> OTHER INFORMATION: Synthetic Construct

<400> SEQUENCE: 9
ttggaaacta tcagtctaga gtgtggtag                                    29

<210> SEQ ID NO 10
<211> LENGTH: 29
<212> TYPE: RNA
<213> ORGANISM: Artificial Sequence
<220> FEATURE:
<223> OTHER INFORMATION: Synthetic Construct

<400> SEQUENCE: 10
uuggaaacua ucagucuaga guguggua g                                   29

```
<210> SEQ ID NO 11
<211> LENGTH: 29
<212> TYPE: DNA
<213> ORGANISM: Artificial Sequence
<220> FEATURE:
<223> OTHER INFORMATION: Synthetic Construct

<400> SEQUENCE: 11
ctaccacact ctagactgat agtttccaa                                    29

<210> SEQ ID NO 12
<211> LENGTH: 29
<212> TYPE: RNA
<213> ORGANISM: Artificial Sequence
<220> FEATURE:
<223> OTHER INFORMATION: Synthetic Construct

<400> SEQUENCE: 12
cuaccacacu cuagacugau aguuuccaa                                    29

<210> SEQ ID NO 13
<211> LENGTH: 25
<212> TYPE: DNA
<213> ORGANISM: Artificial Sequence
<220> FEATURE:
<223> OTHER INFORMATION: Synthetic Construct

<400> SEQUENCE: 13
ccttgcaggt cctttcaact ttgat                                        25

<210> SEQ ID NO 14
<211> LENGTH: 25
<212> TYPE: RNA
<213> ORGANISM: Artificial Sequence
<220> FEATURE:
<223> OTHER INFORMATION: Synthetic Construct

<400> SEQUENCE: 14
ccuugcaggu ccuucaacu uugau                                         25

<210> SEQ ID NO 15
<211> LENGTH: 25
<212> TYPE: DNA
<213> ORGANISM: Artificial Sequence
<220> FEATURE:
<223> OTHER INFORMATION: Synthetic Construct

<400> SEQUENCE: 15
atcaaagttg aaaggacctg caagg                                        25

<210> SEQ ID NO 16
<211> LENGTH: 25
<212> TYPE: RNA
<213> ORGANISM: Artificial Sequence
<220> FEATURE:
<223> OTHER INFORMATION: Synthetic Construct

<400> SEQUENCE: 16
aucaaaguug aaaggaccug caagg                                        25

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct
```

<400> SEQUENCE: 17
caaactctag ccattacctg c         21

<210> SEQ ID NO 18
<211> LENGTH: 21
<212> TYPE: RNA
<213> ORGANISM: Artificial Sequence
<220> FEATURE:
<223> OTHER INFORMATION: Synthetic Construct

<400> SEQUENCE: 18
caaacucuag ccauuaccug c         21

<210> SEQ ID NO 19
<211> LENGTH: 21
<212> TYPE: DNA
<213> ORGANISM: Artificial Sequence
<220> FEATURE:
<223> OTHER INFORMATION: Synthetic Construct

<400> SEQUENCE: 19
gcaggtaatg gctagagttt g         21

<210> SEQ ID NO 20
<211> LENGTH: 21
<212> TYPE: RNA
<213> ORGANISM: Artificial Sequence
<220> FEATURE:
<223> OTHER INFORMATION: Synthetic Construct

<400> SEQUENCE: 20
gcagguaaug gcuagaguuu g         21

<210> SEQ ID NO 21
<211> LENGTH: 21
<212> TYPE: DNA
<213> ORGANISM: Artificial Sequence
<220> FEATURE:
<223> OTHER INFORMATION: Synthetic Construct

<400> SEQUENCE: 21
cagctgctta acagttgtat g         21

<210> SEQ ID NO 22
<211> LENGTH: 21
<212> TYPE: RNA
<213> ORGANISM: Artificial Sequence
<220> FEATURE:
<223> OTHER INFORMATION: Synthetic Construct

<400> SEQUENCE: 22
cagcugcuua acaguuguau g         21

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct

<400> SEQUENCE: 23
catacaactg ttaagcagct g         21

<210> SEQ ID NO 24
<211> LENGTH: 21

```
<212> TYPE: RNA
<213> ORGANISM: Artificial Sequence
<220> FEATURE:
<223> OTHER INFORMATION: Synthetic Construct

<400> SEQUENCE: 24
cauacaacug uuaagcagcu g                                            21

<210> SEQ ID NO 25
<211> LENGTH: 32
<212> TYPE: DNA
<213> ORGANISM: Artificial Sequence
<220> FEATURE:
<223> OTHER INFORMATION: Synthetic Construct

<400> SEQUENCE: 25
ggattgaaaa gtctggtgtt aaaggcagct gc                                32

<210> SEQ ID NO 26
<211> LENGTH: 32
<212> TYPE: RNA
<213> ORGANISM: Artificial Sequence
<220> FEATURE:
<223> OTHER INFORMATION: Synthetic Construct

<400> SEQUENCE: 26
ggauugaaaa gucuggiguu aaaggcagcu gc                                32

<210> SEQ ID NO 27
<211> LENGTH: 32
<212> TYPE: DNA
<213> ORGANISM: Artificial Sequence
<220> FEATURE:
<223> OTHER INFORMATION: Synthetic Construct

<400> SEQUENCE: 27
gcagctgcct ttaacaccag acttttcaat cc                                32

<210> SEQ ID NO 28
<211> LENGTH: 32
<212> TYPE: RNA
<213> ORGANISM: Artificial Sequence
<220> FEATURE:
<223> OTHER INFORMATION: Synthetic Construct

<400> SEQUENCE: 28
gcagcugccu uuaacaccag acuuuucaau cc                                32

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
caccgctcca catgaaattc                                              20

<210> SEQ ID NO 30
<211> LENGTH: 20
<212> TYPE: RNA
<213> ORGANISM: Artificial Sequence
<220> FEATURE:
<223> OTHER INFORMATION: Synthetic Construct

<400> SEQUENCE: 30
```
caccgcucca caugaaauuc                                                    20

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct

<400> SEQUENCE: 31
gaatttcatg tggagcggtg                                                    20

<210> SEQ ID NO 32
<211> LENGTH: 20
<212> TYPE: RNA
<213> ORGANISM: Artificial Sequence
<220> FEATURE:
<223> OTHER INFORMATION: Synthetic Construct

<400> SEQUENCE: 32
gaauuucaug uggagcggug                                                    20

<210> SEQ ID NO 33
<211> LENGTH: 21
<212> TYPE: DNA
<213> ORGANISM: Artificial Sequence
<220> FEATURE:
<223> OTHER INFORMATION: Synthetic Construct

<400> SEQUENCE: 33
ctacgcattt caccgctcca c                                                  21

<210> SEQ ID NO 34
<211> LENGTH: 21
<212> TYPE: RNA
<213> ORGANISM: Artificial Sequence
<220> FEATURE:
<223> OTHER INFORMATION: Synthetic Construct

<400> SEQUENCE: 34
cuacgcauuu caccgcucca c                                                  21

<210> SEQ ID NO 35
<211> LENGTH: 21
<212> TYPE: DNA
<213> ORGANISM: Artificial Sequence
<220> FEATURE:
<223> OTHER INFORMATION: Synthetic Construct

<400> SEQUENCE: 35
gtggagcggt gaaatgcgta g                                                  21

<210> SEQ ID NO 36
<211> LENGTH: 21
<212> TYPE: RNA
<213> ORGANISM: Artificial Sequence
<220> FEATURE:
<223> OTHER INFORMATION: Synthetic Construct

<400> SEQUENCE: 36
guggagcggu gaaaugcgua g                                                  21

<210> SEQ ID NO 37
<211> LENGTH: 30
<212> TYPE: DNA
<213> ORGANISM: Artificial Sequence

```
<220> FEATURE:
<223> OTHER INFORMATION: Synthetic Construct

<400> SEQUENCE: 37
cgccactggt gttccttcat atatctacgc                                30

<210> SEQ ID NO 38
<211> LENGTH: 30
<212> TYPE: RNA
<213> ORGANISM: Artificial Sequence
<220> FEATURE:
<223> OTHER INFORMATION: Synthetic Construct

<400> SEQUENCE: 38
cgccacuggu guuccuucau auaucuacgc                                30

<210> SEQ ID NO 39
<211> LENGTH: 30
<212> TYPE: DNA
<213> ORGANISM: Artificial Sequence
<220> FEATURE:
<223> OTHER INFORMATION: Synthetic Construct

<400> SEQUENCE: 39
gcgtagatat atgaaggaac accagtggcg                                30

<210> SEQ ID NO 40
<211> LENGTH: 30
<212> TYPE: RNA
<213> ORGANISM: Artificial Sequence
<220> FEATURE:
<223> OTHER INFORMATION: Synthetic Construct

<400> SEQUENCE: 40
gcguagauau augaaggaac accaguggcg                                30

<210> SEQ ID NO 41
<211> LENGTH: 27
<212> TYPE: DNA
<213> ORGANISM: Artificial Sequence
<220> FEATURE:
<223> OTHER INFORMATION: Synthetic Construct

<400> SEQUENCE: 41
aatttaatac gactcactat agggaga                                   27

<210> SEQ ID NO 42
<211> LENGTH: 28
<212> TYPE: DNA
<213> ORGANISM: Artificial Sequence
<220> FEATURE:
<223> OTHER INFORMATION: Synthetic Construct

<400> SEQUENCE: 42
gcattggaaa ctattaatct agagtgtg                                  28
```

PROBES, COMPOSITIONS AND KITS FOR DETERMINING THE PRESENCE OF *MYCOPLASMA PNEUOMONIAE* IN A TEST SAMPLE

This application claims the benefit of U.S. Provisional Application No. 60/335,015, filed Nov. 2, 2001, the contents of which are hereby incorporated by reference herein.

FIELD OF THE INVENTION

The present invention relates to hybridization assay probes, capture probes, amplification primers, nucleic acid compositions, methods and kits useful for determining the presence of *Mycoplasma pneumoniae* and/or *Mycoplasma genitalium* in a test sample.

INCORPORATION BY REFERENCE

All references referred to herein are hereby incorporated by reference in their entirety. The incorporation of these references, standing alone, should not be construed as an assertion or admission by the inventors that any portion of the contents of all of these references, or any particular reference, is considered to be essential material for satisfying any national or regional statutory disclosure requirement for patent applications. Notwithstanding, the inventors reserve the right to rely upon any of such references, where appropriate, for providing material deemed essential to the claimed invention by an examining authority or court. No reference referred to herein is admitted to be prior art to the claimed invention.

BACKGROUND OF THE INVENTION

*Mycoplasmas* are small prokaryotic organisms (0.2 to 0.3 µm) belonging to the class Mollicutes, whose members lack a cell wall and have a small genome size. The mollicutes include at least 100 species of *Mycoplasma*, 13 of which are known to infect humans. One of these species, *M. pneumoniae*, is a major cause of community-acquired pneumonia (non-pneumococcal bacterial pneumonia), a type of pneumonia which is responsible for up to 2 million respiratory tract infections in the United States annually. The incidence of *mycoplasma* non-pneumonic respiratory infection has been estimated to be 10 to 20 times higher than this number. See 2 GERALD L. MANDELL ET AL., PRINCIPLES AND PRACTICE OF INFECTIOUS DISEASES § D (5th ed. 2000); see also PATRICK R. MURRAY ET AL., MANUAL OF CLINICAL MICROBIOLOGY § V (6th ed. 1995).

While *M. pneumoniae* infections are generally mild, as many as 10% of those infected with the organism progress to bronchopneumonia, requiring treatment or hospitalization. The most common early presentation of an *M. pneumoniae* infection is tracheobronchitis. Radiological findings vary widely and often indicate a more severe condition than symptoms typically associated with an *M. pneumoniae* infection (e.g., flu-like dry cough, pharyngitis, fever, malaise, headache and nasal congestion) would suggest Recovery of the organism from extra-pulmonary sites is rare, although hematologic, musculoskeletal, cardiovascular, dermatologic and neurologic complications have been reported. See ELMER W. KONEMAN, COLOR ATLAS AND TEXTBOOK OF DIAGNOSTIC MICROBIOLOGY 862 (5th ed. 1997).

*M. pneumoniae* infections occur year round, especially in large populations, but typically peak in late fall or winter. The incidence of isolation of the organism increases with age, and it is second only to *Streplococcus pneumoniae* as a cause of pneumonia in the elderly. *M. pneumoniae*-related pneumonia is seen most commonly in children over 5 years of age and in young adults. Crowded military populations, camps and schools are particularly at risk for community-acquired pneumonia caused by *M. pneumoniae* infections. In one study, over 5% of pneumonias seen in young military recruits were associated with *M. pneumoniae*. See Gray et al., "Respiratory diseases among U.S. military personnel: countering emerging threats," *Emerg. Infect. Dis.*, 3:379–387 (1999).

The incubation period for *M. pneumoniae*, which typically ranges from 2 to 3 weeks, is significantly longer than most viral respiratory infections. After clinical manifestation, symptoms associated with a *M. pneumonia* infection generally last from 3 to 10 days. Appropriate antibiotic treatments can significantly shorten the duration of the respiratory symptoms associated with a *M. pneumoniae* infection. However, since culture and many available diagnostic tests are difficult, time consuming and/or not readily available, ineffective antibiotic treatments are often prescribed, thereby unnecessarily prolonging the symptomatic period.

Diagnosis of a *M. pneumoniae* infection is often based solely on clinical signs and symptoms. Although culture remains the gold standard for diagnosing a *M. pneumoniae* infection, isolation, detection and identification of the fastidious *M. pneumoniae* organisms is difficult and can take weeks to complete. Diagnosis has also been based on demonstrating the presence of cold agglutinins. However, this test is a nonspecific indicator, as cold agglutinins may never develop in some patients infected with *M. pneumoniae* and have also been observed with lymphoma and a variety of viral diseases, including mononucleosis caused by Epstein-Barr virus and cytomegalovirus. Assaying for complement-fixing antibodies has also been used to confirm infection with *M. pneumoniae*, but is of little practical value in guiding diagnostic and therapeutic decisions, as the antibodies arise too late in the infection. An enzyme immunoassay has also been developed for detecting IgM and IgG directed against *M. pneumoniae*, but is limited in its usefulness since it does not become positive until 1 to 2 weeks into infection. In addition, an antigen-capture, indirect immunoassay has been used to detect *M. pneumoniae* antigens in sputum samples; however, the reagents of this assay cross-react with *M. genitalium* antigens. See, e.g., Bartlett et al., "Community-Acquired Pneumonia in Adults: Guidelines for Management," *Clin. Infect. Dis.*, 26:811–838 (1998). Thus, a need exists for a sensitive and specific assay which can be used to determine the presence of *M. pneumoniae* in a test sample during a clinically relevant period.

Also of clinical relevance is the detection of *M. genitalium* in a test sample. *M. genitalium*, which is thought to be a cause of nongonococcal urethritis (NGU), a sexually transmitted disease, has been detected to a significantly greater extent in symptomatic males than in asymptomatic males. See Yoshida et al., "Phylogeny-Based Rapid Identification of *Mycoplasma* and *Ureaplasmas* from *Urethritis Patients*," *J. Clin. Microbiol.*, 40:105–110 (2002). In addition to NGU, *M. genitalium* is thought to be involved in pelvic inflammatory disease, which can lead to infertility in women in severe cases. See JACK MANILOFF ET AL., MYCOPLASMAS: MOLECULAR BIOLOGY AND PATHOGENESIS 417 (ASM 1992). *M. genitalium* may also cause disease in the respiratory tract, making it important for some assays to distinguish between the presence of *M. pneumoniae* and *M. gentialium*. See LEE H. HILBORNE ET AL., A REVIEW OF THE SCIENTIFIC LITERATURE AS IT Pertains to the Gulf War Illnesses, Vol.1: Infectious Diseases Ch. 3 (Rand 2000). Therefore, it would be of clinical importance to have an assay for specifically detecting the presence of *M. genitalium* in a test sample which is capable of distinguishing between *M. genitalium* and *M. pneumoniae*.

SUMMARY OF THE INVENTION

The present invention provides a solution to the clinical need for a sensitive assay specific for *M. pneumoniae* by featuring oligonucleotides which are useful for determining whether *M. pneumoniae* is present in a test sample which is obtained from, for example, a throat or nasopharyngeal swab taken from an individual suspected of having community-acquired pneumonia. More rarely, specimens for determining the presence of *M. pneumoniae* may be obtained from joint fluid aspirates, cerebrospinal fluid, synovial fluid, the genital tract, as well as experimental solutions, cultures and other sample media. The present invention also provides a solution to the clinical need for an assay specific for *M. genitalium* by featuring oligonucleotides which are useful for determining whether *M. genitalium* is present in a test sample which is obtained from, for example, the urethra, the anal canal, the lower genital tract of a woman or the respiratory tract The featured oligonucleotides may be contained in hybridization assay probes, helper probes, capture probes and/or amplification primers which are useful for detecting, immobilizing and/or amplifying target nucleic acid sequences derived from *M. pneumoniae* present in a test sample.

In one embodiment of the present invention, hybridization assay probes are provided which hybridize to a target region present in nucleic acid derived from *M. pneumoniae* to form detectable probe:target hybrids indicating the presence of *M. pneumoniae* in a test a sample. The probes of this embodiment comprise an oligonucleotide having a target binding region, where the base sequence of the target binding region consists of or is contained within a base sequence selected from the group consisting of:

SEQ ID NO:1 cattggaaactattaatctagagtgtggtagg,
SEQ ID NO:2 cauuggaaacuauuaaucuagaguguggguagg,
SEQ ID NO:3 cctaccacactctagattaatagttccaatg, and
SEQ ID NO:4 ccuaccacacucuagauuaauaguuuccaaug.

These probes preferentially hybridize to the target nucleic acid over nucleic acid derived from non-*M. pneumoniae* organisms, especially over nucleic acid derived from *M. genitalium*, under stringent hybridization assay conditions.

In another embodiment of the present invention, hybridization assay probes are provided which hybridize to a target region present in nucleic acid derived from *M. genitalium* to form detectable probe:target hybrids indicating the presence of *M. genitalium* in a test a sample. The probes of this embodiment comprise an oligonucleotide having a target binding region, where the base sequence of the target binding region consists of or is contained within a base sequence selected from the group consisting of:

SEQ ID NO:5 cattggaaactatcagtctagagtgtggtagg,
SEQ ID NO:6 cauuggaaacuaucagucuagaguguggguagg,
SEQ ID NO:7 cctaccacactctagactgatagttccaatg,
SEQ ID NO:8 ccuaccacacucuagacugauaguuuccaaug,
SEQ ID NO:9 ttggaaactatcagtctagagtgtggtag,
SEQ ID NO:10 uuggaaacuaucagucuagaguguggguag,
SEQ ID NO:11 ctaccacactctagactgatagtttccaa, and
SEQ ID NO:12 cuaccacacucuagacugauaguuuccaa.

These probes preferentially hybridize to the target nucleic acid over nucleic acid derived from non-*M. genitalium* organisms, especially over nucleic acid derived from *M. pneumoniae*, under stringent hybridization assay conditions.

The base sequence of the target binding region of a probe for *M. pneumoniae* or *M. genitalium* in the present invention preferably includes at least 12 contiguous bases of the recited sequence, more preferably is at least about 80% homologous to the recited sequence, even more preferably is at least about 90% homologous to the recited sequence, and most preferably consists of the recited sequence (excluding internal bulges or a basic regions in the target binding region which do not hybridize to the target sequence or interfere with distinguishing between the target nucleic acid and non-target nucleic acid). In the preferred embodiment, the degree of homology is based upon a contiguous base region present in the recited sequence which is available for hybridization to the target sequence. The target binding region may consist of DNA, RNA, a combination DNA and RNA, or it may be a nucleic acid analog (e.g., a peptide nucleic acid) or contain one or more modified nucleosides (e.g., a ribonucleoside having a 2'-O-methyl substitution to the ribofuranosyl moiety). Most preferably, the hybridization assay probes of the present invention are nucleic acids or nucleic acid analogs consisting of the recited sequence and optionally include a detectable label or reporter group. Probes of the present invention are preferably oligonucleotides up to 35, 50 or 100 bases in length.

Hybridization assay probes of the present invention may include one or more base sequences in addition to the base sequence of the target binding region region which do not stably bind to nucleic acid derived from the target organism (i.e., *M. pneumoniae* or *M. genitalium*) under stringent conditions. An additional base sequence may be comprised of any desired base sequence, so long as it does not stably bind to nucleic acid derived from the target organism under stringent conditions or prevent stable hybridization of the probe to the target nucleic acid. By way of example, an additional base sequence may constitute the immobilized probe binding region of a capture probe, where the immobilized probe binding region is comprised of, for example, a 3' poly dA (adenine) region which hybridizes under stringent conditions to a 5' poly dT (thymine) region of a polynucleotide bound directly or indirectly to a solid support. An additional base sequence might also be a 5' sequence recognized by an RNA polymerase or which enhances initiation or elongation by an RNA polymerase (e.g., a T7 promoter). More than one additional base sequence may be included if the first sequence is incorporated into, for example, a "molecular beacon" probe. Molecular beacons are disclosed by Tyagi et al., "Detectably Labeled Dual Conformation Oligonucleotide Probes, Assays and Kits," U.S. Pat. No. 5,925,517, and include a target binding region which is bounded by two base sequences having regions which are at least partially complementary to each other. A more detailed description of molecular beacons is provided infra in the section entitled "Hybridization Assay Probes to *M. pneumoniae* or *M. genitalium* Ribosomal Nucleic Acid." An additional base sequence may be joined directly to the target binding region or, for example, by means of a non-nucleotide linker.

While not required, the probes preferably include a detectable label or group of interacting labels. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably bind to the target nucleic acid under the stated conditions, and mixtures of these. In one particularly preferred embodiment, the label is an acridinium ester (AE), preferably 4-(2-succinimidyloxy-carbonyl ethyl)-phenyl-10-methylacridinium-9-carboxylate fluorosulfonate (hereinafter referred to as "standard AE"). Groups of interacting labels include, but are not limited to, enzyme/substrate, enzyme/cofactor, luminescent/quencher, luminescent/adduct, dye dimers and Förrester energy transfer pairs.

In another embodiment, the invention contemplates probe mixes that are useful for determining whether *M. pneumoniae* organisms are present in a test sample. For instance, to determine the presence of these organisms, the probe mix may comprise one of the above-described *M. pneumoniae* probes and one or more helper probes. Preferably, the helper probes are oligonucleotides up to 100 bases in length, more preferably from 12 to 50 bases in length, and even more preferably from 18 to 35 bases in length.

The invention also contemplates compositions comprising stable nucleic acid duplexes formed between the above-described hybridization assay probes and the target nucleic acids for the probes under stringent hybridization assay conditions.

In a further embodiment, the present invention provides capture probes comprising at least one oligonucleotide containing an immobilized probe binding region and a target binding region. The immobilized probe binding region of the capture probes may be comprised of any base sequence capable of stably hybridizing under stringent conditions to oligonucleotides bound to a solid support present in a test sample. Preferably, the immobilized probe binding region is a poly dA, homopolymer tail located at the 3' end of the capture probe. In this embodiment, oligonucleotides bound to the solid support would include 5' poly dT tails of sufficient length to stably bind to the poly dA tails of the capture probes under assay conditions. In a preferred embodiment, the immobilized probe binding region includes a poly dA tail which is about 30 adenines in length, and the capture probe includes a spacer region which is about 3 thymines in length for joining target binding region and the immobilized probe binding region to each other.

The target binding region of the capture probes stably binds to a target sequence present in nucleic acid derived from *Mycoplasma* organisms. The target binding region of the capture probes of this embodiment comprise a base sequence region which is at least about 85% homologous (preferably at least about 90% homologous, more preferably at least about 95% homologous, and most preferably 100% homologous) to a base sequence selected from the group consisting of:
SEQ ID NO:13 ccttgcaggtcctttcaactttgat,
SEQ ID NO:14 ccuugcagguccuuucaacuuugau,
SEQ ID NO:15 atcaaagttgaaaggacctgcaagg,
SEQ ID NO:16 aucaaaguugaaaggaccugcaagg,
SEQ ID NO:17 caaactctagccattacctgc,
SEQ ID NO:18 caaacucuagccauuaccugc,
SEQ ID NO:19 gcaggtaatggctagagtttg, and
SEQ ID NO:20 gcagguaauggcuagaguuug.

The invention also features amplification primers useful for detecting the presence of *Mycoplasma* organisms in an amplification assay. In one preferred embodiment, the invention provides one or more amplification primers for amplifying (e.g., which, when contacted with a nucleic acid polymerase under amplification conditions, will bind to or cause extension through a nucleic acid region) nucleic acid derived from a *Mycoplasma* organism present in a test sample, each amplification primer comprising an oligonucleotide, where the base sequence of the target binding region has or substantially corresponds to a base sequence selected from the group consisting of:
SEQ ID NO:21 cagctgcttaacagttgtatg,
SEQ ID NO:22 cagcugcuuaacaguuguaug,
SEQ ID NO:23 catacaactgttaagcagctg,
SEQ ID NO:24 cauacaacuguuaagcagcug,
SEQ ID NO:25 ggattgaaaagtctggtgttaaaggcagctgc,
SEQ ID NO:26 ggauugaaaagucugguguuaaaggcagcugc,
SEQ ID NO:27 gcagctgcctttaacaccagactttcaatcc,
SEQ ID NO:28 gcagcugccuuuaacaccagacuuuucaaucc,
SEQ ID NO:29 caccgctccacatgaaattc,
SEQ ID NO:30 caccgcuccacaugaaauuc,
SEQ ID NO:31 gaatttcatgtggagcggtg,
SEQ ID NO:32 gaauuucauguggagcggug,
SEQ ID NO:33 ctacgcatttcaccgctccac,
SEQ ID NO:34 cuacgcauuucaccgcuccac,
SEQ ID NO:35 gtggagcggtgaaatgcgtag,
SEQ ID NO:36 guggagcggugaaaugcguag,
SEQ ID NO:37 cgccactggtgttccttcatatatctacgc,
SEQ ID NO:38 cgccacugguguuccuucauauaucuacgc,
SEQ ID NO:39 gcgtagatatatgaaggaacaccagtggcg, and
SEQ ID NO:40 gcguagauauaugaaggaacaccaguggcg.

Amplification primers of the present invention do not, however, include an amplification primer comprising an oligonucleotide having a target binding region, where the base sequence of the target binding region has or substantially corresponds to the base sequence of SEQ ID NO:25, SEQ ID NO:26, SEQ ID NO:27, SEQ ID NO:28, SEQ ID NO:37, SEQ ID NO:38, SEQ ID NO:39 or SEQ ID NO:40, except in combination with an amplification primer comprising an oligonucleotide having a target binding region, where the base sequence of the target binding region has or substantially corresponds to the base sequence of SEQ ID NO:21, SEQ ID NO:22, SEQ ID NO:23, SEQ ID NO:24, SEQ ID NO:29, SEQ ID NO:30, SEQ ID NO:31, SEQ ID NO:32, SEQ ID NO:33, SEQ ID NO:34, SEQ ID NO:35 or SEQ ID NO:36. The amplification primers of the present invention have a target binding region which is preferably from 18 to 40 bases in length. The amplification primers of this embodiment optionally include a 5' sequence which is recognized by an RNA polymerase or which enhances initiation or elongation by an RNA polymerase. If included, a T7 promoter, such as SEQ ID NO:41 aatttaatacgactcactatagggaga, is preferred.

When the amplification primers of the present invention are not combined in sets of two or more amplification primers, the amplification primers preferably comprise an oligonucleotide having a target binding region, where the base sequence of the target binding region is at least about 80% homologous (more preferably at least about 90% homologous and most preferably 100% homologous) to the base sequence of SEQ ID NO:21, SEQ ID NO:22, SEQ ID NO:23, SEQ ID NO:24, SEQ ID NO:29, SEQ ID NO:30, SEQ ID NO:31, SEQ ID NO:32, SEQ ID NO:33, SEQ ID NO:34, SEQ ID NO:35 or SEQ ID NO:36. And, with the exception of an optional 5' sequence recognized by an RNA polymerase or which enhances initiation or elongation by an RNA polymerase, the base sequences of the amplification primers are preferably at least about 80% homologous (more preferably at least about 90% homologous and most preferably 100% homologous) to the base sequence of SEQ ID NO:21, SEQ ID NO:22, SEQ ID NO:23, SEQ ID NO:24, SEQ ID NO:29, SEQ ID NO:30, SEQ ID NO:31, SEQ ID NO:32, SEQ ID NO:33, SEQ ID NO:34, SEQ ID NO:35 or SEQ ID NO:36.

Amplification primers of the present invention are preferably employed in sets of at least two amplification primers. Preferred sets include a first amplification primer comprising an oligonucleotide having a target binding region, where the base sequence of the target binding region contains an at least 10 contiguous base region which is at least about 80% complementary (more preferably at least about 90% complementary and most preferably 100% complementary) to an at least 10 contiguous base region present in a target sequence selected from the group consisting of SEQ ID NO:21, SEQ ID NO:22, SEQ ID NO:23, SEQ ID NO:24, SEQ ID NO:25, SEQ ID NO:26, SEQ ID NO:27 and SEQ ID NO:28. The second amplification primer of these preferred sets comprises an oligonucleotide having a target binding region, where the base sequence of the target binding region contains an at least 10 contiguous base region which is at least about 80% complementary (more preferably at least about 90% complementary and most preferably 100% complementary) to an at least 10 contiguous base region present in a target sequence selected from the group consisting of SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39 and SEQ ID NO:40. In particularly preferred embodiments, the base sequence of the target binding region of an amplification primer is at least about 80% complementary, more preferably at least about 90% complementary and most preferably perfectly complementary to the target sequence. And, except for an optional 5' sequence recognized by an RNA polymerase or which enhances initiation or elongation by an RNA polymerase, the base sequence of an amplification primer in the most preferred embodiment of the present invention is at least about 80% homologous (more preferably at least about 90% homologous and most preferably 100% homologous) to the base sequence of SEQ ID NO:21, SEQ ID NO:22, SEQ ID NO:23, SEQ ID NO:24, SEQ ID NO:29, SEQ ID NO:30, SEQ ID NO:31, SEQ ID NO:32, SEQ ID NO:33, SEQ ID NO:34, SEQ ID NO:35 or SEQ ID NO:36.

The invention additionally contemplates compositions comprising stable nucleic acid duplexes formed between the above-described amplification primers and the target nucleic acids for the primers under amplification conditions.

The invention further features methods for determining whether *M. pneumoniae* or, in the alternative, *M. genitalium* is present in a test sample. In one embodiment, the invention provides a method for determining whether *M. pneumoniae* or *M. genitalium* is present in a test sample, where the method comprises the steps of: (a) contacting the test sample with one of the above-described hybridization assay probes for detecting *M. pneumoniae* or *M. genitalium* under conditions permitting the probe to preferentially hybridize to a target nucleic acid derived from *M. pneumoniae* or *M. genitalium*, thereby forming a probe:target hybrid stable for detection; and (b) determining whether the hybrid is present in the test sample as an indication of the presence or absence of *M. pneumoniae* or *M. genitalium* in the test sample. This method may further include the step of quantifying the amount of hybrid present in the test sample as a means for estimating the amount of *M. pneumoniae* or *M. genitalium* present in the test sample.

The methods for determining whether *M. pneumoniae* or *M. genitalium* is present in a test sample, or the amount of these organisms present in a test sample, may further include the step of contacting the test sample with at least one helper probe, as desired. See Hogan et al., "Means and Method for Enhancing Nucleic Acid Hybridization," U.S. Pat. No. 5,030,557. In addition to the helper probes, or in the alternative, the methods may further include the step of contacting the test sample with at least one of the above-described amplification primers appropriate for amplifying a target nucleic acid sequence present in nucleic acid derived from *Mycoplasma* organisms, as desired.

The invention also contemplates methods for amplifying a target nucleic acid sequence present in nucleic acid derived from *Mycoplasma* organisms present in a test sample, where the method comprises the steps of: (a) contacting the test sample with at least one of the above-described amplification primers under amplification conditions; and (b) amplifying the target nucleic acid sequence. Preferred amplification methods will include a set of at least two of the above-described amplification primers.

In one embodiment, the method for amplifying a target nucleic acid sequence present in nucleic acid derived from *Mycoplasma* organisms will further include the steps of: (a) contacting the test sample with a hybridization assay probe which preferentially hybridizes to the target nucleic acid sequence, or a complement thereof, under stringent hybridization conditions, thereby forming a probe:target hybrid stable for detection; and (b) determining whether the hybrid is present in the test sample as an indication of the presence or absence of *M. pneumoniae* or *M. genitalium* in the test sample. The above-described hybridization assay probes are especially preferred for this method.

The invention also contemplates kits for determining whether *M. pneumoniae* or *M. genitalium* is present in a test sample. These kits comprise at least one of the above-described hybridization assay probes specific for nucleic acid derived from *M. pneumoniae* or *M. genitalium* and optionally include written instructions for determining the presence or amount of *M. pneumoniae* or *M. genitalium* in a test sample. In another embodiment, the kits further comprise at least one helper probe appropriate for nucleic acid derived from *M. pneumoniae* and/or *M. genitalium*. In a further embodiment, the kits comprise, in addition to the hybridization assay probes, at least one of the above-described amplification primers appropriate for amplifying a target nucleic acid sequence present in nucleic acid derived from *Mycoplasma* organisms. In still another embodiment, the kits further comprise, in addition to the hybridization assay probes, at least one of the above-described capture probes. In yet another embodiment, the kits further comprise, in addition to the hybridization assay probes, at least one of the above-described capture probes and at least one of the above-described amplification primers. Kits including a capture probe may further include a solid support material (e.g., magnetically responsive particles) for immobilizing the capture probe, either directly or indirectly, in a test sample.

The invention also contemplates kits for amplifying a target nucleic acid sequence present in nucleic acid derived from *Mycoplasma* organisms, where the kits comprise at least one of the above-described amplification primers and optionally include written instructions for amplifying nucleic acid derived from *Mycoplasma* organisms. In a further embodiment, these kits may include, in addition to the amplification primers, at least one of the above-described capture probes. Such kits may further include a solid support material for immobilizing the capture probe in a test sample.

Those skilled in the art will appreciate that the hybridization assay probes of the present invention may be used as amplification primers, helper probes or capture probes; that the target binding regions of the amplification primers of the present invention may be used as hybridization assay probes, helper probes or capture probes, depending upon the degree of specificity required by a particular assay; and that the target binding regions of the capture probes of the present invention may be used as hybridization assay probes, amplification primers or helper probes, depending upon the degree of specificity required by a particular assay. Thus, the present invention contemplates oligonucleotides for use in determining the presence or absence of *M. pneumoniae* or *M. genitalium* in a test sample comprising, consisting essentially of or consisting of any of the above-described nucleotide base sequences and analogs thereof.

Unless indicated otherwise, the phrases "comprising" may be substituted with the phrase "consisting essentially of" or "consisting of" in the following disclosure, thereby indicating varying degrees of scope contemplated by the present invention. Each claim, however, is intended to be limited by the particular transitional phrase recited.

Other features and advantages of the invention will be apparent from the following description of the preferred embodiments thereof and from the claims.

DESCRIPTION OF THE PREFERRED EMBODIMENTS

Figure 1:
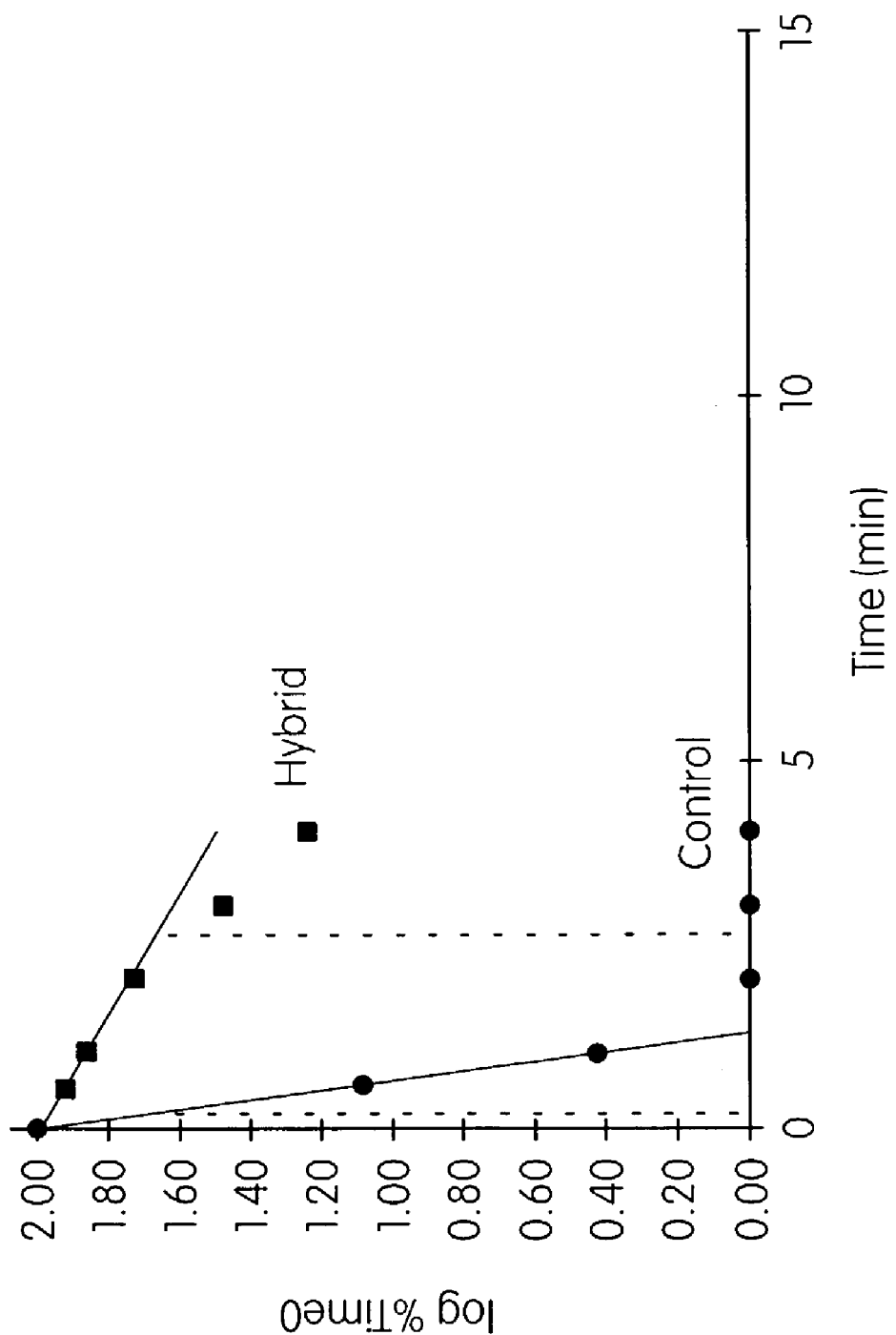
FIGS. 1 and 2 are graphs which were used to determine the differential hydrolysis ratios of two *M. pneumoniae* probes disclosed by Hammond et al., "Nucleic Acid Hybridization Assay Probes, Helper Probes and Amplification Oligonucleotides Targeted to *M. pneumoniae* Nucleic Acid," U.S. Pat. No. 5,656,427. Using the time and signal data set forth in Tables 2–5 of Example 2 infra, these graphs plot the data for hybrids (■) and controls (●) as the log of the percentage of time zero chemiluminescence on the y-axis versus time in minutes on the x-axis. Slopes and associated $t_{1/2}$ values (time required to hydrolyze 50% of the probe associated acridinium ester label) were determined for the controls and hybrids of each probe using standard linear-regression analysis. See Arnold et al., "Assay Formats Involving Acridinium-Ester-Labeled DNA Probes," *Clinical Chemistry*, 35:1588–1594 (1989). Based on the $t_{1/2}$ values determined from these graphs, the differential hydrolysis ratio for each probe was calculated by comparing the $t_{1/2}$ value of the hybrid to the $t_{1/2}$ value of the control.

The present invention describes oligonucleotides targeted to nucleic acid derived from *Mycoplasma* organisms which are useful for determining the presence or absence of *M. pneumoniae* or *M. genitalium* in a test sample. The oligonucleotides can aid in detecting *M. pneumoniae* or *M. genitalium* in different ways, such as by functioning as hybridization assay probes, capture probes and/or amplification primers. Hybridization assay probes of the present invention can preferentially hybridize to a target nucleic acid sequence present in nucleic acid derived from *M. pneumoniae* or *M. genitalium* under stringent hybridization assay conditions to form detectable duplexes which indicate the presence of *M. pneumoniae* or *M. genitalium* in a test sample. Some of the probes are believed to be capable of distinguishing between the target organism and its known closest phylogenetic neighbors. Capture probes of the present invention can hybridize to a target nucleic acid sequence present in nucleic acid derived from *Mycoplasma* organisms under stringent hybridization assay conditions and can be used to separate target nucleic acid from clinical specimens. Amplification primers of the present invention can hybridize to a target nucleic acid sequence present in nucleic acid derived from *Mycoplasma* organisms under amplification conditions and can be used as primers in an amplification reaction to generate M.-derived nucleic acid. The probes and amplification primers may be used in assays for the detection and/or quantitation of *M. pneumoniae* or *M. genitalium* in a test sample.

A. Definitions

The following terms have the indicated meanings in the specification unless expressly indicated to have a different meaning.

By "sample" or "test sample" is meant any substance suspected of containing a target organism or nucleic acid derived from the target organism. The substance may be, for example, an unprocessed clinical specimen, such as a sputum or urethral specimen, a buffered medium containing the specimen, a medium containing the specimen and lytic agents for releasing nucleic acid belonging to the target organism, or a medium containing nucleic acid derived from the target organism which has been isolated and/or purified in a reaction receptacle or on a reaction material or device. In the claims, the terms "sample" and "test sample" may refer to specimen in its raw form or to any stage of processing to release, isolate and purify nucleic acid derived from target organisms in the specimen. Thus, within a method of use claim, each reference to a "sample" or "test sample" may refer to a substance suspected of containing nucleic acid derived from the target organism or organisms at different stages of processing and is not limited to the initial form of the substance in the claim.

By "target nucleic acid" or "target" is meant a nucleic acid containing a target nucleic acid sequence.

By "target nucleic acid sequence," "target nucleotide sequence," "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto. (The claims, however, may restrict a target sequence to the particular sense of the recited sequence with a proviso excluding complementary sequences thereof.)

By "polynucleotide," "oligonucleotide" or "oligomer" is meant a polymer made up of two or more nucleoside subunits or nucleobase subunits coupled together. The oligonucleotide may be DNA and/or RNA and analogs thereof. The sugar groups of the nucleoside subunits may be ribose, deoxyribose and analogs thereof, including, for example, ribonucleosides having a 2'-O-alkyl substitution (e.g., 2'-O-methyl) to the ribofuranosyl moiety. (Oligonucleotides including nucleoside subunits having 2' substitutions which are useful as hybridization assay probes, capture probes, helper probes and/or amplification primers are disclosed by Becker et al., "Method for Amplifying Target Nucleic Acids Using Modified Primers," U.S. Pat. No. 6,130,038.) The nucleoside subunits may by joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseuodo peptide backbone, such as a 2-aminoethylglycine backbone which couples the nucleobase subunits by means of a carboxymethyl linker to the central secondary amine. (DNA analogs having a pseudo peptide backbone are referred to as "peptide nucleic acids" or "PNA" and are disclosed by Nielsen et al., "Peptide Nucleic Acids," U.S. Pat. No. 5,539,082.) Other non-limiting examples of oligonucleotides or oligomers contemplated by the present invention include nucleic acid analogs containing bicyclic and tricyclic nucleoside and nucleotide analogs referred to as "locked nucleic acids," "locked nucleoside analogues" or "LNA." (Locked nucleic acids are disclosed by Wang, "Conformationally Locked Nucleosides and Oligonucleotides," U.S. Pat. No. 6,083,482; Imanishi et al., "Bicyclonucleoside and Oligonucleotide Analogues," U.S. Pat. No. 6,268,490; and Wengel et al., "Oligonucleotide Analogues," International Publication No. WO 99/14226.) Any nucleic acid analog is contemplated by the present invention provided the oligonucleotide, as defined above, can stably bind to a target nucleic acid under stringent hybridization assay conditions or amplification conditions. For hybridization assay probes, an oligonucleotide must be capable of preferentially hybridizing to the target nucleic acid under stringent hybridization assay conditions. For capture probes, an oligonucleotide or set of joined oligonucleotides must be capable of hybridizing to an immobilized probe and to the target nucleic acid under the same or different assay conditions (hybridization to the target sequence is preferably preferential). And for amplification primers, an oligonucleotide must be capable of hybridizing to the target nucleic acid under amplification conditions and acting as a primer and/or a promoter template for the initiation of nucleic acid synthesis.

Oligonucleotides of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. As intended by this disclosure, an oligonucleotide does not consist of wild-type chromosomal DNA or the in vivo transcription products thereof. One use of an oligonucleotide is as a hybridization assay probe. Oligonucleotides may also be used as in vivo or in vitro therapeutic amplification primers or as antisense agents to block or inhibit gene transcription, or translation in diseased, infected, or pathogenic cells.

By "hybridization assay probe" or "probe" is meant an oligonucleotide having a base sequence sufficiently complementary to its target nucleic acid sequence to form a probe:target hybrid stable for detection under stringent hybridization assay conditions. As would be understood by someone having ordinary skill in the art, a probe is an isolated nucleic acid molecule, or an analog thereof, in a form not found in nature without human intervention (e.g., recombined with foreign nucleic acid, isolated, or purified to some extent). The probes of this invention may have additional nucleosides or nucleobases which are coupled to the target complementary sequence so long as such nucleosides or nucleobases do not prevent hybridization under stringent hybridization conditions and, in the case of hybridization assay probes, do not prevent preferential hybridization to the target nucleic acid. One or more sequences which are non-complementary to the target sequence may be included in a probe of the present invention, provided these additional sequences do not stably bind to nucleic acid derived from any organism present in the test sample. Such sequences could include, by way of example, a target capture sequence (generally a homopolymer tract, such as a poly dA, poly A, poly dT or poly U tail), a promotor sequence, a binding site for RNA transcription, a restriction endonuclease recognition site, or sequences which will confer a desired secondary or tertiary structure, such as a catalytic active site or a hairpin structure, which can be used to facilitate detection and/or amplification. Probes of a defined sequence may be produced by techniques known to those of ordinary skill in the art, such as by chemical synthesis, and by in vitro or in vivo expression from recombinant nucleic acid molecules.

By "stably," "stable" or "stable for detection" is meant that the temperature of a reaction mixture is at least 2° C. below the melting temperature of a nucleic acid duplex. The temperature of the reaction mixture is more preferably at least 5° C. below the melting temperature of the nucleic acid duplex, and even more preferably at least 10° C. below the melting temperature of the reaction mixture.

By "substantially homologous," "substantially corresponding" or "substantially corresponds" is meant that the subject oligonucleotide has a base sequence containing an at least 10 contiguous base region that is at least about 80% homologous, preferably at least about 90% homologous, and most preferably 100% homologous to an at least 10 contiguous base region present in a reference base sequence (excluding RNA and DNA equivalents). (Those skilled in the art will readily appreciate modifications that could be made to the hybridization assay conditions at various percentages of homology to permit hybridization of the oligonucleotide to the target sequence while preventing levels of non-specific hybridization sufficient to interfere with detection of the target nucleic acid.) The degree of similarity is determined by comparing the order of nucleobases making up the two sequences and does not take into consideration other structural differences which may exist between the two sequences, provided the structural differences do not prevent hydrogen bonding with complementary bases. The degree of homology between two sequences can also be expressed in terms of the number of base differences between each set of at least 10 contiguous bases being compared, which may be 0, 1 or 2 base differences.

By "substantially complementary" is meant that the subject oligonucleotide has a base sequence containing an at least 10 contiguous base region that is at least 80% complementary, preferably at least 90% complementary, and most preferably 100% complementary to an at least 10 contiguous base region present in a target nucleic acid sequence (excluding RNA and DNA equivalents). (Those skilled in the art will readily appreciate modifications that could be made to the hybridization assay conditions at various percentages of complementarity to permit hybridization of the oligonucleotide to the target sequence while preventing levels of non-specific hybridization sufficient to interfere with detection of the target nucleic acid.) The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may be 0, 1 or 2 base mismatches.

By "about" is meant the nearest rounded whole number when referring to a percentage of complementarity or homology (e.g., a lower limit of 24.4 bases would be 24 bases and a lower limit of 24.5 bases would be 25 bases).

By "RNA and DNA equivalents" is meant RNA and DNA molecules having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "hybridization" is meant the ability of two completely or partially complementary nucleic acid strands to come together under specified hybridization assay conditions in an antiparallel orientation (a parallel orientation may also be possible) to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases that are not members of these "canonical" pairs. Non-canonical base pairing is well-known in the art. See, e.g., ROGER L. P. ADAMS ET AL., THE BIOCHEMISTRY OF THE NUCLEIC ACIDS ($11^{th}$ ed. 1992).

By "preferentially hybridize" is meant that under stringent hybridization assay conditions, hybridization assay probes can hybridize to their target nucleic acids to form stable probe:target hybrids indicating the presence of at least one organism of interest ("detectable hybrids"), and there is not formed a sufficient number of stable probe:non-target hybrids to indicate the presence of non-targeted organisms ("non-detectable hybrids"), especially phylogenetically closely related organisms. Thus, the probe hybridizes to target nucleic acid to a sufficiently greater extent than to non-target nucleic acid to enable one having ordinary skill in the art to accurately detect the presence (or absence) of nucleic acid derived from M. pneumoniae or M. genitalium, as appropriate, and distinguish its presence from that of a phylogenetically closely related organism in a test sample. In general, reducing the degree of complementarity between an oligonucleotide sequence and its target sequence will decrease the degree or rate of hybridization of the oligonucleotide to its target region. However, the inclusion of one or more non-complementary bases may facilitate the ability of an oligonucleotide to discriminate against non-target organisms.

Preferential hybridization can be measured using any of a variety of techniques known in the art, including, but not limited to those based on light emission, mass changes, changes in conductivity or turbidity. A number of detection means are described herein, and one in particular is used in the examples provided below. Preferably, there is at least a 10-fold difference between target and non-target hybridization signals in a test sample, more preferably at least a 100-fold difference, and most preferably at least a 500-fold difference. Preferably, non-target hybridization signals in a test sample are no more than the background signal level.

By "stringent hybridization assay conditions," "hybridization assay conditions," "stringent hybridization conditions," or "stringent conditions" is meant conditions permitting a hybridization assay probe to preferentially hybridize to a targetnucleic acid (preferably rRNA or rDNA derived from M. pneumoniae or M. genitalium) over nucleic acid derived from a closely related non-target microorganism. Stringent hybridization assay conditions may vary depending upon factors including the GC content and length of the probe, the degree of similarity between the probe sequence and sequences of non-target sequences which may be present in the test sample, and the target sequence. Hybridization conditions include the temperature and the composition of the hybridization reagents or solutions. While the Examples section infra provides preferred hybridization assay conditions for detecting target nucleic acids derived from M. pneumoniae or M. genitalium using the probes of the present invention, other stringent conditions could be easily ascertained by someone having ordinary skill in the art.

By "assay conditions" is meant conditions permitting stable hybridization of an oligonucleotide to a target nucleic acid. Assay conditions do not require preferential hybridization of the oligonucleotide to the target nucleic acid.

By "differential hydrolysis" is meant the different rates at which the ester bond of an acridinium ester (AE) molecule is hydrolyzed in the presence of an alkaline selection reagent, which will depend upon whether the AE molecule is associated with a probe free in solution or a probe bound to a target nucleic acid. Generally, AE molecules associated with probe bound to target nucleic acid will hydrolyze more slowing than AE molecules associated with probe free in solution in the presence of a selection reagent. An example of an alkaline selection reagent is set forth in the Examples section infra under the subheading "Reagents."

By "differential hydrolysis ratio" is meant the ratio of the rate of hydrolysis of the ester bond of an AE molecule associated with probe bound to a target nucleic acid to the rate of hydrolysis of the ester bond of an AE molecule associated with an identical probe free in solution in the presence of an alkaline selection reagent. The greater the differential hydrolysis ratio of the AE-labeled probe, the greater the sensitivity and discriminatory capacity of the AE-labeled probe for the target nucleic acid.

By "consists essentially of" or "consisting essentially of," when used with reference to a hybridization assay probe herein, is meant an oligonucleotide comprising a target binding region, where the base sequence of the target binding region consists of or is contained within at least 29 contiguous bases of the base sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. The base sequence of the target binding region preferably contains the base sequence of SEQ ID NO:9, SEQ ID NO:10, SEQ ID NO:11 or SEQ ID NO:12 for detecting the presence of M. genitalium in a test sample or the corresponding base sequence within the base sequence of SEQ ID NO:1, SEQ ID NO:2, SEQ ID NO:3 or SEQ ID NO:4 for detecting the presence of *M. pneumoniae* in a test sample. Thus, these phrases contain both a sequence length limitation and a sequence variation limitation. Any additions or deletions are non-material variations of the specified base sequence which do not prevent the oligonucleotide from having its claimed property (i.e., preferentially hybridizing under stringent hybridization assay conditions to the target nucleic acid over non-target nucleic acids). The oligonucleotide may include other nucleic acid molecules which do not participate in hybridization of the probe to the target nucleic acid and which do not affect such hybridization.

By "nucleic acid duplex," "duplex," "nucleic acid hybrid" or "hybrid" is meant a stable nucleic acid structure comprising a double-stranded, hydrogen-bonded region. Such hybrids include RNA:RNA, RNA:DNA and DNA:DNA duplex molecules and analogs thereof. The structure is sufficiently stable to be detectable by any known means, including means which do not require a probe associated label. For instance, the detection method may include a probe coated substrate which is optically active and sensitive to changes in mass at its surface. Mass changes result in different reflective and transmissive properties of the optically active substrate in response to light and serve to indicate the presence or amount of immobilized target nucleic acid. See, e.g., Nygren et al., "Devices and Methods for Optical Detection of Nucleic Acid Hybridization," U.S. Pat. No. 6,060,237.

By "amplification primer" or "primer" is meant an oligonucleotide capable of hybridizing to a target nucleic acid and acting as a primer and/or a promoter template (e.g., for synthesis of a complementary strand, thereby forming a functional promoter sequence) for the initiation of nucleic acid synthesis. If the amplification primer is designed to initiate RNA synthesis, the primer may contain a base sequence which is non-complementary to the target sequence but which is recognized by an RNA polymerase, such as a T7, T3 or SP6 RNA polymerase. An amplification primer may contain a 3' terminus which is modified to prevent or lessen the rate or amount of primer extension. (McDonough et al. disclose primers and promoter-primers having modified or blocked 3'-ends in U.S. Pat. No. 5,766,849, entitled "Methods of Amplifying Nucleic Acids Using Promoter-Containing Primer Sequences.") While the amplification primers of the present invention may be chemically synthesized or derived from a vector, they are not naturally-occurring nucleic acid molecules.

By "nucleic acid amplification," "target amplification" or "amplification" is meant increasing the number of nucleic acid molecules having at least one target nucleic acid sequence. Target amplification according to the present invention may be either linear or exponential, although exponential amplification is preferred.

By "amplification conditions" is meant conditions permitting nucleic acid amplification. While the Examples section infra provides preferred amplification conditions for amplifying target nucleic acid sequences derived from *Mycoplasma* organisms using primers of the present invention in a transcription-mediated amplification method, other acceptable amplification conditions could be easily determined by one having ordinary skill in the art, depending on the particular method of amplification desired.

By "antisense," "opposite sense" or "negative sense" is meant a nucleic acid molecule perfectly complementary to a reference, or sense, nucleic acid molecule.

By "sense," "same-sense" or "positive sense" is meant a nucleic acid molecule perfectly homologous to a reference nucleic acid molecule.

By "amplicon" is meant a nucleic acid molecule generated in a nucleic acid amplification reaction and which is derived from a target nucleic acid. An amplicon contains a target nucleic acid sequence which may be of the same or opposite sense as the target nucleic acid.

By "derived" is meant that the referred to nucleic acid is obtained directly from a target organism or indirectly as the product of a nucleic acid amplification, which product may be, for instance, an antisense RNA molecule which does not exist in the target organism.

By "capture probe" is meant an oligonucleotide or a set of at least two oligonucleotides linked together which are capable of hybridizing to a target nucleic acid and to an immobilized probe, thereby providing means for immobilizing and isolating the target nucleic acid in a test sample. That portion of the capture probe which hybridizes to the target nucleic acid is referred to as the "target binding region," and that portion of the capture probe which hybridizes to the immobilized probe is referred to as the "immobilized probe binding region." While the preferred capture probe hybridizes to both the target nucleic acid and the immobilized probe under assay conditions, the target binding region and the immobilized probe binding region may be designed to hybridize to their respective target sequences under different hybridization conditions. In this way, the capture probe may be designed so that it first hybridizes to the target nucleic acid under more favorable in solution kinetics before adjusting the conditions to permit hybridization of the immobilized probe binding region to the immobilized probe. When the target binding and immobilized probe binding regions are provided on the same capture probe, they may be directly adjoining each other on the same oligonucleotide, they may be separated from each other by one or more optionally modified nucleotides, or they may be joined to each other by means of a non-nucleotide linker.

By "target binding region" is meant that portion of an oligonucleotide which stably binds to a target sequence present in a target nucleic acid, a DNA or RNA equivalent of the target sequence or a complement of the target sequence under assay conditions. The assay conditions may be stringent hybridization conditions or amplification conditions.

By "immobilized probe binding region" is meant that portion of an oligonucleotide which hybridizes to an immobilized probe under assay conditions.

By "homopolymer tail" in the claims is meant a contiguous base sequence of at least 10 identical bases (e.g., 10 contiguous adenines or thymines).

By "immobilized probe" is meant an oligonucleotide for joining a capture probe to an immobilized support. The immobilized probe is joined either directly or indirectly to the solid support by a linkage or interaction which remains stable under the conditions employed to hybridize the capture probe to the target nucleic acid and to the immobilized probe, whether those conditions are the same or different. The immobilized probe facilitates separation of the bound target nucleic acid from unbound materials in a sample.

By "isolate" or "isolating" is meant that at least a portion of the target nucleic acid present in a test sample is concentrated within a reaction receptacle or on a reaction device or solid carrier (e.g., test tube, cuvette, microtiter plate well, nitrocellulose filter, slide or pipette tip) in a fixed or releasable manner so that the target nucleic acid can be purified without significant loss of the target nucleic acid from the receptacle, device or carrier.

By "separate," "separation," "separating" or "purify," "purified" or "purifying" is meant that one or more components of a sample contained in or on a receptacle, device or carrier are physically removed from one or more other sample components present in or on the receptacle, device or carrier. Sample components which may be removed during a separating or purifying step include proteins, carbohydrates, lipids, inhibitors, non-target nucleic acids and unbound probe. Preferably retained in a sample during a separating or purifying step are target nucleic acids bound to immobilized capture probes.

By "helper probe" is meant an oligonucleotide designed to hybridize to a target nucleic acid at a different locus than that of a hybridization assay probe, thereby either increasing the rate of hybridization of the probe to the target nucleic acid, increasing the melting temperature of the probe:target hybrid, or both.

By "*Mycoplasma* organisms" is meant two or more species of Mycoplasma, including *M. pneumoniae* and *M. genitalium*.

By "phylogenetically closely related" is meant that the organisms are closely related to each other in an evolutionary sense and therefore would have a higher total nucleic acid sequence homology than organisms that are more distantly related. Organisms occupying adjacent and next to adjacent positions on the phylogenetic tree are closely related. Organisms occupying positions farther away than adjacent or next to adjacent positions on the phylogenetic tree will still be closely related if they have significant total nucleic acid sequence homology.

By "species-specific" is meant that the referred to hybridization assay probe is capable of preferentially hybridizing under stringent hybridization assay conditions to a target nucleic acid sequence present in nucleic acid derived from organisms belonging to the species *M. pneumoniae* or *M. genitalium*.

B. Hybridization Conditions and Probe Design

Hybridization reaction conditions, most importantly the temperature of hybridization and the concentration of salt in the hybridization solution, can be selected to allow the hybridization assay probes of the present invention to preferentially hybridize to nucleic acids having a target nucleic sequence derived from either *M. pneumoniae* or *M. genitalium*, and not to non-target nucleic acid which may be present in a test sample. At decreased salt concentrations and/or increased temperatures (conditions of increased stringency) the extent of nucleic acid hybridization decreases as hydrogen bonding between paired nucleotide bases in the double-stranded hybrid molecule is disrupted. This process is known as "melting."

Generally speaking, the most stable hybrids are those having the largest number of contiguous, perfectly matched (i.e., hydrogen-bonded) nucleotide base pairs. Such hybrids would usually be expected to be the last to melt as the stringency of the hybridization conditions increases. However, a double-stranded nucleic acid region containing one or more mismatched, "non-canonical," or imperfect base pairs (resulting in weaker or non-existent base pairing at that position in the nucleotide sequence of a nucleic acid) may still be sufficiently stable under conditions of relatively high stringency to allow the nucleic acid hybrid to be formed and detected in a hybridization assay without cross-reacting with other, non-selected nucleic acids which may be present in a test sample.

Hence, depending on the degree of similarity between the nucleotide sequences of the target nucleic acid and those of non-target nucleic acids belonging to phylogenetically distinct, but closely-related organisms on the one hand, and the degree of complementarity between the nucleotide sequences of a particular probe and those of the target and non-target nucleic acids on the other, one or more mismatches will not necessarily defeat the ability of an oligonucleotide contained in the probe or primer to hybridize to the target nucleic acid and not to non-target nucleic acids.

The hybridization assay probes of the present invention were chosen, selected, and/or designed to maximize the difference between the melting temperatures ($T_m$) of the probe:target hybrid ($T_m$ is defined as the temperature at which half of the potentially double-stranded molecules in a given reaction mixture are in a single-stranded, denatured state) and the $T_m$ of a mismatched hybrid formed between the probe and rRNA or rDNA of the phylogenetically most closely-related organisms expected to be present in the test sample, but not sought to be detected. While the unlabeled amplification primers and capture probes need not have such an extremely high degree of specificity as the hybridization assay probe to be useful in the present invention, they are designed in a similar manner to preferentially hybridize to one or more target nucleic acids over other nucleic acids under specified amplification or hybridization assay conditions.

To facilitate the identification of nucleic acid sequences to be used in the design of probes, 16S rRNA nucleotide sequences from different organisms were first aligned to maximize homology. These organisms included *Acholeplasma laidlawii, Escherichia coli, Mycoplasma buccale, Mycoplasma bovis, Mycoplasma capricolum, Mycoplasma faucium, Mycoplasma fermentans, Mycoplasma gallisepticum, Mycoplasma genitalium, Mycoplasma hominis, Mycoplasma iowae, Mycoplasma lipophilum, Mycoplasma muris, Mycoplasma orale, Mycoplasma pneumoniae, Mycoplasma pirum, Mycoplasma primatum, Mycoplasma salivarium, Spiroplasma mirum* and *Ureaplasma urealyticum*. The sequences used for this comparison were determined in the laboratory or obtained from published sources. Sequences for *M. pneumoniae* and *M. genitalium* were obtained from the GenBank database under Accession Nos. M29061 and X77334, respectively.

Within the rRNA molecule there is a close relationship between secondary structure (caused in part by intra-molecular hydrogen bonding) and function. This fact imposes restrictions on evolutionary changes in the primary nucleotide sequence causing the secondary structure to be maintained. For example, if a base is changed in one "strand" of a double helix (due to intra-molecular hydrogen bonding, both "strands" are part of the same rRNA molecule), a compensating substitution usually occurs in the primary sequence of the other "strand" in order to preserve complementarity (this is referred to as co-variance), and thus the necessary secondary structure. This allows two very different rRNA sequences to be aligned based both on the conserved primary sequence and also on the conserved secondary structure elements. Potential target sequences for the hybridization assay probes described herein were identified by noting variations in the homology of the aligned sequences.

The sequence evolution at each of the variable regions is mostly divergent. As a result of this divergence, corresponding rRNA variable regions of more distant phylogenetic relatives of *M. pneumoniae* and *M. genitalium* show greater differences from the rRNA of these organisms than do the rRNAs of phylogenetically closer relatives. Sufficient variation between *M. pneumoniae* and *M. genitalium* and other organisms was observed to identify preferred target sites and design hybridization assay probes useful for distinguishing between *M. pneumoniae* and *M. genitalium* over other closely related organisms.

Merely identifying putatively unique potential target nucleotide sequences does not guarantee that a functionally species-specific hybridization assay probe may be made to hybridize to *M. pneumoniae* or *M. genitalium* rRNA or rDNA comprising that sequence. Various other factors will determine the suitability of a nucleic acid locus as a target site for species-specific probes. Because the extent and specificity of hybridization reactions, such as those described herein, are affected by a number of factors, manipulation of one or more of those factors will determine the exact sensitivity and specificity of a particular oligonucleotide, whether perfectly complementary to its target or not. The importance and effect of various assay conditions are known to those skilled in the art and are disclosed by the following: Kohne, "Method for Detection, Identification and Quantitation of Non-Viral Organisms," U.S. Pat. No. 4,851, 330; Hogan et al., "Nucleic Acid Probes to *Mycobacterium gordonae*," U.S. Pat. No. 5,216,143; and Hogan, "Nucleic Acid Probes for Detection and/or Quantitation of Non-Viral Organisms," U.S. Pat. Nos. 5,840,488.

The desired temperature of hybridization and the hybridization solution composition (such as salt concentration, detergents and other solutes) can also greatly affect the stability of double-stranded hybrids. Conditions such as ionic strength and the temperature at which a probe will be allowed to hybridize to a target must be taken into account in constructing a species-specific probe. The thermal stability of hybrid nucleic acids generally increases with the ionic strength of the reaction mixture. On the other hand, chemical reagents which disrupt hydrogen bonds, such as formamide, urea, dimethyl sulfoxide and alcohols, can greatly reduce the thermal stability of the hybrids.

To maximize the specificity of a probe for its target, probes of the present invention were designed to hybridize to their targets under conditions of high stringency. Under such conditions only single nucleic acid strands (or regions) having a high degree of complementarity will hybridize to each other. Single nucleic acid strands without such a high degree of complementarity will not form hybrids. Accordingly, the stringency of the assay conditions determines the amount of complementarity which should exist between two nucleic acid strands in order to form a hybrid. Stringency is chosen to maximize the difference in stability between the hybrid formed between the probe and the target nucleic acid and potential hybrids between the probe and any non-target nucleic acids present in a test sample.

Proper specificity may be achieved by minimizing the length of the hybridization assay probe having perfect complementarity to sequences of non-target organisms, by avoiding G and C rich regions of complementarity to non-target nucleic acids, and by constructing the probe to contain as many destabilizing mismatches to non-target sequences as possible. Whether a probe is appropriate for detecting only a specific type of organism depends largely on the thermal stability difference between probe:target hybrids versus probe:non-target hybrids. In designing probes, the differences in these $T_m$ values should be as large as possible (preferably 2–5° C. or more). Manipulation of the $T_m$ can be accomplished by changes to probe length and probe composition, such as GC content versus AT content or the inclusion of nucleotide analogs (e.g., ribonucleotides having a 2'-O-methyl substitution to the ribofuranosyl moiety).

In general, the optimal hybridization temperature for oligonucleotide probes is approximately 5° C. below the melting temperature for a given duplex. Incubation at temperatures below the optimum temperature may allow mismatched base sequences to hybridize and can therefore decrease specificity. The longer the probe, the more hydrogen bonding between base pairs and, in general, the higher the $T_m$. Increasing the percentage of G and C also increases the $T_m$ because G-C base pairs exhibit additional hydrogen bonding and therefore greater thermal stability than A-T base pairs. Such considerations are known in the art. See, e.g., J. SAMBROOK ET AL., MOLECULAR CLONING: A LABORATORY MANUAL CH. 11 (2d ed. 1989).

A preferred method for determining $T_m$ measures hybridization using the well known hybridization protection assay (HPA) disclosed by Arnold et al., "Homogenous Protection Assay," U.S. Pat. No. 5,283,174. The $T_m$ can be measured using HPA in the following manner. Probe molecules are labeled with an acridinium ester and permitted to form probe:target hybrids in a lithium succinate buffer (0.1 M lithium succinate buffer, pH 4.7, 20 mM EDTA, 15 mM aldrithiol-2, 1.2 M LiCl, 3% (v/v) ethanol absolute, 2% (w/v) lithium lauryl sulfate) using an excess amount of target. Aliquots of the solution containing the probe:target hybrids are then diluted in the lithium succinate buffered solution and incubated for five minutes at various temperatures starting below that of the anticipated $T_m$ (typically 55° C.) and increasing in 2–5° C. increments. This solution is then diluted with a mild alkaline borate buffer (600 mM boric acid, 240 mM NaOH, 1% (v/v) TRITON® X-100, pH 8.5) and incubated at an equal or lower temperature (for example 50° C.) for ten minutes.

Under these conditions the acridinium ester attached to the single-stranded probe is hydrolyzed, while the acridinium ester attached to hybridized probe is relatively protected from hydrolysis. Thus, the amount of acridinium ester remaining after hydrolysis treatment is proportional to the number of hybrid molecules. The remaining acridinium ester can be measured by monitoring the chemiluminescence produced from the remaining acridinium ester by adding hydrogen peroxide and alkali to the solution. Chemiluminescence can be measured in a luminometer, such as a LEADER® 450i luminometer (Gen-Probe Incorporated, San Diego, Calif.; Cat. No. 3200i). The resulting data is plotted as percent of maximum signal (usually from the lowest temperature) versus temperature. The $T_m$ is defined as the temperature at which 50% of the maximum signal remains. In addition to the method above, $T_m$ may be determined by isotopic methods known to those skilled in the art (see, e.g., U.S. Pat. No. 5,840,488).

It should be noted that the $T_m$ for a given hybrid varies depending on the nature of the hybridization solution used. Factors such as the salt concentration, detergents, and other solutes can affect hybrid stability during thermal denaturation (see, e.g., SAMBROOK ET AL., supra, ch. 11). Conditions such as ionic strength and the temperature at which a probe will be allowed to hybridize to target should be taken into account in probe construction. (The thermal stability of a hybrid nucleic acid increases with the ionic strength of the reaction mixture.) On the other hand, chemical reagents that disrupt hydrogen bonds, such as formamide, urea, dimethyl sulfoxide and alcohols, can greatly reduce hybrid thermal stability.

To ensure specificity of a hybridization assay probe for its target, it is preferable to design probes which hybridize only to target nucleic acid under conditions of high stringency. Only highly complementary sequences will form hybrids under conditions of high stringency. Accordingly, the stringency of the assay conditions determines the amount of complementarity needed between two sequences in order for a stable hybrid to form. Stringency should be chosen to maximize the difference in stability between the probe:target hybrid and potential probe:non-target hybrids.

Examples of specific stringent hybridization conditions are provided in the Examples section infra (see the subsection entitled "Reagents" for a description of particular hybridization and amplification reagents which can be used). Of course, alternative stringent hybridization conditions could be determined by those of ordinary skill in the art based on the present disclosure. (See, e.g., SAMBROOK ET AL., supra, ch. 11.)

The length of the target nucleic acid sequence region and, accordingly, the length of the probe sequence can also be important. In some cases, there may be several sequences from a particular region, varying in location and length, which may be used to design probes with the desired hybridization characteristics. In other cases, one probe may be significantly better with regard to specificity than another which differs from it merely by a single base. While it is possible for nucleic acids that are not perfectly complementary to hybridize, the longest stretch of perfectly complementary bases, as well as the base compositions, will generally determine hybrid stability.

Regions of rRNA known to form strong internal structures inhibitory to hybridization are less preferred target regions, especially in assays where helper probes disclosed infra are not used. Likewise, probes with extensive self-complementarity are generally to be avoided. (It needs to be pointed out, however, that some degree of self-complementarity in a probe may be desirable, as in hairpin probes like the molecular beacons and molecular torches discussed below.) If a strand is wholly or partially involved in an intra-molecular or inter-molecular hybrid, it will be less able to participate in the formation of a new inter-molecular probe: target hybrid without a change in the reaction conditions. Ribosomal RNA molecules are known to form very stable intra-molecular helices and secondary structures by hydrogen bonding. By designing a probe to a region of the target nucleic acid which remains substantially single-stranded under hybridization conditions, the rate and extent of hybridization between probe and target may be increased.

A genomic ribosomal nucleic acid (rDNA) target occurs naturally in a double-stranded form, as does a product of the polymerase chain reaction (PCR). These double-stranded targets are naturally inhibitory to hybridization with a probe and require denaturation prior to hybridization. Appropriate denaturation and hybridization conditions are known in the art (see, e.g., Southern, E. M., *J. Mol. Biol.,* 98:503 (1975)).

A number of formulae are available which will provide an estimate of the melting temperature for perfectly matched oligonucleotides to their target nucleic acids. One such formula is the following:

$$T_m = 81.5 + 16.6(\log_{10}[Na^+]) + 0.41(\text{fraction G+C}) - (600/N)$$

(where N=the length of the oligonucleotide in number of nucleotides) provides a good estimate of the $T_m$ for oligonucleotides between 14 and 60 to 70 nucleotides in length. From such calculations, subsequent empirical verification or "fine tuning" of the $T_m$ may be made using screening techniques well known in the art. For further information on hybridization and oligonucleotide probes reference, may be made to SAMBROOK ET AL., supra, ch. 11. This reference, among others well known in the art, also provides estimates of the effect of mismatches on the $T_m$ of a hybrid. Thus, from the known nucleotide sequence of a given region of the ribosomal RNA (or rDNA) of two or more organisms, oligonucleotides may be designed which will distinguish these organisms from one another.

C. Preparation of Oligonucleotides

The hybridization assay probes, amplification primers and capture probes of the present invention can be readily prepared by methods known in the art. Preferably, the oligonucleotides are synthesized using solid phase methods. Caruthers, for example, describes using standard phosphoramidite solid-phase chemistry to join nucleotides by phosphodiester linkages. See Caruthers et al., "Chemical Synthesis of Deoxynucleotides by the Phosphoramidite Method," *Methods Enzymol.,* 154:287 (1987). Automated solid-phase chemical synthesis using cyanoethyl phosphoramidite precursors has been describedby Barone. See Barone et al., "In Situ Activation of bis-dialkylaminephosphines—a New Method for Synthesizing Deoxyoligonucleotides on Polymer Supports," *Nucleic Acids Res.,* 12(10):4051 (1984). Batt discloses a procedure for synthesizing oligonucleotides containing phosphorothioate linkages in U.S. Pat. No. 5,449,769, entitled "Method and Reagent for Sulfurization of Organophosphorous Compounds." In addition, Riley et al. disclose the synthesis of oligonucleotides having different linkages including methylphosphonate linkages in U.S. Pat. No. 5,811,538, entitled "Process for the Purification of Oligomers." Moreover, methods for the organic synthesis of oligonucleotides are known to those of skill in the art and are described in, for example, SAMBROOK ET AL., supra, ch. 10.

Following synthesis and purification of a particular oligonucleotide, several different procedures may be utilized to purify and control the quality of the oligonucleotide. Suitable procedures include polyacrylamide gel electrophoresis or high pressure liquid chromatography. Both of these procedures are well known to those skilled in the art.

All of the oligonucleotides of the present invention, whether hybridization assay probes, amplification primers or capture probes, may be modified with chemical groups to enhance their performance or to facilitate the characterization of amplification products. For example, backbone-modified oligonucleotides such as those having phosphorothioate, methylphosphonate, 2'-O-alkyl or peptide groups which render the oligonucleotides resistant to the nucleolytic activity of certain polymerases or to nuclease enzymes may allow the use of such enzymes in an amplification or other reaction. Another example of a modification involves using non-nucleotide linkers incorporated between nucleotides in the nucleic acid chain of a probe or primer, and which do not prevent hybridization of a probe or hybridization and elongation of a primer. See Arnold et al., "Non-Nucleotide Linking Reagents for Nucleotide Probes," U.S. Pat. No. 6,031,091. The oligonucleotides of the present invention may also contain mixtures of the desired modified and natural nucleotides.

The 3' end of an amplification primer may be modified or blocked to prevent or inhibit initiation of DNA synthesis, as disclosed by Kacian et al. in U.S. Pat. No. 5,554,516. The 3' end of the primer can be modified in a variety of ways well known in the art By way of example, appropriate modifications to a primer can include the addition of ribonucleotides, 3' deoxynucleotide residues (e.g., cordycepin), 2',3'-dideoxynucleotide residues, modified nucleotides such as phosphorothioates, and non-nucleotide linkages such as those disclosed by Arnold et al. in U.S. Pat. No. 6,031,091 or alkane-diol modifications (see Wilk et al., "Backbone-Modified Oligonucleotides Containing a Butanediol-1,3 Moiety as a 'Vicarious Segment' for the Deoxyribosyl Moiety—Synthesis and Enzyme Studies," *Nucleic Acids Res.*, 18(8):2065 (1990)), or the modification may simply consist of a region 3' to the priming sequence that is non-complementary to the target nucleic acid sequence. Additionally, a mixture of different 3' blocked primers or of 3' blocked and unblocked primers may increase the efficiency of nucleic acid amplification, as disclosed therein.

The 5' end of primers may be modified to be resistant to the 5'-exonuclease activity present in some nucleic acid polymerases. Such modifications can be carried out by adding a non-nucleotide group to the terminal 5' nucleotide of the primer using techniques such as those disclosed by Arnold et al. in U.S. Pat. No. 6,031,091. To facilitate strand displacement, the 5' end may also be modified to include non-complementary nucleotides as disclosed by Dattagupta et al, "Isothermal Strand Displacement Nucleic Acid Amplification," U.S. Pat. No. 6,087,133.

Once synthesized, a selected oligonucleotide may be labeled by any of several well known methods (see, e.g, SAMBROOK, supra, ch. 10). Useful labels include radioisotopes as well as non-radioactive reporting groups. Isotopic labels include $^{3}H$, $^{35}S$, $^{32}P$, $^{125}I$, $^{57}Co$ and $^{14}C$. Isotopic labels can be introduced into the oligonucleotide by techniques known in the art such as nick translation, end labeling, second strand synthesis, the use of reverse transcription, and by chemical methods. When using radiolabeled probes, hybridization can be detected by autoradiography, scintillation counting or gamma counting. The detection method selected will depend upon the particular radioisotope used for labeling. Non-isotopicmaterials can also be used for labeling and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups, as disclosed by Arnold et al. in U.S. Pat. No. 6,031,091. Non-isotopic labels include fluorescent molecules (individual labels or combinations of interacting labels, such as the fluorescence resonance energy transfer (FRET) pairs disclosed by Tyagi et al. in U.S. Pat. No. 5,925,517), chemiluminescent molecules, enzymes, cofactors, enzyme substrates, haptens or other ligands. With the hybridization assay probes of the present invention, the probes are preferably labeled by means of a non-nucleotide linker with an acridinium ester (AE), such as standard AE. Acridinium ester labeling may be performed as disclosed by Arnold et al., "Acridinium Ester Labelling and Purification of Nucleotide Probes," U.S. Pat. No. 5,185,439.

D. Nucleic Acid Amplification

Preferably, the amplification primers of the present invention are oligodeoxynucleotides and are sufficiently long to be used as a substrate for the synthesis of extension products by a nucleic acid polymerase. Optimal primer length should take into account several factors, including the temperature of reaction, the structure and base composition of the primer, and how the primer is to be used. For example, for optimal specificity the oligonucleotide primer generally should be at least 12 bases in length, depending on the complexity of the target nucleic acid sequence. If such specificity is not essential, shorter primers may be used. In such a case, it may be desirable to carry out the reaction at cooler temperatures in order to form stable hybrid complexes with the template nucleic acid.

Useful guidelines for designing amplification primers with desired characteristics are described above in the section entitled "Preparation of Oligonucleotides." Optimal sites for amplifying and probing contain at least two, and preferably three, conserved regions of *M. pneumoniae* and/or *M. genitalium* nucleic acid. These regions are about 15 to 350 bases in length, and preferably between about 15 and 150 bases in length.

The degree of amplification observed with a set of amplification primers (primers and/or promoter-primers) depends on several factors, including the ability of the primers to hybridize to their specific target sequences and their ability to be extended or copied enzymatically. While amplification primers of different lengths and base compositions may be used, amplification primers preferred in this invention have target binding regions of 18 to 40 bases with a predicted $T_m$ to target above 42° C., preferably at least about 50° C.

Parameters affecting probe hybridization, such as melting temperature, complementarity and secondary structure of the target sequence, also affect amplification primer hybridization and therefore performance of the amplification primers. The degree of non-specific extension (primer-dimer or non-target copying) can also affect amplification efficiency. Thus, amplification primers are generally selected to have low self-complementarity or cross-complementarity, particularly at the 3' ends of their sequences. Notwithstanding, amplification primers including regions of self-complementarity may be useful, such as the self-reporting "signal primers" disclosed by Nadeau et al., "Detection of Nucleic Acids by Fluorescence Quenching," U.S. Pat. No. 5,958, 700, and the "hairpin primers" disclosed by Nazarenko et al., "Nucleic Acid Amplification Oligonucleotides with Molecular Energy Transfer Labels and Methods Based Thereon," U.S. Pat. No. 5,866,336. Lengthy homopolymer runs and high GC content are avoided to reduce spurious primer extension. Computer programs are available to aid in this aspect of the design, including Oligo Tech® analysis software available from Oligo Therapeutics, Inc. and accessible on the World Wide Web at the following URL: http://www.oligosetc.com.

A nucleic acid polymerase used in conjunction with the amplification primers of the present invention refers to a chemical, physical or biological agent which incorporates either ribonucleotides or deoxyribonucleotides, or both, into a nucleic acid polymer, or strand, in a template-dependent manner. Examples of nucleic acid polymerases include DNA-directed DNA polymerases, RNA-directed DNA polymerases, and RNA-directed RNA polymerases. DNA polymerases bring about nucleic acid synthesis in a template-dependent manner and in a 5' to 3' direction. Because of the typical anti-parallel orientation of the two strands in a double-stranded nucleic acid, this direction is from a 3' region on the template to a 5' region on the template. Examples of DNA-directed DNA polymerases include *E. coli* DNA polymerase I, the thermostable DNA polymerase from *Thermus aquaticus* (*Taq*), and the large fragment of DNA polymerase I from *Bacillus stearothermophilus* (*Bst*).

See, e.g., Riggs et al., "Purified DNA Polymerase from *Bacillus stearothermophilus*," U.S. Pat. No. 6,066,483. Examples of RNA-directed DNA polymerases include various retroviral reverse transcriptases, such as Moloney murine leukemia virus (MMLV) reverse transcriptase or avian myeloblastosis virus (AMV) reverse transcriptase.

During most nucleic acid amplification reactions, a nucleic acid polymerase adds nucleotide residues to the 3' end of the primer using the target nucleic acid as a template, thus synthesizing a second nucleic acid strand having a nucleotide sequence partially or completely complementary to a region of the target nucleic acid. In many nucleic acid amplification reactions, the two strands comprising the resulting double-stranded structure must be separated by chemical or physical means in order to allow the amplification reaction to proceed. Alternatively, the newly-synthesized template strand may be made available for hybridization with a second primer or promoter-primer by other means, such as through strand displacement or the use of a nucleolytic enzyme which digests part or all of the original target strand. In this way the process may be repeated through a number of cycles, resulting in a large increase in the number of nucleic acid molecules having the target nucleotide sequence.

Either the first or second amplification primer, or both, may be a promoter-primer. (In some applications, the amplification primers may only consist of promoter-primers which are complementary to the sense strand, as disclosed by Kacian et al., "Nucleic Acid Sequence Amplification Method, Composition and Kit," U.S. Pat. No. 5,554,516.) A promoter-primer usually contains an oligonucleotide that is not complementary to a nucleotide sequence present in the target nucleic acid molecule or primer extension product(s) (see, e.g., Kacian et al., "Nucleic Acid Sequence Amplification Methods," U.S. Pat. No. 5,399,491). These non-complementary sequences may be located 5' to the complementary sequences on the amplification primer and may provide a locus for initiation of RNA synthesis when made double-stranded through the action of a nucleic acid polymerase. The promoter thus provided may allow for the in vitro transcription of multiple RNA copies of the target nucleic acid sequence. It will be appreciated that all references to primers herein are inclusive of primers and promoter-primers, unless the context clearly indicates otherwise.

E. Sample Processing

Sample processing prior to amplification or detection of a target sequence may be necessary or useful for discriminating a target sequence from non-target nucleic acid present in a sample. Sample processing procedures may include, for example, direct or indirect immobilization of nucleic acids and/or oligonucleotides from the liquid phase in a heterogeneous assay. With some procedures, such immobilization may require multiple hybridization events. Ranki et al., "Detection of Microbial Nucleic Acids by a One-Step Sandwich Hybridization Test," U.S. Pat. Nos. 4,486,539 and 4,563,419, for example, disclose a one-step nucleic acid "sandwich" hybridization method involving the use of a solid-phase bound nucleic acid having a target complementary sequence and a labeled nucleic acid probe which is complementary to a distinct region of the target nucleic acid. Stabinsky, "Methods and Kits for Performing Nucleic Acid Hybridization Assays," U.S. Pat. No. 4,751,177, discloses methods including a "mediator" polynucleotide that reportedly overcomes sensitivity problems associated with Ranki's method resulting from leakage of immobilized probe from the solid support. Instead of directly immobilizing the target nucleic acid, the mediator polynucleotides of Stabinsky are used to bind and indirectly immobilize target polynucleotide:probe polynucleotide complexes which have formed free in solution.

Any known solid support may be used for sample processing, such as matrices and particles free in solution. The solid support may be, for example, nitrocellulose, nylon, glass, polyacrylate, mixed polymers, polystyrene, silane polypropylene and, preferably, particles having a magnetic charge to facilitate recovering sample and/or removing unbound nucleic acids or other sample components. Particularly preferred supports are magnetic spheres that are monodisperse (i.e., uniform in size ±5%), thereby providing consistent results, which is particularly advantageous for use in an automated procedure. One such automated procedure is disclosed by Ammann et al., "Automated Process for Isolating and Amplifying a Target Nucleic Acid Sequence," U.S. Pat. No. 6,335,166.

An oligonucleotide for immobilizing a target nucleic acid on a solid support may be joined directly or indirectly to the solid support by any linkage or interaction which is stable under assay conditions (e.g., conditions for amplification and/or detection). Referred to herein as an "immobilized probe," this oligonucleotide may bind directly to the target nucleic acid or it may include a base sequence region, such as a homopolymeric tract (e.g., a poly dT) or a simple short repeating sequence (e.g., an AT repeat), which hybridizes to a complementary base sequence region present on a capture probe. Direct joining occurs when the immobilized probe is joined to the solid support in the absence of an intermediate group. For example, direct joining may be via a covalent linkage, chelation or ionic interaction. Indirect joining occurs when the immobilized probe is joined to the solid support by one or more linkers. A "linker" is a means for binding at least two different molecules into a stable complex and contains one or more components of a binding partner set.

Members of a binding partner set are able to recognize and bind to each other. Binding partner sets may be, for example, receptor and ligand, enzyme and substrate, enzyme and cofactor, enzyme and coenzyme, antibody and antigen, sugar and lectin, biotin and streptavidin, ligand and chelating agent, nickel and histidine, substantially complementary oligonucleotides, and complementary homopolymeric nucleic acids or homopolymeric portions of polymeric nucleic acids. Components of a binding partner set are the regions of the members that participate in binding.

A preferred sample processing system having practical advantages in terms of its ease of use and rapidity comprises an immobilized probe containing a base sequence which is complementary to a base sequence of a capture probe, referred to herein as an "immobilized probe binding region." The capture probe additionally contains a base sequence, referred to herein as a "target binding region," which may specifically hybridize to a target sequence contained in a target nucleic acid under assay conditions. (While specificity of the target binding region of the capture probe for a region of the target nucleic acid is desirable to minimize the number of non-target nucleic acids remaining from the sample after a separation step, it is not a requirement of the capture probes of the present invention if the capture probes are being used solely to isolate target nucleic acid.) If the capture probe is not being employed to isolate a target nucleic acid for subsequent amplification of a target sequence, the capture probe may further include a detectable label attached within or near the target binding region, such as a substituted or unsubstituted acridinium ester. The labeled capture probe may be used in a homogeneous or semi-homogenous assay to specifically detect hybrid nucleic acids without detecting single-stranded nucleic acids, such as the capture probe. A preferred homogenous assay which could be used with this system is the hybridization protection assay (HPA), which is discussed above in the section entitled "Hybridization Conditions and Probe Design." Following the HPA format, label associated with capture probes which have not hybridized to target nucleic acids would be hydrolyzed with the addition of a mild base, while label associated with capture probe:target hybrids would be protected from hydrolysis.

An advantage of this latter assay system is that only a single target-specific hybridization event (capture probe:target) is necessary for target detection, rather than multiple such events (e.g, capture probe:target and probe:target or probe:amplicon) which are required in other sample processing procedures described herein. Also, fewer oligonucleotides in an assay tend to make the assay faster and simpler to optimize, since the overall rate at which a target nucleic acid is captured and detected is limited by the slowest hybridizing oligonucleotide. While the target binding region of a capture probe may be less specific in alternative assay systems, it must still be rare enough to avoid significant saturation of the capture probe with non-target nucleic acids. Thus, the requirement that two separate and specific target sequences be identified in these alternative systems could place constraints on the identification of an appropriate target. By contrast, only one such target sequence is needed when the capture probe simultaneously functions as the detection probe.

Whichever approach is adopted, the assay needs to include means for detecting the presence of the target nucleic acid in the test sample. A variety of means for detecting target nucleic acids are well known to those skilled in the art of nucleic acid detection, including means which do not require the presence of a detectable label. Nevertheless, probes including a detectable label are preferred. A labeled probe for detecting the presence of a target nucleic acid would have to include a base sequence which is substantially complementary and specifically hybridizes to a target sequence contained in the target nucleic acid. Once the probe stably binds to the target nucleic acid, and the resulting target:probe hybrid has been directly or indirectly immobilized, unbound probe can be washed away or inactivated and the remaining bound probe can be detected and/or measured.

Preferred sample processing systems combine the elements of detection and nucleic acid amplification. These systems first directly or indirectly immobilize a target nucleic acid using a capture probe, the captured target nucleic acid is purified by removing inter alia cellular debris, non-target nucleic acid and amplification inhibitors from the sample-containing vessel, which is followed by amplification of a target sequence contained in the target nucleic acid. Amplified product is then detected, preferably in solution with a labeled probe. (The target nucleic acid may remain in the immobilized state during amplification or it may be eluted from the solid support prior to amplification using appropriate conditions, such as by first incubating at a temperature above the $T_m$ of the capture probe:target complex and/or the $T_m$ of the capture probe:immobilized probe complex.) A preferred embodiment of this system is disclosed by Weisburg et al., "Two-Step Hybridization and Capture of a Polynucleotide," U.S. Pat. No. 6,110,678. In this system, the capture probe hybridizes to the target nucleic acid and an immobilized probe hybridizes to the capture probe:target complex under different hybridization conditions. Under a first set of hybridization conditions, hybridization of the capture probe to the target nucleic acid is favored over hybridization of the capture probe to the immobilized probe. Thus, under this first set of conditions, the capture probe is in solution rather than bound to a solid support, thereby maximizing the concentration of the free capture probe and utilizing favorable liquid phase kinetics for hybridization to the target nucleic acid. After the capture probe has had sufficient time to hybridize to the target nucleic acid, a second set of hybridization conditions is imposed permitting in the capture probe:target complex to hybridize to the immobilized probe, thereby isolating the target nucleic acid in the sample solution. The immobilized target nucleic acid may then be purified, and a target sequence present in the target nucleic acid may be amplified and detected. A purification procedure which includes one or more wash steps is generally desirable when working with crude samples (e.g., clinical, environmental, industrial, food, water, etc.) to prevent enzyme inhibition and/or nucleic acid degradation due to substances present in the sample.

A preferred amplification method is the transcription-mediated amplification method disclosed by Kacian et al., "Nucleic Acid Sequence Amplification Methods," U.S. Pat. No. 5,480,789. In accord with this method, a promoter-primer having a 3' region complementary to a portion of the target and a 5' promoter region and a primer having the same nucleotide sequence as a portion of the target are contacted with a target RNA molecule. The primer and promoter-primer define the boundaries of the target region to be amplified, including both the sense present on the target molecule and its complement, and thus the length and sequence of the amplicon. In this preferred embodiment, the amplification oligonucleotides and immobilized target RNA are contacted in the presence of effective amounts of Moloney murine leukemia virus-derived reverse transcriptase and T7 RNA polymerase, both ribonucleotide and deoxyribonucleotide triphosphates, and necessary salts and cofactors at 42° C. Under these conditions, nucleic acid amplification occurs, resulting predominantly in the production of RNA amplicons of a sense opposite to that of the target nucleic acid. These amplicons can then be detected in solution by, for example, using an acridinium ester-labeled hybridization assay probe of the same sense as the target nucleic acid, employing HPA, as disclosed by Arnold et al. in U.S. Pat. No. 5,283,174.

The 3' terminus of the immobilized probe and the capture probe are preferably "capped" or blocked to prevent or inhibit their use as templates for nucleic acid polymerase activity. Capping may involve adding 3' deoxyribonucleotides (such as cordycepin), 3',2'-dideoxynucleotide residues, non-nucleotide linkers, such as those disclosed by Arnold et al. in U.S. Pat. No. 6,031,091, alkane-diol modifications, or non-complementary nucleotide residues at the 3' terminus.

Those skilled in the art will recognize that the above-described methodology is amenable, either as described or with obvious modifications, to various other amplification schemes, including, for example, the polymerase chain reaction (PCR), Qβ replicase-mediated amplification, self-sustained sequence replication (3SR), strand displacement amplification (SDA), nucleic acid sequence-based amplification (NASBA), loop-mediated isothermal amplification (LAMP), and the ligase chain reaction (LCR).

F. Capture Probes for Isolating M. Ribosomal Nucleic Acid

Capture probes of the present invention are designed to bind to and isolate nucleic acid derived from the 16S ribosomal nucleic acid of a *Mycoplasma* organism in the presence of non-target nucleic acid. As such, the capture probes include both a target binding region and an immobilized probe binding region. The target binding region of the capture probes includes a base sequence which hybridizes to a target sequence derived from 16S ribosomal nucleic acid from a *Mycoplasma* organism under assay conditions. While not essential, the target binding region preferably exhibits specificity for the target sequence in the presence of non-target nucleic acid under assay conditions. The immobilized probe binding region has a base sequence which hybridizes to an immobilized probe comprising a polynucleotide, or a chimeric containing polynucleotide sequences, which is joined to a solid support present in the test sample, either directly or indirectly. The target binding region and the immobilized probe binding region may be joined to each other directly or by means of, for example, a nucleotide base sequence, an abasic sequence or a non-nucleotide linker.

In a preferred embodiment, capture probes according to the present invention include a target binding region comprising a base sequence region which is at least about 85% homologous (preferably at least about 90% homologous, more preferably at least about 95% homologous, and most preferably 100% homologous) to a base sequence selected from the group consisting of SEQ ID NO:13, SEQ ID NO:14, SEQ ID NO:15, SEQ ID NO:16, SEQ ID NO:17, SEQ ID NO:18, SEQ ID NO:19 and SEQ ID NO:20. The immobilized probe binding region of these preferred capture probes comprises a base sequence which hybridizes to an immobilized probe joined directly or indirectly to a solid support provided to the test sample under assay conditions. The immobilized probe binding region preferably comprises a homopolymeric region (e.g., poly dA) located at the 3' end of the capture probe which is complementary to a homopolymeric region (e.g., poly dT) located at the 5' end of the immobilized probe. Other base sequences may be incorporated into the immobilized probe binding region, including, for example, short repeating sequences.

To prevent undesirable cross-hybridization reactions, the capture probes of the present invention preferably exclude nucleotide base sequences, other than the nucleotide base sequence of the target binding region, which can stably bind to nucleic acid derived from any organism which may be present in the test sample under assay conditions. Consistent with this approach, and in order to maximize the immobilization of capture probe:target complexes which are formed, the nucleotide base sequence of the immobilized probe binding region is preferably designed so that it can stably bind to a nucleotide base sequence present in the immobilized probe under assay conditions and not to nucleic acid derived from any organism which may be present in the test sample.

The target binding region and the immobilized probe binding region of the capture probe may be selected so that the capture probe:target complex has a higher $T_m$ than the $T_m$ of the capture probe:immobilized probe complex. In this way, a first set of conditions may be imposed which favors hybridization of the capture probe to the target sequence over the immobilized probe, thereby providing for optimal liquid phase hybridization kinetics for hybridization of the capture probe to the target sequence. Once sufficient time has passed for the capture probe to bind to the target sequence, a second set of less stringent conditions may be imposed which allows for hybridization of the capture probe to the immobilized probe. An example of differing hybridization conditions for capturing a target nucleic acid on a solid support is set for in Example 4 infra. Other sets of conditions could be established by those skilled in the art without engaging in anything more than routine experimentation.

Capture probes of the present invention may also include a label or a pair of interacting labels for direct detection of the target sequence in a test sample. Non-limiting examples of labels, combinations of labels and means for labeling probes are set forth supra in the section entitled "Preparation of Oligonucleotides" and infra in the section entitled "Hybridization Assay Probes to *M. pneumoniae* and/or *M. genitalium* Ribosomal Nucleic Acid." A particularly useful method for detecting the presence of a capture probe hybridized to a target nucleic acid is the hybridization protection assay (HPA), which is described above in the section entitled "Hybridization Conditions and Probe Design." HPA is a homogenous assay which distinguishes between probe hybridized to target nucleic acid and probe which remains unhybridized. Signal detected from an HPA reaction vessel provides an indication of the presence or amount of target organisms in the test sample.

Despite their application in a direct detection assay, the most common use of capture probes is in the isolation and purification of target nucleic acid prior to amplifying a target sequence contained in the target nucleic acid. By isolating and purifying the target nucleic acid prior to amplification, the number of unintended amplification reactions (i.e., amplification of non-target nucleic acid) can be severely limited. And, to prevent or inhibit the capture probe itself from functioning as a template for nucleic acid polymerase activity in the presence of amplification reagents and under amplification conditions, the 3' end of the capture probe may be capped or blocked. Examples of capping agents include 3' deoxyribonucleotides, 3',2'-dideoxynucleotide residues, non-nucleotide linkers, alkane-diol modifications, and non-complementary nucleotide residues at the 3' terminus.

G. Amplification of *Mycoplasma* Ribosomal Nucleic Acid

The amplification primers of the present invention are directed to regions of 16S ribosomal nucleic acid derived from *Mycoplasma* organisms. The amplification primers may flank, overlap or be contained within at least one of the target nucleic acid sequences of a hybridization assay probe (or its complement) used to detect the presence of a *Mycoplasma* organism in a nucleic acid amplification assay. As indicated above, the amplification primers may also include non-complementary bases at their 5' ends comprising a promoter sequence able to bind an RNA polymerase and direct RNA transcription using the target nucleic acid as a template. A T7 promoter sequence, such as SEQ ID NO:41, may be used.

Amplification primers of the present invention are capable of amplifying a target nucleic acid sequence present in nucleic acid derived from *Mycoplasma* organisms under amplification conditions. These amplification primers comprise an oligonucleotide having a target binding region, where the base sequence of the target binding region has or substantially corresponds to the base sequence of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39 or SEQ ID NO:40. Amplification primers of the present invention do not, however, include an amplification primer comprising an oligonucleotide having a target binding region, where the base sequence of the target binding region has or substantially corresponds to the base sequence of SEQ ID NO:25, SEQ ID NO:26, SEQ ID NO:27, SEQ ID NO:28, SEQ ID NO:37, SEQ ID NO:38, SEQ ID NO:39 or SEQ ID NO:40, except in combination with an amplification primer comprising an oligonucleotide having a target binding region, where the target binding region has or substantially corresponds to the base sequence of SEQ ID NO:21, SEQ ID NO:22, SEQ ID NO:23, SEQ ID NO:24, SEQ ID NO:29, SEQ ID NO:30, SEQ ID NO:31, SEQ ID NO:32, SEQ ID NO:33, SEQ ID NO:34, SEQ ID NO:35 and SEQ ID NO:36. The target binding region of an amplification primer according to the present invention is preferably at least about 80% homologous (more preferably at least about 90% homologous and most preferably 100% homologous) to the recited base sequence. Amplification primers of the present invention have a target binding region which is preferably at least 12 bases in length and more preferably from 18 to 40 bases in length.

Where the base sequence of the target binding region has or substantially corresponds to the base sequence of SEQ ID NO:21, SEQ ID NO:22, SEQ ID NO:23, SEQ ID NO:24, SEQ ID NO:29, SEQ ID NO:30, SEQ ID NO:31, SEQ ID NO:32, SEQ ID NO:33, SEQ ID NO:34, SEQ ID NO:35 or SEQ ID NO:36, the base sequence of the target binding region is preferably at least, about 80% homologous (more preferably at least about 90% homologous and most preferably 100% homologous) to the base sequence of SEQ ID NO:21, SEQ ID NO:22, SEQ ID NO:23, SEQ ID NO:24, SEQ ID NO:29, SEQ ID NO:30, SEQ ID NO:31, SEQ ID NO:32, SEQ ID NO:33, SEQ ID NO:34, SEQ ID NO:35 or SEQ ID NO:36. And, with the exception of an optional 5' sequence recognized by an RNA polymerase or which enhances initiation or elongation by an RNA polymerase, the base sequence of an amplification primer in the most preferred embodiment of the present invention is at least about 80% homologous (more preferably at least about 90% homologous and most preferably 100% homologous) to the base sequence of SEQ ID NO:21, SEQ ID NO:22, SEQ ID NO:23, SEQ ID NO:24, SEQ ID NO:29, SEQ ID NO:30, SEQ ID NO:31, SEQ ID NO:32, SEQ ID NO:33, SEQ ID NO:34, SEQ ID NO:35 or SEQ ID NO:36.

In one preferred embodiment, a set of at least two amplification primers for amplifying nucleic acid from a *Mycoplasma* organism is provided which includes: (i) a first amplification primer comprising an oligonucleotide having a target binding region, where the base sequence of the target binding region has or substantially corresponds to the base sequence of SEQ ID NO:21, SEQ ID NO:22, SEQ ID NO:23 or SEQ ID NO:24; and (ii) a second amplification primer comprising an oligonucleotide having a target binding region, where the base sequence of the target binding region has or substantially corresponds to the base sequence of SEQ ID NO:29, SEQ ID NO:30, SEQ ID NO:31 or SEQ ID NO:32. Preferably, the base sequence of the target binding region of the first amplification primer has or substantially corresponds to the base sequence of SEQ ID NO:21, and the base sequence of the target binding region of the second amplification primer has or substantially corresponds to the base sequence of SEQ ID NO:29. In a preferred mode, the second amplification primer further includes a 5' sequence which is recognized by an RNA polymerase or which enhances initiation or elongation by an RNA polymerase.

In another preferred embodiment, a set of at least two amplification primers for amplifying nucleic acid from a *Mycoplasma* organism is provided which includes: (i) a first amplification primer comprising an oligonucleotide having a target binding region, where the base sequence of the target binding region has or substantially corresponds to the base sequence of SEQ ID NO:21, SEQ ID NO:22, SEQ ID NO:23 or SEQ ID NO:24; and (ii) a second amplification primer comprising an oligonucleotide having a target binding region, where the base sequence of the target binding region has or substantially corresponds to the base sequence of SEQ ID NO:33, SEQ ID NO:34, SEQ ID NO:35 or SEQ ID NO:36. Preferably, the base sequence of the target binding region of the first amplification primer has or substantially corresponds to the base sequence of SEQ ID NO:21, and the base sequence of the target binding region of the second amplification primer has or substantially corresponds to the base sequence of SEQ ID NO:33. In a preferred mode, the second amplification primer further includes a 5' sequence which is recognized by an RNA polymerase or which enhances initiation or elongation by an RNA polymerase.

In yet another preferred embodiment, a set of at least two amplification primers for amplifying nucleic acid from a *Mycoplasma* organism is provided which includes: (i) a first amplification primer comprising an oligonucleotide having a target binding region, where the base sequence of the target binding region has or substantially corresponds to the base sequence of SEQ ID NO:21, SEQ ID NO:22, SEQ ID NO:23 or SEQ ID NO:24; and (ii) a second amplification primer comprising an oligonucleotide having a target binding region, where the base sequence of the target binding region has or substantially corresponds to the base sequence of SEQ ID NO:37, SEQ ID NO:38, SEQ ID NO:39 or SEQ ID NO:40. Preferably, the base sequence of the target binding region of the first amplification primer has or substantially corresponds to the base sequence of SEQ ID NO:21, and the base sequence of the target binding region of the second amplification primer has or substantially corresponds to the base sequence of SEQ ID NO:37. In a preferred mode, the second amplification primer further includes a 5' sequence which is recognized by an RNA polymerase or which enhances initiation or elongation by an RNA polymerase.

In still another preferred embodiment, a set of at least two amplification primers for amplifying nucleic acid from a *Mycoplasma* organism is provided which includes: (i) a first amplification primer comprising an oligonucleotide having a target binding region, where the base sequence of the target binding region has or substantially corresponds to the base sequence of SEQ ID NO:25, SEQ ID NO:26, SEQ ID NO:27 or SEQ ID NO:28; and (ii) a second amplification primer comprising an oligonucleotide having a target binding region, where the base sequence of the target binding region has or substantially corresponds to the base sequence of SEQ ID NO:29, SEQ ID NO:30, SEQ ID NO:31 or SEQ ID NO:32. Preferably, the base sequence of the target binding region of the first amplification primer has or substantially corresponds to the base sequence of SEQ ID NO:25, and the base sequence of the target binding region of the second amplification primer has or substantially corresponds to the base sequence of SEQ ID NO:29. In a preferred mode, the second amplification primer further includes a 5' sequence which is recognized by an RNA polymerase or which enhances initiation or elongation by an RNA polymerase.

In a further preferred embodiment, a set of at least two amplification primers for amplifying nucleic acid from a

*Mycoplasma* organism is provided which includes: (i) a first amplification primer comprising an oligonucleotide having a target binding region, where the base sequence of the target binding region has or substantially corresponds to the base sequence of SEQ ID NO:25, SEQ ID NO:26, SEQ ID NO:27 or SEQ ID NO:28; and (ii) a second amplification primer comprising an oligonucleotide having a target binding region, where the base sequence of the target binding region has or substantially corresponds to the base sequence of SEQ ID NO:33, SEQ ID NO:34, SEQ ID NO:35 or SEQ ID NO:36. Preferably, the base sequence of the target binding region of the first amplification primer has or substantially corresponds to the base sequence of SEQ ID NO:25, and the base sequence of the target binding region of the second amplification primer has or substantially corresponds to the base sequence of SEQ ID NO:33. In a preferred mode, the second amplification primer further includes a 5' sequence which is recognized by an RNA polymerase or which enhances initiation or elongation by an RNA polymerase.

Amplification primers of the present invention may have modifications, such as blocked 3' and/or 5' termini (as discussed above) or sequence additions including, but not limited to, a specific nucleotide sequence recognized by an RNA polymerase (e.g., the promoter sequence for T7, T3 or SP6 RNA polymerase), a sequence which enhances initiation or elongation of RNA transcription by an RNA polymerase, or a sequence which may provide for intra-molecular base pairing and encourage the formation of secondary or tertiary nucleic acid structures.

Amplification primers are used in a nucleic acid amplification procedure, such as the polymerase chain reaction (PCR), Qβ replicase-mediated amplification, self-sustained sequence replication (3SR), transcription-mediated amplification (TMA), nucleic acid sequence-based amplification (NASBA), ligase chain reaction (LCR), strand displacement amplification (SDA) and loop-mediated isothermal amplification (LAMP), each of which is well known in the art. See, e.g., Mullis, "Process for Amplifying Nucleic Acid Sequences," U.S. Pat. No. 4,683,202; Erlich et al., "Kits for Amplifying and Detecting Nucleic Acid Sequences," U.S. Pat. No. 6,197,563; Walker et al., "Strand Displacement Amplification—an Isothermal, In Vitro DNA Amplification Technique," *Nucleic Acids Res.*, 20(7):1691–1696 (1992); Fahy et al., "Self-sustained Sequence Replication (3SR): An Isothermal Transcription-Based Amplification System Alternative to PCR," *PCR Methods and Applications*, 1:25–33 (1991); Kacian et al., U.S. Pat. No. 5,399,491; Davey et al., "Nucleic Acid Amplification Process," U.S. Pat. No. 5,554,517; Birkenmeyer et al., "Amplification of Target Nucleic Acids Using Gap Filling Ligase Chain Reaction," U.S. Pat. No. 5,427,930; Marshall et al., "Amplification of RNA Sequences Using the Ligase Chain Reaction," U.S. Pat. No. 5,686,272; Walker, "Strand Displacement Amplification," U.S. Pat. No. 5,712,124; Notomi et al., "Process for Synthesizing Nucleic Acid," U.S. Pat. No. 6,410,278; Dattagupta et al., "Isothermal Strand Displacement Amplification," U.S. Pat. No. 6,214,587; and HELEN H. LEE ET AL., NUCLEIC ACID AMPLIFICATION TECHNOLOGIES: APPLICATION TO DISEASE DIAGNOSIS (1997). Other amplification procedures not specifically indicated but which meet the definition of "nucleic acid amplification" supra are also contemplated by the inventors.

Amplification primers of the present invention are preferably unlabeled but may include one or more reporter groups to facilitate detection of a target nucleic acid in combination with or exclusive of a hybridization assay probe. A wide variety of methods are available to directly detect an amplified target sequence. For example, the nucleotide substrates or the primers can include a detectable label which is incorporated into newly synthesized DNA. The resulting labeled amplification product is then generally separated from the unused labeled nucleotides or primers and the label is detected in the separated product fraction. See, e.g., Wu, "Detection of Amplified Nucleic Acid Using Secondary Capture Oligonucleotides and Test Kit," U.S. Pat. No. 5,387,510.

A separation step is not required if the primer is modified by, for example, linking it to two dyes which form a donor/acceptor dye pair. The modified primer can be designed so that the fluorescence of one dye pair member remains quenched by the other dye pair member, so long as the primer does not hybridize to target nucleic acid, thereby physically separating the two dyes. Moreover, the primer can be further modified to include a restriction endonuclease recognition site positioned between the two dyes so that when a hybrid is formed between the modified primer and target nucleic acid, the restriction endonuclease recognition site is rendered double-stranded and available for cleavage or nicking by the appropriate restriction endonuclease. Cleavage or nicking of the hybrid then separates the two dyes, resulting in a change in fluorescence due to decreased quenching which can be detected as an indication of the presence of the target organism or organisms in the test sample. Such modified primers are disclosed by Nadeau et al., "Detection of Nucleic Acids by Fluorescence Quenching," U.S. Pat. Nos. 5,958,700 and 6,054,279.

Substances which can serve as useful detectable labels are well known in the art and include radioactive isotopes, fluorescent molecules, chemiluminescent molecules, chromophores, as well as ligands such as biotin and haptens which, while not directly detectable, can be readily detected by a reaction with labeled forms of their specific binding partners, e.g., avidin and antibodies, respectively.

Another approach is to detect the amplification product by hybridization with a detectably labeled probe and measuring the resulting hybrids in any conventional manner. In particular, the product can be assayed by hybridizing a chemiluminescent, acridinium ester-labeled probe to the target sequence, selectively hydrolyzing the acridinium ester present on unhybridized probe, and measuring the chemiluminescence produced from the remaining acridinium ester in a luminometer. See, e.g., Arnold et al., U.S. Pat. No. 5,283,174, and NORMAN C. NELSON ET AL., NONISOTOPIC PROBING, BLOTTING, AND SEQUENCING, ch. 17 (Larry J. Kricka ed., 2d ed. 1995).

H. Hybridization Assay Probes to *M. pneumoniae* or *M. genitalium* Ribosomal Nucleic Acid This embodiment of the invention relates to novel hybridization assay probes. Hybridization is the association of two single strands of complementary nucleic acid to form a hydrogen bonded double strand. A nucleic acid sequence able to hybridize to a nucleic acid sequence sought to be detected ("target sequence") can serve as a probe for the target sequence. Hybridization may occur between complementary nucleic acid strands, including DNA/DNA, DNA/RNA, and RNA/RNA. Two single strands of deoxyribo-(DNA) or ribo-(RNA) nucleic acid, formed from nucleotides (including the bases adenine (A), cytosine (C), thymidine (T), guanine (G), uracil (U), inosine (I), and analogs thereof, may hybridize to form a double-stranded structure in which the two strands are held together by hydrogen bonds between pairs of complementary bases. Generally, A is hydrogen-bonded to T or U, while G is hydrogen-bonded to C. At any point along the hybridized strands, therefore, the classical base pairs AT or AU, TA or UA, GC or CG may be found. Thus, when a first single strand of nucleic acid contains sufficient contiguous complementary bases to a second, and those two strands are brought together under conditions that will promote their hybridization, double-stranded nucleic acid will result. Under appropriate conditions, DNA/DNA, RNA/DNA, or RNA/RNA hybrids may be formed.

The rate and extent of hybridization is influenced by a number of factors. For instance, it is implicit that if one of the two strands is wholly or partially involved in a hybrid, it will be less able to participate in the formation of a new hybrid. By designing a probe so that a substantial portion of the sequence of interest is single-stranded, the rate and extent of hybridization may be greatly increased. Also, if the target is an integrated genomic sequence it will naturally occur in a double-stranded form, as is the case with a product of PCR. These double-stranded targets are naturally inhibitory to hybridization with a probe and require denaturation prior to the hybridization step. In addition, there can be intra-molecular hybrids formed within a probe if there is sufficient self-complementarity. Regions of the nucleic acid which are known to form strong internal structures inhibitory to hybridization are typically less preferred. Examples of such structures include hairpin loops. Undesirable secondary structure in a hybridization assay probe can be avoided through careful probe design, and commercial computer programs are available to search for these types of interactions, such as the Oligo Tech® analysis software available from Oligo Therapeutics, Inc.

In some applications, such as homogenous assays, probes exhibiting at least some degree of self-complementarity may be desirable to facilitate detection of probe:target duplexes in a test sample. Such probes include "molecular torches" which are designed to include distinct regions of self-complementarity referred to as the "target binding domain" and the "target closing domain." These two domains are connected by a joining region in the molecular torch and hybridize to each other under hybridization assay conditions. The joining region can be a non-nucleotide linker, such as polyethylene glycol. Molecular torches are disclosed by Becker et al., "Molecular Torches," U.S. Pat. No. 6,361,945.

When exposed to denaturing conditions, the two complementary regions (which may be fully or partially complementary) of the molecular torch melt, leaving the target binding domain available for hybridization to a target sequence when the original hybridization assay conditions are restored. Molecular torches are designed so that the target binding domain favors hybridization to the target sequence over the target closing domain. The target binding domain and the target closing domain of a molecular torch include interacting labels (e.g., luminescent/quencher) positioned so that a different signal is produced when the molecular torch is self-hybridized than when the molecular torch is hybridized to a target nucleic acid, thereby permitting detection of probe:target duplexes in a test sample in the presence of unhybridized probe having viable labels associated therewith.

In accordance with the teachings of Becker et al. in U.S. Pat. No. 6,361,945, hybridization assay probes of the present invention may be designed and constructed to include, in addition to a "target binding domain" able to distinguish between nucleic acid derived from *M. pneumoniae* and *M. genitalium*, a "target closing domain," a "joining region" and interacting labels characteristic of a molecular torch.

Another example of a self-complementary hybridization assay probe is a "molecular beacon." Molecular beacons include nucleic acid molecules having a target complement sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complement sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Examples of various molecular beacon configurations and applications are disclosed by Tyagi et al. in U.S. Pat. No. 5,925,517. In accordance with the teachings of Tyagi et al., probes according to the present invention may be designed and constructed to include, in addition to a "target complement sequence" able to distinguish between nucleic acid derived from *M. pneumoniae* and *M. genitalium*, an "affinity pair" and dual labels characteristic of a molecular beacon.

The rate at which a probe hybridizes to its target is one measure of the thermal stability of the target secondary structure in the probe region. The standard measurement of hybridization rate is the $C_o t_{1/2}$, which is measured as moles of nucleotides per liter times seconds. Thus, it is the concentration of probe times the time at which 50% of maximal hybridization occurs at that concentration. This value is determined by hybridizing various amounts of probe to a constant amount of target for a fixed time. The $C_o t_{1/2}$ is found graphically by standard procedure. The probe:target hybrid melting temperature may be determined by isotopic methods well-known to those skilled in the art. The melting temperature for a given hybrid will vary depending on the hybridization solution being used.

Thus, in a first aspect, the invention features hybridization assay probes able to distinguish between nucleic acid derived from *M. pneumoniae* and *M. genitalium*, by virtue of the ability of the probe to preferentially hybridize to nucleic acid derived from either *M. pneumoniae* or *M. genitalium* under stringent hybridization assay conditions. Specifically, the probes contain an oligonucleotide having a base sequence that is substantially complementary to a target sequence present in nucleic acid derived from *M. pneumoniae* or *M. genitalium*. A probe according to the present invention may detect less than all members of the species targeted, either *M. pneumoniae* or *M. genitalium*, and still be characterized as either a *M. pneumoniae* or *M. genitalium* probe, provided the probe is capable of detecting the presence of at least one strain belonging to the species targeted under stringent hybridization assay conditions. Notwithstanding, it is believed that the probes of the present invention are able to detect all strains of *M. pneumoniae* or *M. genitalium*.

In the case of a hybridization assay, the length of the target nucleic acid sequence and, accordingly, the length of the probe sequence can be important. In some cases, there may be several sequences from a particular region, varying in location and length, which will yield probes with the desired hybridization characteristics. In other cases, one sequence may have better hybridization characteristics than another that differs merely by a single base. While it is possible for nucleic acids that are not perfectly complementary to hybridize, the longest stretch of perfectly homologous base sequence will normally primarily determine hybrid stability.

While probes of different lengths and base composition may be used, the probes preferred in this invention have oligonucleotides that are up to 100 bases in length, more preferably from 12 to 50 bases in length, and even more preferably from 18 to 35 bases in length.

The hybridization assay probes include a base sequence that is substantially complementary to a 16S rRNA or rDNA target sequence present in or derived from the nucleic acid of *M. pneumoniae* or *M. genitalium*. Thus, the probes are able to stably bind to a *M. pneumoniae* or *M. genitalium* target sequence under stringent hybridization assay conditions. As discussed above, the hybridization assay probes may have additional base sequences which do not stably bind to the target nucleic acid.

In addition to self-complementary probes, probes of the present invention may be designed and constructed to include an immobilized probe binding region of a capture probe, where the immobilized probe binding region is comprised of a nucleotide base sequence which can hybridize under predetermined hybridization conditions to a substantially complementary nucleotide base sequence contained in an immobilized probe joined directly or indirectly to a solid support. (Examples of solid supports and means for joining oligonucleotides to solid supports are described supra in the section entitled "Sample Processing".) The immobilized probe binding region is preferably selected so that it will not stably bind under the predetermined hybridization conditions to nucleic acid from any organism which may be present in the test sample, including *M. pneumoniae* or *M. genitalium*. Thus, a preferred nucleotide base sequence for the immobilized probe binding region of a capture probe according to the present invention is a homopolymer tail, such as a 3' poly dA tail matched to a 5' poly dT tail on the immobilized probe. These tails may be of any length sufficient to facilitate stable hybridization under predetermined hybridization conditions and are preferably about 30 bases in length.

The immobilized probe is preferably joined to a magnetically charged particle which can be isolated in a reaction vessel during a purification step once the probe has had sufficient time to hybridize to target nucleic acid present in the sample. (Acosta et al., "Assay Work Station," U.S. Pat. No. 6,254,826, disclose an instrument for performing such a purification step.) The capture probe is preferably designed so that the melting temperature of the capture probe:target hybrid is greater than the melting temperature of the capture probe:immobilized probe hybrid. In this way, different sets of hybridization assay conditions can be employed to facilitate hybridization of the capture probe to the target nucleic acid prior to hybridization of the capture probe to the immobilized oligonucleotide, thereby maximizing the concentration of free probe and providing favorable liquid phase hybridization kinetics. This "two-step" target capture method is discussed above and disclosed by Weisburg et al., U.S. Pat. No. 6,110,678. Other target capture schemes which could be readily adapted to the present invention are well known in the art and include, without limitation, those disclosed by the following: Dunn et al., *Methods in Enzymology*, "Mapping viral mRNAs by sandwich hybridization," 65(1):468–478 (1980); Ranki et al., U.S. Pat. No. 4,486,539; Stabinsky, U.S. Pat. No. 4,751,177; and Becker et al., U.S. Pat. No. 6,130,038.

For *M. pneumoniae* probes, the terms "target nucleic acid sequence," "target nucleotide sequence," "target sequence" and "target region" all refer to a nucleic acid sequence present in *M. pneumoniae* rRNA or rDNA, or a sequence complementary thereto, which is not present in the nucleic acid of a closely related non-*M. pneumoniae* species. And for *M. genitalium*, these same terms refer to a nucleic acid sequence present in *M. genitalium* rRNA or rDNA, or a sequence complementary thereto, which is not present in the nucleic acid of a closely related non-*M genitalium* species. Nucleic acids having nucleotide sequences complementary to a target sequence may be generated by target amplification techniques, such as those discussed supra in the section entitled "Amplification of *Mycoplasma* Ribosomal Nucleic Acid."

Organisms that might be present in certain test samples containing *M. pneumoniae* or *M. genitalium* include, for example, *M. buccale, M. faucium, M. hominis, M. orate* and *M. salivarium*. Of these, *M. pneumoniae* and *M. genitalium* are the most closely related. This list of organisms is by no means intended to be fully representative of the organisms that the *M. pneumoniae* and *M. genitalium* probes of the present invention can be used to distinguish over. In general, it is expected that the *M. pneumoniae* probes of the present invention can be used to distinguish nucleic acid derived from *M. pneumoniae* over nucleic acid derived from of any non-*M. pneumoniae* organism present in a test sample, and the *M. genitalium* probes of the present invention can be used to distinguish nucleic acid derived from *M. genitalium* over nucleic acid derived from any non-*M genitalium* organism present in a test sample.

A *M. pneumoniae* probe of the present invention comprises an oligonucleotide having a target binding region, where the base sequence of the target binding region consists of or is contained within a base sequence selected from the group consisting of SEQ ID NO:1, SEQ ID NO:2, SEQ ID NO:3 and SEQ ID NO:4. The probe preferentially hybridizes under stringent hybridization conditions to a target nucleic acid derived from *M. pneumoniae* over nucleic acid derived from non-*M. pneumoniae* organisms, especially nucleic acid from *M. genitalium*, which may be present in the test sample. The probe does not include any other target complementary base sequence region overlapping with or in addition to the target binding region which is capable of forming a stable hybrid with nucleic acid derived from *M. pneumoniae* under the same conditions.

A *M. genitalium* probe of the present invention comprises an oligonucleotide having a target binding region, where the base sequence of the target binding region is contained within a base sequence selected from the group consisting of SEQ ID NO:5, SEQ ID NO:6, SEQ ID NO:7, SEQ ID NO:8, SEQ ID NO:9, SEQ ID NO:10, SEQ ID NO:11 and SEQ ID NO: 12. The probe preferentially hybridizes under stringent hybridization conditions to a target nucleic acid derived from *M. genitalium* over nucleic acid derived from non-*M. genitalium* organisms, especially nucleic acid from *M. pneumoniae*, which may be present in the test sample. The probe does not include any other target complementary base sequence region overlapping with or in addition to the target binding region which is capable of forming a stable hybrid with nucleic acid derived from *M. genitalium* under the same conditions.

Once synthesized, the probes may be labeled with a detectable label or reporter group by any well-known method. See, e.g., SAMBROOK ET AL., supra, ch. 10. The probe may be labeled with a detectable moiety such as a radioisotope, antigen or chemiluminescent moiety to facilitate detection of the target sequence. Useful labels include radioisotopes as well as non-radioactive reporting groups. Isotopic labels include $^{3}$H, $^{35}$S, $^{32}$P, $^{125}$I, $^{57}$Co and $^{14}$C. Isotopic labels can be introduced into an oligonucleotide by techniques known in the art such as nick translation, end labeling, second strand synthesis, reverse transcription and by chemical methods. When using radiolabeled probes, hybridization can be detected by techniques such as autoradiography, scintillation counting or gamma counting. The chosen detection method depends on the particular radioisotope used for labeling.

Non-isotopic materials can also be used for labeling and may be introduced internally between nucleotides or at an end of the oligonucleotide. Modified nucleotides may be incorporated enzymatically or chemically. Chemical modifications of the oligonucleotide may be performed during or after synthesis of the oligonucleotide using techniques known in the art. For example, through use of non-nucleotide linker groups disclosed by Arnold et al. in U.S. Pat. No. 6,031,091. Non-isotopic labels include fluorescent molecules, chemiluminescent molecules, fluorescent chemiluminescent molecules, phosphorescent molecules, electrochemiluminescent molecules, chromophores, enzymes, enzyme cofactors, enzyme substrates, dyes and haptens or other ligands. Another useful labeling technique is a base sequence that is unable to stably bind to the target nucleic acid under stringent conditions. Probes of the present invention are preferably labeled with an acridinium ester, particularly standard AE, which is joined to the probe by means of a non-nucleotide linker, such as the linking reagent depicted in FIG. 5. (Acridinium ester labeling techniques are disclosed by Arnold et al. in U.S. Pat. No. 5,185,439, and linking reagents are disclosed by Arnold et al. in U.S. Pat. No. 6,031,091.)

In a particularly preferred embodiment, *M. pneumoniae* probes according to the present invention comprise an oligonucleotide having a target binding region, where the base sequence of the target binding region consists of or is contained within the base sequence of SEQ ID NO:1 or SEQ ID NO:2, and an acridinium ester label joined to the probe by means of a non-nucleotide linker positioned between optionally modified nucleotides 14 and 15 (reading 5' to 3') of SEQ ID NO:1 or SEQ ID NO:2. Where the base sequence of the target binding region consists of or is contained within the base sequence of SEQ ID NO:3 or SEQ ID NO:4, an acridinium ester label is preferably joined to the probe by means of a non-nucleotide linker positioned between optionally modified nucleotides 18 and 19 (reading 5' to 3') of SEQ ID NO:3 or SEQ ID NO:4. Joining the acridinium ester labels to the probes is preferably carried out in accordance with the teachings of Arnold et al. in U.S. Pat. Nos. 5,185,439 and 6,031,091 using the non-nucleotide linker arm illustrated in FIG. 5.

In another particularly preferred embodiment, *M. genitalium* probes according to the present invention comprise an oligonucleotide having a target binding region, where the base sequence of the target binding region consists of or is contained within the base sequence SEQ ID NO:5 or SEQ ID NO:6, and an acridinium ester label joined to the probe by means of a non-nucleotide linker positioned between optionally modified nucleotides 16 and 17 (reading 5' to 3') of SEQ ID NO:5 or SEQ ID NO:6. Where the base sequence of the target binding region consists of or is contained within the base sequence of SEQ ID NO:7 or SEQ ID NO:8, an acridinium ester label is preferably joined to the probe by means of a non-nucleotide linker positioned between optionally modified nucleotides 16 and 17 (reading 5' to 3') of SEQ ID NO:7 or SEQ ID NO:8. Joining the acridinium ester labels to the probes is preferably carried out in accordance with the teachings of Arnold et al. in U.S. Pat. Nos. 5,185,439 and 6,031,091 using the non-nucleotide linker arm illustrated in FIG. 5.

The selected hybridization assay probe can then be contacted with a test sample suspected of containing *M. pneumoniae* or *M. genitalium*. Generally, the test sample is from a source which also contains unknown organisms. After bringing the probe into contact with the test sample, the test sample can be incubated under conditions permitting preferential hybridization of the probe to a target nucleic acid derived from *M. pneumoniae* or *M. genitalium* over nucleic acid derived from non-target organisms in the test sample.

The probe may also be combined with one or more unlabeled helper probes to facilitate binding to target nucleic acid derived from *M. pneumoniae* or *M. genitalium*. After the probe has hybridized to target nucleic acid present in the test sample, the resulting hybrid may be separated and detected by various techniques well known in the art, such as hydroxyapatite adsorption and radioactive monitoring. Other techniques include those which involve selectively degrading label associated with unhybridized probe and then measuring the amount of remaining label associated with hybridized probe, as disclosed by Arnold et al., in U.S. Pat. No. 5,283,174. This latter technique is particularly preferred.

I. Helper Probes Used in the Detection of *M. pneumoniae* and *M. genitalium*

Another embodiment of this invention relates to helper probes. As mentioned above, helper probes can be used to facilitate hybridization of hybridization assay probes to their intended target nucleic acids, so that the hybridization assay probes more readily form probe:target nucleic acid duplexes than they would in the absence of helper probes. (Helper probes are disclosed by Hogan et al. in U.S. Pat. No. 5,030,557.) Each helper probe contains an oligonucleotide that is sufficiently complementary to a target nucleic acid sequence to form a helper probe:target nucleic acid duplex under stringent hybridization assay conditions. The stringent hybridization assay conditions employed with a given helper probe are determined by the conditions used for preferentially hybridizing the associated hybridization assay probe to the target nucleic acid.

Regions of single stranded RNA and DNA can be involved in secondary and tertiary structures even under stringent hybridization assay conditions. Such structures can sterically inhibit or block hybridization of a hybridization assay probe to a target nucleic acid. Hybridization of the helper probe to the target nucleic acid alters the secondary and tertiary structures of the target nucleic acid, thereby rendering the target region more accessible by the hybridization assay probe. As a result, helper probes enhance the kinetics and/or the melting temperature of the hybridization assay probe:target nucleic acid duplex. Helper probes are generally selected to hybridize to nucleic acid sequences located near the target region of the hybridization assay probe.

Helper probes which may be used with the *M. pneumoniae* and/or *M. genitalium* hybridization assay probes of the present invention would be targeted to nucleic acid sequences within target nucleic acid derived from *M. pneumoniae* and/or *M. genitalium*. Each helper probe would preferably contain an at least 10 contiguous base region which is at least 80% complementary to an at least 10 contiguous base region present in a target sequence present in the target nucleic acid derived from *M. pneumoniae* and/or *M. genitalium*. Helper probes and their associated hybridization assay probes have different target sequences contained within the same target nucleic acid. Helper probes which may be used with the present invention are preferably oligonucleotides up to 100 bases in length, more preferably from 12 to 50 bases in length, and even more preferably from 18 to 35 bases in length. Alternatively, the helper probes may be at least 90% complementary, or even perfectly complementary, to their target regions.

J. Nucleic Acid Compositions

In another related aspect, the present invention features compositions comprising a nucleic acid hybrid formed between a hybridization assay probe and a target nucleic acid ("probe:target") under stringent hybridization assay conditions. One use of the hybrid formed between a probe and a target nucleic acid is to provide an indication of the presence or amount of a target organism or group of organisms in a test sample. For example, acridinium ester (AE) present in nucleic acid hybrids is resistant to hydrolysis in an alkali solution, whereas AE present in single-stranded nucleic acid is susceptible to hydrolysis in an alkali solution (see Arnold et al., U.S. Pat. No. 5,283,174). Thus, the presence of target nucleic acids can be detected, after the hydrolysis of the unbound AE-labeled probe, by measuring chemiluminescence of acridinium ester remaining associated with the nucleic acid hybrid.

The present invention also contemplates compositions comprising nucleic acid hybrids formed between a capture probe and a target nucleic acid ("capture probe:target") under stringent hybridization assay conditions. One use of the hybrid formed between a capture probe and a target nucleic acid is to isolate and purify the target nucleic acid in a test sample prior to amplification of a target sequence contained in the target nucleic acid or defection of the target nucleic acid in, for example, a heterogenous assay. By isolating and purifying target nucleic acid prior to amplification or detection, the opportunities for non-specific binding or amplification are significantly minimized.

The present invention further contemplates compositions comprising nucleic acid hybrids formed between a helper probe and a target nucleic acid ("helper probe:target") under stringent hybridization assay conditions. One use of the hybrid formed between a helper probe and a target nucleic acid is to make available a particular nucleic acid sequence for hybridization. For example, a hybrid formed between a helper probe and a target nucleic acid may render a nucleic acid sequence available for hybridization with a hybridization assay probe. Hogan et al. provide a description of helper probes in U.S. Pat. No. 5,030,557.

The present invention additionally features compositions comprising a nucleic acid formed between an amplification primer and a target nucleic acid ("primer:target") under amplification conditions. One use of the hybrid formed between a primer and a target nucleic acid is to provide an initiation site for a nucleic acid polymerase at the 3' end of the amplification primer. For example, a hybrid may form an initiation site for reverse transcriptase, DNA polymerases such as Taq polymerase or T4 DNA polymerase, and RNA polymerases such as T7 polymerase, SP6 polymerase, T3 polymerase and the like.

Compositions of the present invention include compositions for determining the presence or amount of *M. pneumoniae* in a test sample comprising a nucleic acid hybrid formed between a target nucleic acid derived from *M. pneumoniae* and a probe comprising an oligonucleotide having a target binding region, where the base sequence of the target binding region consists of or is contained within the base sequence of SEQ ID NO: 1, SEQ ID NO:2, SEQ ID NO:3 or SEQ ID NO:4. The oligonucleotides of these compositions may include at least one additional nucleotide base sequence region which does not stably bind to nucleic acid derived from *M. pneumoniae* under stringent hybridization conditions. In another embodiment, these probe:target compositions may further comprise at least one helper probe hybridized to the *M. pneumoniae*-derived target nucleic acid.

Compositions of the present invention may also include compositions for determining the presence or amount of *M. genitalium* in a test sample comprising a nucleic acid hybrid formed between a target nucleic acid derived from *M. genitalium* and a probe comprising an oligonucleotide having a target binding region, where the base sequence of the target binding region consists of or is contained within the base sequence of SEQ ID NO:5, SEQ ID NO:6, SEQ ID NO:7, SEQ ID NO:8, SEQ ID NO:9, SEQ ID NO:10, SEQ ID NO:11 or SEQ ID NO:12. The oligonucleotides of these compositions may include at least one additional nucleotide base sequence region which does not stably bind to nucleic acid derived from *M. genitalium* under stringent hybridization conditions. In another embodiment, these probe:target compositions may further comprise at least one helper probe hybridized to the *M. genitalium*-derived target nucleic acid.

Also contemplated by the present invention are compositions for immobilizing a target nucleic acid derived from a *Mycoplasma* organism present in a test sample comprising a nucleic acid hybrid formed between the target nucleic acid and a capture probe having a target binding region, where the base sequence of the target binding region is at least about 85% homologous (preferably at least about 90% homologous, more preferably at least about 95% homologous, and most preferably 100% homologous) to the base sequence of SEQ ID NO:13, SEQ ID NO:14, SEQ ID NO:15, SEQ ID NO:16, SEQ ID NO:17, SEQ ID:18, SEQ ID NO: 19 or SEQ ID NO:20. In a further embodiment, these compositions additionally include a nucleic acid hybrid formed between an immobilized probe binding region of the capture probe and an immobilized probe.

The present invention further contemplates compositions for amplifying a target sequence present in a target nucleic acid derived from a *Mycoplasma* organism comprising a nucleic acid hybrid formed between the target nucleic acid and an amplification primer comprising an oligonucleotide having a target binding region, where the base sequence of the target binding region is at least about 80% homologous (preferably at least about 90% homologous and more preferably 100% homologous) to the base sequence of SEQ ID NO:21, SEQ ID NO:22, SEQ ID NO:23, SEQ ID NO:24, SEQ ID NO:29, SEQ ID NO:30, SEQ ID NO:31, SEQ ID NO:32, SEQ ID NO:33, SEQ ID NO:34, SEQ ID NO:35 or SEQ ID NO:36. The amplification primer of these compositions optionally includes a 5' sequence which is recognized by an RNA polymerase or which enhances initiation or elongation by an RNA polymerase. When included, a T7 promoter, such as the nucleotide base sequence of SEQ ID NO:41, is preferred.

K. Assay Methods

The present invention contemplates various methods for assaying for the presence or amount of nucleic acid derived from *M. pneumoniae* or *M. genitalium* in a test sample. One skilled in the art will understand that the exact assay conditions, probes and/or primers used will vary depending on the particular assay format used and the source of the sample.

One aspect of the present invention relates to a method for determining the presence or amount of *M. pneumoniae* in a test sample by contacting the test sample under stringent hybridization assay conditions with a hybridization assay probe capable of preferentially hybridizing under stringent hybridization conditions to nucleic acid derived from *M. pneumoniae* over nucleic acid derived from non-*M. pneumoniae* organisms present in the test sample. In this method, the hybridization assay probe comprises an oligonucleotide having a target binding region, where the base sequence of the target binding region is contained within the base sequence of SEQ ID NO:1, SEQ ID NO:2, SEQ ID NO:3 or SEQ ID NO:4. The probes of this method may include at least one additional base sequence region which does not stably bind to nucleic acid derived from *M. pneumoniae* under stringent hybridization conditions. In another embodiment, this method for determining the presence or amount of *M. pneumoniae* in a test sample may also include the step of contacting the test sample with one or more helper probes for facilitating hybridization of the probe to the target nucleic acid. The helper probes may be added to the sample before or after the addition of the hybridization assay probe but are preferably provided to the test sample at the same time as the hybridization assay probe.

Another aspect of the present invention relates to a method for determining the presence or amount of *M. genitalium* in a test sample by contacting the test sample under stringent hybridization assay conditions with a hybridization assay probe capable of preferentially hybridizing under stringent hybridization conditions to nucleic acid derived from *M. genitalium* over nucleic acid derived from non-*M. genitalium* organisms present in the test sample. In this method, the hybridization assay probe comprises an oligonucleotide having a target binding region, where the base sequence of the target binding region is contained within the base sequence of SEQ ID NO:5, SEQ ID NO:6, SEQ ID NO:7, SEQ ID NO:8, SEQ ID NO:9, SEQ ID NO:10, SEQ ID NO:11 or SEQ ID NO:12. The probes of this method may include at least one additional base sequence region which does not stably bind to nucleic acid derived from *M. genitalium* under stringent hybridization conditions. In another embodiment, this method for determining the presence or amount of *M. genitalium* in a test sample may also include the step of contacting the test sample with one or more helper probes for facilitating hybridization of the probe to the target nucleic acid. The helper probes may be added to the sample before or after the addition of the hybridization assay probe but are preferably provided to the test sample at the same time as the hybridization assay probe.

A further aspect of the present invention relates to a method for amplifying nucleic acid derived from a *Mycoplasma* organism present in a test sample by contacting the test sample under amplification conditions with one or more amplification primers, where each amplification primer comprises an oligonucleotide having a target binding region, where the base sequence of the target binding region has or substantially corresponds to the base sequence of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39 or SEQ ID NO:40. Amplification primers of the present invention do not, however, include an amplification primer comprising an oligonucleotide having a target binding region, where the base sequence of the target binding region has or substantially corresponds to the base sequence of SEQ ID NO:25, SEQ ID NO:26, SEQ ID NO:27, SEQ ID NO:28, SEQ ID NO:37, SEQ ID NO:38, SEQ ID NO:39 or SEQ ID NO:40, except in combination with an amplification primer comprising an oligonucleotide having a target binding region, where the base sequence of the target binding region has or substantially corresponds to the base sequence of SEQ ID NO:21, SEQ ID NO:22, SEQ ID NO:23, SEQ ID NO:24, SEQ ID NO:29, SEQ ID NO:30, SEQ ID NO:31, SEQ ID NO:32, SEQ ID NO:33, SEQ ID NO:34, SEQ ID NO:35 or SEQ ID NO:36. The amplification primers of this embodiment optionally include a 5' sequence which is recognized by an RNA polymerase or which enhances initiation or elongation by an RNA polymerase. When included, a T7 promoter, such as the nucleotide base sequence of SEQ ID NO:41, is preferred. Particular combinations of amplification primers which can be used in this method for amplifying are set forth in the section entitled "Amplification of *Mycoplasma* Ribosomal Nucleic Acid."

In a preferred embodiment, the method for amplifying *Mycoplasma*-derived nucleic acid in a test sample further includes the step of contacting the test sample under stringent hybridization assay conditions with a hybridization assay probe capable of preferentially hybridizing to an amplified *M. pneumoniae* target nucleic acid over nucleic acids from non-*M. pneumoniae* or to an amplified *M. genitalium* target nucleic acid over nucleic acids from non-*M. genitalium* organisms present in the test sample under the stringent conditions. While the test sample is generally contacted with the hybridization assay probe after a sufficient period for amplification has passed, the amplification primers and hybridization assay probe may be added to the sample in any order, especially where the hybridization assay probe is a self-hybridizing probe, such as a molecular torch or a molecular beacon as discussed supra. Molecular beacons may be particularly useful for real-time detection of the target nucleic acid.

The test sample is contacted with a hybridization assay probe so that the presence or amount of *M. pneumoniae* or *M. genitalium* in the test sample can be determined. A preferred hybridization assay probe for use in determining the presence of *M. pneumoniae* in this method comprises an oligonucleotide having a target binding region, where the base sequence of the target binding region consists of or is contained within the base sequence of SEQ ID NO:1, SEQ ID NO:2, SEQ ID NO:3 or SEQ ID NO:4. And for determining the presence of *M. genitalium* in this method, the preferred hybridization assay probe comprises an oligonucleotide having a target binding region, where the base sequence of the target binding region consists of or is contained within the base sequence of SEQ ID NO:5, SEQ ID NO:6, SEQ ID NO:7, SEQ ID NO:8, SEQ ID NO:9, SEQ ID NO:10, SEQ ID NO:11 or SEQ ID NO:12. The probes of these methods may further include labels to facilitate detection in the test sample. But, as above, the hybridization assay probes of these methods do not include additional 5' or 3' base sequence regions which can stably bind to nucleic acid derived from *M. pneumoniae* or *M. genitalium* present in the test sample under stringent hybridization conditions.

In one preferred embodiment, the method for amplifying is carried out with a set of at least two amplification primers for amplifying *Mycoplasma* nucleic acid which includes: (i) a first amplification primer comprising an oligonucleotide having a target binding region, where the base sequence of the target binding region has or substantially corresponds to the base sequence of SEQ ID NO:21, SEQ ID NO:22, SEQ ID NO:23 or SEQ ID NO:24; and (ii) a second amplification primer comprising an oligonucleotide having a target binding region, where the base sequence of the target binding region has or substantially corresponds to the base sequence of SEQ ID NO:29, SEQ ID NO:30, SEQ ID NO:31 or SEQ ID NO:32. Preferably, the base sequence of the target binding region of the first amplification has or substantially corresponds to the base sequence of SEQ ID NO:21, and the base sequence of the target binding region of the second amplification primer has or substantially corresponds to the base sequence of SEQ ID NO:29. In a preferred mode, the second amplification primer further includes a 5' sequence which is recognized by an RNA polymerase or which enhances initiation or elongation by an RNA polymerase.

In another preferred embodiment, a set of at least two amplification primers for amplifying *Mycoplasma* nucleic acid is provided which includes: (i) a first amplification primer comprising an oligonucleotide having a target binding region, where the base sequence of the target binding region has or substantially corresponds to the base sequence of SEQ ID NO:21, SEQ ID NO:22, SEQ ID NO:23 or SEQ ID NO:24; and (ii) a second amplification primer comprising an oligonucleotide having a target binding region, where the base sequence of the target binding region has or substantially corresponds to the base sequence of SEQ ID NO:33, SEQ ID NO:34, SEQ ID NO:35 or SEQ ID NO:36. Preferably, the base sequence of the target binding region of the first amplification primer has or substantially corresponds to the base sequence of SEQ ID NO:21, and the base sequence of the target binding region of the second amplification primer has or substantially corresponds to the base sequence of SEQ ID NO:33. In a preferred mode, the second amplification primer further includes a 5' sequence which is recognized by an RNA polymerase or which enhances initiation or elongation by an RNA polymerase.

In yet another preferred embodiment, a set of at least two amplification primers for amplifying *Mycoplasma* nucleic acid is provided which includes: (i) a first amplification primer comprising an oligonucleotide having a target binding region, where the base sequence of the target binding region has or substantially corresponds to the base sequence of SEQ ID NO:21, SEQ ID NO:22, SEQ ID NO:23 or SEQ ID NO:24; and (ii) a second amplification primer comprising an oligonucleotide having a target binding region, where the base sequence of the target binding region has or substantially corresponds to the base sequence of SEQ ID NO:37, SEQ ID NO:38, SEQ ID NO:39 or SEQ ID NO:40. Preferably, the base sequence of the target binding region of the first amplification primer has or substantially corresponds to the base sequence of SEQ ID NO:21, and the base sequence of the target binding region of the second amplification primer has or substantially corresponds to the base sequence of SEQ ID NO:37. In a preferred mode, the second amplification primer further includes a 5' sequence which is recognized by an RNA polymerase or which enhances initiation or elongation by an RNA polymerase.

In still another preferred embodiment, a set of at least two amplification primers for amplifying *Mycoplasma* nucleic acid is provided which includes: (i) a first amplification primer comprising an oligonucleotide having a target binding region, where the base sequence of the target binding region has or substantially corresponds to the base sequence of SEQ ID NO:25, SEQ ID NO:26, SEQ ID NO:27 or SEQ ID NO:28; and (ii) a second amplification primer comprising an oligonucleotide having a target binding region, where the base sequence of the target binding region has or substantially corresponds to the base sequence of SEQ ID NO:29, SEQ ID NO:30, SEQ ID NO:31 or SEQ ID NO:32. Preferably, the base sequence of the target binding region of the first amplification primer has or substantially corresponds to the base sequence of SEQ ID NO:25, and the base sequence of the target binding region of the second amplification primer has or substantially corresponds to the base sequence of SEQ ID NO:29. In a preferred mode, the second amplification primer further includes a 5' sequence which is recognized by an RNA polymerase or which enhances initiation or elongation by an RNA polymerase.

In a further preferred embodiment, a set of at least two amplification primers for amplifying *Mycoplasma* nucleic acid is provided which includes: (i) a first amplification primer comprising an oligonucleotide having a target binding region, where the base sequence of the target binding region has or substantially corresponds to the base sequence of SEQ ID NO:25, SEQ ID NO:26, SEQ ID NO:27 or SEQ ID NO:28; and (ii) a second amplification primer comprising an oligonucleotide having a target binding region, where the base sequence of the target binding region has or substantially corresponds to the base sequence of SEQ ID NO:33, SEQ ID NO:34, SEQ ID NO:35 or SEQ ID NO:36. Preferably, the base sequence of the target binding region of the first amplification primer has or substantially corresponds to the base sequence of SEQ ID NO:25, and the base sequence of the target binding region of the second amplification primer has or substantially corresponds to the base sequence of SEQ ID NO:33. In a preferred mode, the second amplification primer further includes a 5' sequence which is recognized by an RNA polymerase or which enhances initiation or elongation by an RNA polymerase.

Still another aspect of the present invention relates to a method for immobilizing a target nucleic acid derived from a *Mycoplasma* organism in a test sample which comprises providing to the test sample a capture probe having a target binding region and an immobilized probe binding region under a first set of hybridization conditions permitting the capture probe to stably bind the target nucleic acid, thereby forming a capture probe:target complex, and a second set of hybridization conditions permitting the capture probe to stably bind to an immobilized probe in the test sample, thereby forming an immobilized probe:capture probe:target complex. The first and second sets of hybridization conditions may be the same or different and the capture probe:target complex remains stable under the second set of hybridization conditions. The target binding region of this capture probe comprises a base sequence region which is at least about 85% homologous (preferably at least about 90% homologous, more preferably at least about 95% homologous, and most preferably 100% homologous) to the base sequence of SEQ ID NO:13, SEQ ID NO:14, SEQ ID NO:15, SEQ ID NO:16, SEQ ID NO:17, SEQ ID:18, SEQ ID NO:19 or SEQ ID NO:20. A purifying step preferably follows the immobilizing step to remove one or more components of the test sample which might interfere with or prevent amplification or specific detection of a target sequence contained in the immobilized target nucleic acid. This method for immobilizing and optionally purifying a *Mycoplasma*-derived nucleic may precede any of the methods described above for amplifying and/or detecting the presence of a target nucleic acid derived from *M. pneumoniae* or *M. genitalium*. If a purifying step is included, the target nucleic acid may be indirectly eluted from the immobilized probe or directly eluted from the capture probe of the immobilized probe:capture probe:target complex by altering the sample conditions prior to amplifying or detecting the target sequence.

L. Diagnostic Systems

The present invention also contemplates diagnostic systems in kit form. A diagnostic system of the present invention may include a kit which contains, in an amount sufficient for at least one assay, any of the hybridization assay probes, capture probes and/or amplification primers of the present invention in a packaging material. Typically, the kits will also include instructions recorded in a tangible form (e.g., contained on paper or an electronic medium) for using the packaged probes and/or primers in an amplification and/or detection assay for determining the presence or amount of *M. pneumoniae* or *M. genitalium* in a test sample. In addition, helper probes may be included in the kits.

The various components of the diagnostic systems may be provided in a variety of forms. For example, the required enzymes, the nucleotide triphosphates, the probes and/or primers may be provided as a lyophilized reagent. These lyophilized reagents may be pre-mixed before lyophilization so that when reconstituted they form a complete mixture with the proper ratio of each of the components ready for use in the assay. In addition, the diagnostic systems of the present invention may contain a reconstitution reagent for reconstituting the lyophilized reagents of the kit. In preferred kits for amplifying target nucleic acid derived from *M. pneumoniae* or *M. genitalium*, the enzymes, nucleotide triphosphates and required cofactors for the enzymes are provided as a single lyophilized reagent that, when reconstituted, forms a proper reagent for use in the present amplification methods. In these kits, a lyophilized primer reagent may also be provided. In other preferred kits, lyophilized probe reagents are provided.

Typical packaging materials would include solid matrices such as glass, plastic, paper, foil, micro-particles and the like, capable of holding within fixed limits hybridization assay probes, capture probes, helper probes and/or amplification primers of the present invention. Thus, for example, the packaging materials can include glass vials used to contain sub-milligram (e.g., picogram or nanogram) quantities of a contemplated probe or primer, or they can be microtiter plate wells to which probes or primers of the present invention have been operatively affixed, i.e., linked so as to be capable of participating in an amplification and/or detection method of the present invention.

The instructions will typically indicate the reagents and/or concentrations of reagents and at least one assay method parameter which might be, for example, the relative amounts of reagents to use per amount of sample. In addition, such specifics as maintenance, time periods, temperature and buffer conditions may also be included.

The diagnostic systems of the present invention contemplate kits having any of the hybridization assay probes, capture probes and/or amplification primers described herein, whether provided individually or in one of the preferred combinations described above, for use in amplifying and/or determining the presence or amount of *M. pneumoniae* or *M. genitalium* in a test sample.

M. EXAMPLES

Examples are provided below illustrating different aspects and embodiments of the invention. Skilled artisans will appreciate that these examples are not intended to limit the invention to the specific embodiments described therein.

1. Organism Lysis

Whole cells in the examples below were chemically lysed in a transport medium described below in the "Reagents" section. This transport medium is a detergent-containing buffered solution which, in addition to lysing cells, protects released RNAs by inhibiting the activity of RNAses present in a test sample.

2. Target Capture Assay

A number of the examples which follow incorporate a target capture assay designed to isolate and purify target nucleic acid prior to amplification of a target nucleic acid sequence. The capture probe of these examples included a 5' target binding region having the base sequence of SEQ ID NO:13 and a 3' immobilized probe binding region having a poly dA tail 30 nucleotides in length. The target binding region of the capture probe was designed to bind to a region of the target nucleic acid distinct from the regions bound by the primer, promoter-primer and hybridization assay probe. The solid support of this target capture assay was a Sera-Mag™ MG-CM Carboxylate Modified (Seradyn, Inc.; Indianapolis, Ind.; Cat. No. 24152105-050450), 1 micron, super-paramagnetic particle having a covalently bound oligo $(dT)_{14}$ which was able to bind to the poly dA tail of the capture probe under hybridization conditions. Similar magnetic particles are disclosed by Sutor, "Process for Preparing Magnetically Responsive Microparticles," U.S. Pat. No. 5,648,124. To draw the particles out of suspension and immobilize them along the inner wall of the sample tubes, the tubes were transferred to a magnetic separation rack disclosed by Acosta et al. in U.S. Pat. No. 6,254,826. While the particles were immobized, fluid was aspirated from the tubes and the tubes were washed with the Wash Buffer described below. The wash step was repeated two times before adding the Amplification Reagent and the Enzyme Reagent described below for amplifying the target sequence. Between wash steps, the particles were resuspended in the Wash Buffer. Additional details of the target capture assay are set forth in Example 4 below.

3. Transcription-Mediated Amplification

Amplification of a target sequence in the following examples was a transcription-mediated amplification (TMA) procedure disclosed by, for example, Kacian et al. in U.S. Pat. Nos. 5,399,491 and 5,480,784 and by LEE ET AL., supra, ch. 8. TMA is an isothermal amplification procedure which allows for a greater than one billion-fold increase in copy number of the target sequence using reverse transcriptase and RNA polymerase (see Enzyme Reagents below). A TMA reaction involves converting a single-stranded target sequence to a double-stranded DNA intermediate by reverse transcriptase in the presence of a sense primer and an antisense primer having a 5' RNA polymerase-specific promoter sequence. Included in this DNA intermediate is a double-stranded promoter sequence which is recognized by RNA polymerase and transcribed into hundreds of copies of RNA. Each of these transcribed RNA molecules, in turn, can be converted to a double-stranded DNA intermediate which is used for producing additional RNA. Thus, the TMA reaction proceeds exponentially. The particulars of the TMA reactions used in the following examples are set forth below.

4. Hybridization Assay Probes

Hybridization assay probes specific for *M. pneumoniae* or *M. genitalium* were designed by first sequencing prospective target regions using primers complementary to ribosomal nucleic acid of *M. pneumoniae* (ATCC Accession No. 15531) or from published 16S rRNA sequences, including rRNA of *M. pneumoniae* (GenBank Accession No. M29061) and *M. genitalium* (GenBank Accession No. X77334). To determine variable regions, these sequences were compared to rRNA sequences of phylogenetically near neighbors, including *M. bovis* (GenBank Accession No. U02968), *M. capricolum* (GenBank Accession No. AB000401), *M. collis* (GenBank Accession No. X64727), *M. faucium* (GenBank Accession No. U83663), *M. fermentans* (GenBank Accession No. AF031374) *M. gallisepticum* (GenBank Accession No. M22441), *M. hyopneumoniae* (GenBank Accession No. Y00149), *M. hominis* (GenBank Accession No. M24473), *M. iowae* (GenBank Accession No. M24293), *M. liphophilum* (GenBank Accession No. M24581), *M. muris* (GenBank Accession No. M23939), *M. orale* (GenBank Accession No. M24659), *M. pirum* (GenBank Accession No. M23940), *M. primatum* (GenBank Accession No. AF013997), *M. salivarium* (GenBank Accession No. M24661). Also compared were rRNA sequences of *Acholeplasma laidlawii* (GenBank Accession No. M23932), *Spiroplasma mirum* (GenBank Accession No. M24662) and *Ureaplasma urealyticum* (GenBank Accession No. L08642).

Figure 5:
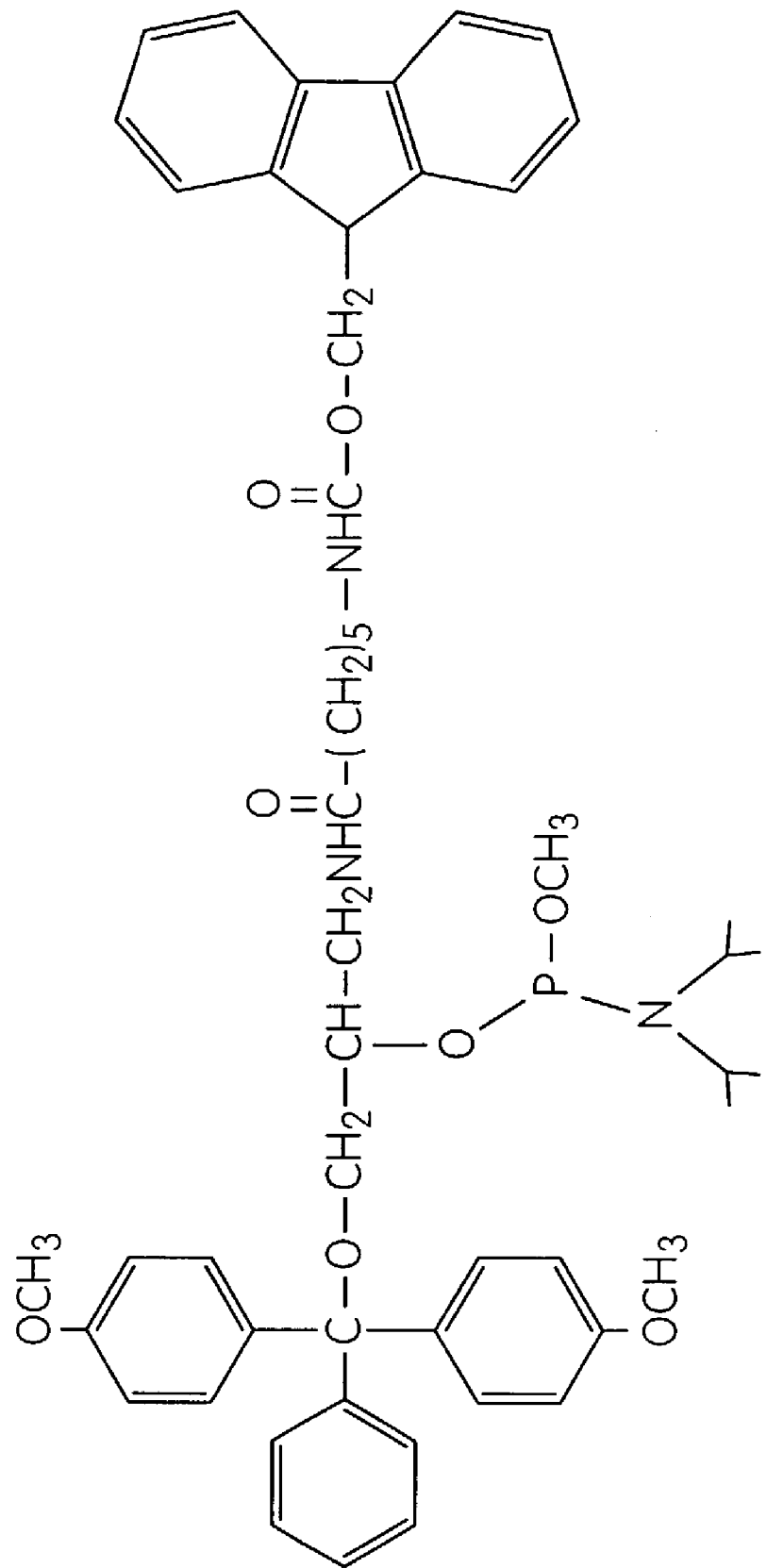
FIG. 5 depicts a linking reagent having an extended aminoalkylcarboxy linker arm which can be used to join a detectable label to an oligonucleotide.

Featured in the examples below are hybridization assay probes having the nucleotide sequences of SEQ ID NO:1, SEQ ID NO:5 and SEQ ID NO:9. All of the hybridization assay probes described below, as well as the capture probes, primers and promoter-primers, were synthesized using standard phosphoramidite chemistry, various methods of which are well known in the art. See, e.g., Caruthers et al., *Methods in Enzymol.*, 154:287 (1987). Synthesis was performed using an Expedite™ 8909 Nucleic Acid Synthesizer (Applied Biosystems; Foster City, Calif.). The hybridization assay probes were also synthesized to include a non-nucleotide linker, as described by Arnold et al. in U.S. Pat. No. 6,031,091 and as shown in FIG. 5, and labeled with a chemiluminescent acridinium ester, as described by Arnold el al. in U.S. Pat. No. 5,185,439. The reactivity and specificity of these probes for nucleic acid derived from *M. pneumoniae* or *M. genitalium* was demonstrated using a single phase homogeneous assay format, the results of which are shown in Table 14 of Example 5 and Tables 18–20 of Example 8 below. This single phase homogenous assay was the hybridization protection assay disclosed by Arnold et al. in U.S. Pat. No. 5,283,174. The results below are given in relative light units (RLU), which is a measure of the photons detected by a luminometer.

5. Reagents

Various reagents are identified in the examples below, which include a hybridization reagent, a selection reagent, an amplification reagent, a reconstitution buffer, an enzyme reagent, an enzyme dilution buffer and an oil reagent. Unless indicated otherwise, the formulations and pH values (where relevant) of these reagents were as follows.

Transport Medium: The "Transport Medium" of the following examples is available as a component of the PACE® 2 Specimen Collection Kit available from Gen-Probe Incorporated under Catalog No. 3275 (male collection kit) or 3300 (female collection kit).

Target Capture Reagent: The "Target Capture Reagent" of the following examples contained 250 mM N-2-hydroxyethelpiperazine-N'-2-ethanesulfonic acid (HEPES), 310 mM LiOH, 1.88 M LiCl, 100 mM EDTA, 2 M LiOH to pH 6.4, and 250 µg/ml 1 micron magnetic particles having oligo(dT)$_{14}$ covalently bound thereto (Seradyn).

Wash Buffer: The "Wash Buffer" of the following examples contained 10 mM HEPES, 6.5 mM NaOH, 1 mM EDTA, 0.3% (v/v) ethyl alcohol, absolute, 0.02% (w/v) methyl paraben, 0.01% (w/v) propyl paraben, 150 mM NaCl, 0.1% (w/v) lauryl sulfate, sodium (SDS), and 4 M NaOH to pH 7.5.

Hybridization Reagent: The 2×"Hybridization Reagent" of the following examples contained 100 mM succinic acid, 2% (w/v) LLS, 100 mM LiOH, 15 mM aldrithiol-2, 1.2 M LiCl, 20 mM EDTA, 3% (v/v) ethyl alcohol, absolute, and 2 M LiOH to pH 4.7.

Selection Reagent: The "Selection Reagent" of the following examples contained 600 mM boric acid, 240 mM NaOH, 1% (v/v) TRITON® X-100, and 4 mM NaOH to pH 8.5.

Amplification Reagent: The "Amplification Reagent" of the following examples was a lyophilized formulation which contained 4 mM each of rATP, rCTP, rGTP and rUTP, 1 mM each of dATP, dCTP, dGTP and dTTP, 40 mM trizma base, 25 mM $MgCl_2$, 17.5 mM KCl, 5% (w/v) polyvinylpyrrolidone, and 1 M NaOH and 6 M HCl to pH 7.5. The Amplification Reagent was reconstituted in 2.2 ml purified water.

Enzyme Reagent: The "Enzyme Reagent" of the following examples was a lyophilized formulation which contained 125 mM N-acetyl-L-cysteine (NALC), 0.2% (v/v) TRITON® X-102, 20 mM HEPES, 0.1 mM EDTA, 0.1 mM zinc acetate, 0.2 M trehalose, 4M NaOH to pH 7.5, 0.25 MU/ml Moloney murine leukemia virus ("MMLV") reverse transcriptase, and 0.20 MU/ml T7 RNA polymerase. (One "unit" of activity is defined as the synthesis and release of 5.75 fmol cDNA in 15 minutes at 37° C. for MMLV reverse transcriptase, and for T7 RNA polymerase, one "unit" of activity is defined as the production of 5.0 fmol RNA transcript in 20 minutes at 37° C.) The Enzyme Reagent was reconstituted with 1.5 ml Enzyme Diluent Reagent.

Enzyme Diluent Reagent: The "Enzyme Diluent Reagent" of the following examples contained 140 mM HEPES, 1 mM EDTA, 10% (v/v) TRITON® X-102, 70 mM KCl, 20% (v/v) glycerol, and 6 M HCl to pH 8.0.

Detection Reagents: The "Detection Reagents" of the following examples comprised Detect Reagent I, which contained 0.1% (v/v) $H_2O_2$, and 1 mM nitric acid, and Detect Reagent II, which contained 1N NaOH and a surfactant component. These Detection Reagents are available from Gen-Probe Incorporated under Catalog No. 1791 and are sold as the GEN-PROBE® Detection Reagent Kit for use with all LEADER® analyzers.

Oil Reagent: The "Oil Reagent" of the following examples was a mineral oil.

Example 1

*M. pneumoniae* Probes Exhibiting Improved Differential Hydrolysis Properties This example illustrates hybridization assay probes for *M. pneumoniae* 16S rRNA which appear to exhibit improved differential hydrolysis properties over a prior art probe disclosed by Hammond et al., "Nucleic Acid Hybridization Assay Probes, Helper Probes and Amplification Oligonucleotides Targeted to *M. pneumoniae* Nucleic Acid," U.S. Pat. No. 5,656,427. Hybridization assay probes of the present invention which were used in this example had the nucleotide sequence of SEQ ID NO:1 and were synthesized, as described above, to include a non-nucleotide linker positioned either between nucleotides 14 and 15 ("Probe 1") or between nucleotides 16 and 17 ("Probe 2"), when reading 5' to 3'. The Hammond probe ("Probe 3") had the nucleotide base sequence of SEQ ID NO:42 gcattggaaactattaatctagagtgtg and were synthesized, as described above, to include a non-nucleotide linker between nucleotides 17 and 18 (reading 5' to 3').

*M. pneumoniae* 16S rRNA transcript (antisense) was provided to three sets of two 12×75 mm polypropylene tubes (Gen-Probe Incorporated; Cat. No. 2440) at concentrations of 0.0 ng ("negative control"), 0.2 ng and 2.0 ng, respectively, for each probe tested. These concentrations were derived from a stock solution containing 0.02 ng transcript/µl water. (The transcript in this experiment was a 1453 base pair clone of a 16S rRNA sequence isolated from *M. pneumonia* obtained from the American Type Culture Collection of Manassas, Va. as ATCC No. 15531.) Each tube was also provided with 100 fmol probe and 200 µl 1× Hybridization Reagent and mixed by hand. The stock solutions of probe contained 100 fmol probe/µl 1× Hybridization Reagent.

To facilitate hybridization, the tubes were incubated at 60° C. in a circulating water bath (Precision Scientific, Inc., Winchester, Va.; Model 260; Cat. No. 51221035) for 30 minutes. Following hybridization, 300 µl Selection Reagent was added to each tube, and the tubes were mixed by hand before being incubated at 60° C. in the circulating water bath for 10 minutes to hydrolyze acridinium ester labels associated with unhybridized probe. Samples were cooled at room temperature for 5 minutes prior to being analyzed in a LEADER® 450hc luminometer (Gen-Probe Incorporated) equipped with automatic injection of the Detection Regents for detecting signal from annealed hybridization assay probes. The results are set forth in Table 1 below, where a net RLU value greater than 10,000 RLU is considered to be a positive result, and a net RLU value less than 10,000 RLU is considered to be a negative result. Net RLU values are based on the average RLU value of each sample set minus the average RLU value for the negative control set (i.e., background signal).

TABLE 1

Hybridization of Probes to Varying Concentrations of *M. pneumoniae* Target RNA

| Hybridization Assay Probe | Transcript Concentration | Total RLU | Average RLU | Average Net RLU |
|---|---|---|---|---|
| Probe 1 | Negative Control | 1,188 1,156 | 1,172 | 0 |
|  | 0.2 ng | 16,583 16,802 | 16,693 | 15,521 |
|  | 2.0 ng | 166,868 166,505 | 166,687 | 165,515 |
| Probe 2 | Negative Control | 1,290 1,279 | 1,285 | 0 |
|  | 0.2 ng | 12,891 13,264 | 13,078 | 11,793 |
|  | 2.0 ng | 127,422 126,565 | 126,994 | 125,709 |
| Probe 3 | Negative Control | 1,182 1,154 | 1,168 | 0 |
|  | 0.2 ng | 3,303 2,980 | 3,142 | 1,974 |

TABLE 1-continued

Hybridization of Probes to Varying Concentrations of *M. pneumoniae* Target RNA

| Hybridization Assay Probe | Transcript Concentration | Total RLU | Average RLU | Average Net RLU |
|---|---|---|---|---|
|  | 2.0 ng | 18,329 22,058 | 20,194 | 19,026 |

In this experiment, the significantly higher average net RLU values for Probes 1 and 2 at target concentrations of 0.2 ng and 2.0 ng, as compared to Probe 3, suggested that Probes 1 and 2 of the present invention exhibit improved differential hydrolysis properties in the presence of a target nucleic acid under identical hybridization assay conditions. This conclusion was confirmed for Probe 1 in separate experiments set forth in Example 2.

Example 2

Comparison of Differential Hydrolysis Ratios for *M. pneumoniae* Probes

This example compares the differential hydrolysis ratios of two Hammond probes and two probes according to the present invention. The Hammond probes were Probe 3 of Example 1 above and a probe which shared the nucleotide sequence Probe 3 but included a non-nucleotide linker positioned between nucleotides 15 and 16 ("Probe 4"), when reading 5' to 3'. The two probes according to the present invention were Probes 1 and 2 of Example 1 above. While Probes 1 and 2 and Probes 3 and 4 were studied in separate experiments, the descriptions and results of these separate experiments are presented together in this example to facilitate comparisons. All four probes used were labeled with a chemiluminescent acridinium ester, as described above in the section entitled "Preparation of Oligonucleotides."

Probes 3 and 4 were studied in the first experiment. In this experiment, four 12×75 mm polypropylene tubes (Gen-Probe Incorporated; Cat. No. 2440) were set up to include the following amounts and concentrations of probe, target and Hyb/Amp Reagent:

| Tube 1: | 5 µl Probe 4 (0.5 pmol) |
|---|---|
|  | 46 µl Target (5 pmol) |
|  | 49 µl 1X Hyb/Amp Reagent |
| Tube 2: | 5 µl Probe 3 (0.5 pmol) |
|  | 46 µl Target (5 pmol) |
|  | 49 µl 1X Hyb/Amp Reagent |
| Tube 3: | 5 µl Probe 4 (0.5 pmol) |
|  | 0 µl Target |
|  | 95 µl 1X Hyb/Amp Reagent |
| Tube 4: | 5 µl Probe 3 (0.5 pmol) |
|  | 0 µl Target |
|  | 95 µl 1X Hyb/Amp Reagent |

The target was the same in each tube and was an RNA sequence generated by transcription-mediated amplification to contain a sequence complementary to the sequences of the probes. In each case, the "Hyb/Amp Reagent" provided to the tubes contained a 4:2:1:1 ratio of Hybridization Reagent to water to Amplification Reagent to Enzyme Reagent.

The contents of each tube were diluted with 900 µl Hyb/Amp Reagent and mixed by pipetting. A 1 µl aliquot was then taken from each of these dilutions and combined with 100 µl Hyb/Amp Reagent in a 12×75 mm polypropylene tube (Gen-Probe Incorporated; Cat. No. 2440), followed by incubation in a water bath (Precision Scientific; Cat. No. 51221035) at 60° C. for 40 minutes to facilitate binding of probe (if present) to target. After incubating, signal from the tubes was measured in relative light units (RLUs) in a LEADER® 50 luminometer (Gen-Probe Incorporated; Cat. No. 3100). Based on these RLU values, 1 ml dilutions were prepared in 12×75 mm polypropylene tubes (Gen-Probe Incorporated; Cat. No. 2440) to obtain 200,000 to 400,000 RLU per 100 µl in each of the dilutions. This RLU range was chosen to be within the linear range of the luminometer. The dilutions were prepared using Hyb/Amp Reagent.

Each dilution received 300 µl Selection Reagent and the tubes were mixed by hand. Dilutions of Tubes 1 and 2 ("Hybrid") were separately incubated at 60° C. for 0, 0.5, 1, 2, 3 and 4 minutes, and dilutions of Tubes 3 and 4 ("Control") were separately incubated at 60° C. for 0, 0.5, 1, 2, 3, 4, 5 and 10 minutes. The incubations were performed in a water bath (Precision Scientific; Cat. No. 51221035). Following incubation, the dilutions were chilled on ice for 1 minute and then placed in a water bath at room temperature for 1 minute before signal from the tubes was read on a LEADER® 50 luminometer. For the 0 time points, Selection Reagent was added to the dilutions at room temperature and the dilutions were mixed by hand immediately prior to reading. A blank tube containing 100 µl Hyb/Amp reagent was also prepared, read on the luminometer and then subtracted from the RLU value for each time point. The value for the blank tube was 540 RLU. The results of these hydrolysis reactions are set forth in Tables 2–5 below.

TABLE 2

Probe 4 (Control): Signal from Dilutions Containing
M. pneumoniae Probe and Target RNA Over Time
Probe 4 (Control)

| Time (minutes) | RLU | Percent of Time 0 |
| --- | --- | --- |
| 0 | 134,594 | 100.00 |
| 0.5 | 22,225 | 16.11 |
| 1 | 6,457 | 4.40 |
| 2 | 1,033 | 0.37 |
| 3 | 635 | 0.07 |
| 4 | 730 | 0.14 |
| 5 | 548 | 0.00 |
| 10 | 529 | 0.00 |

TABLE 3

Probe 4 (Hybrid): Signal from Dilutions Containing
M. pneumoniae Probe and Target RNA Over Time
Probe 4 (Hybrid)

| Time (minutes) | RLU | Percent of Time 0 |
| --- | --- | --- |
| 0 | 159,272 | 100.00 |
| 0.5 | 121,064 | 75.67 |
| 1 | 114,720 | 71.69 |
| 2 | 90,230 | 56.31 |
| 3 | 69,627 | 43.38 |
| 4 | 51,150 | 31.78 |

TABLE 4

Probe 3 (Control): Signal from Dilutions Containing
M. pneumoniae Probe and Target RNA Over Time
Probe 3 (Control)

| Time (minutes) | RLU | Percent of Time 0 |
| --- | --- | --- |
| 0 | 144,345 | 100.00 |
| 0.5 | 17,984 | 12.08 |
| 1 | 4,363 | 2.65 |
| 2 | 740 | 0.14 |
| 3 | 626 | 0.06 |
| 4 | 562 | 0.02 |
| 5 | 606 | 0.00 |
| 10 | 533 | 0.00 |

TABLE 5

Probe 3 (Hybrid): Signal from Dilutions Containing
M. pneumoniae Probe and Target RNA Over Time
Probe 3 (Hybrid)

| Time (minutes) | RLU | Percent of Time 0 |
| --- | --- | --- |
| 0 | 196,019 | 100.00 |
| 0.5 | 153,558 | 78.06 |
| 1 | 141,445 | 71.88 |
| 2 | 103,776 | 52.66 |
| 3 | 58,772 | 29.71 |
| 4 | 34,728 | 17.44 |

Figure 2:
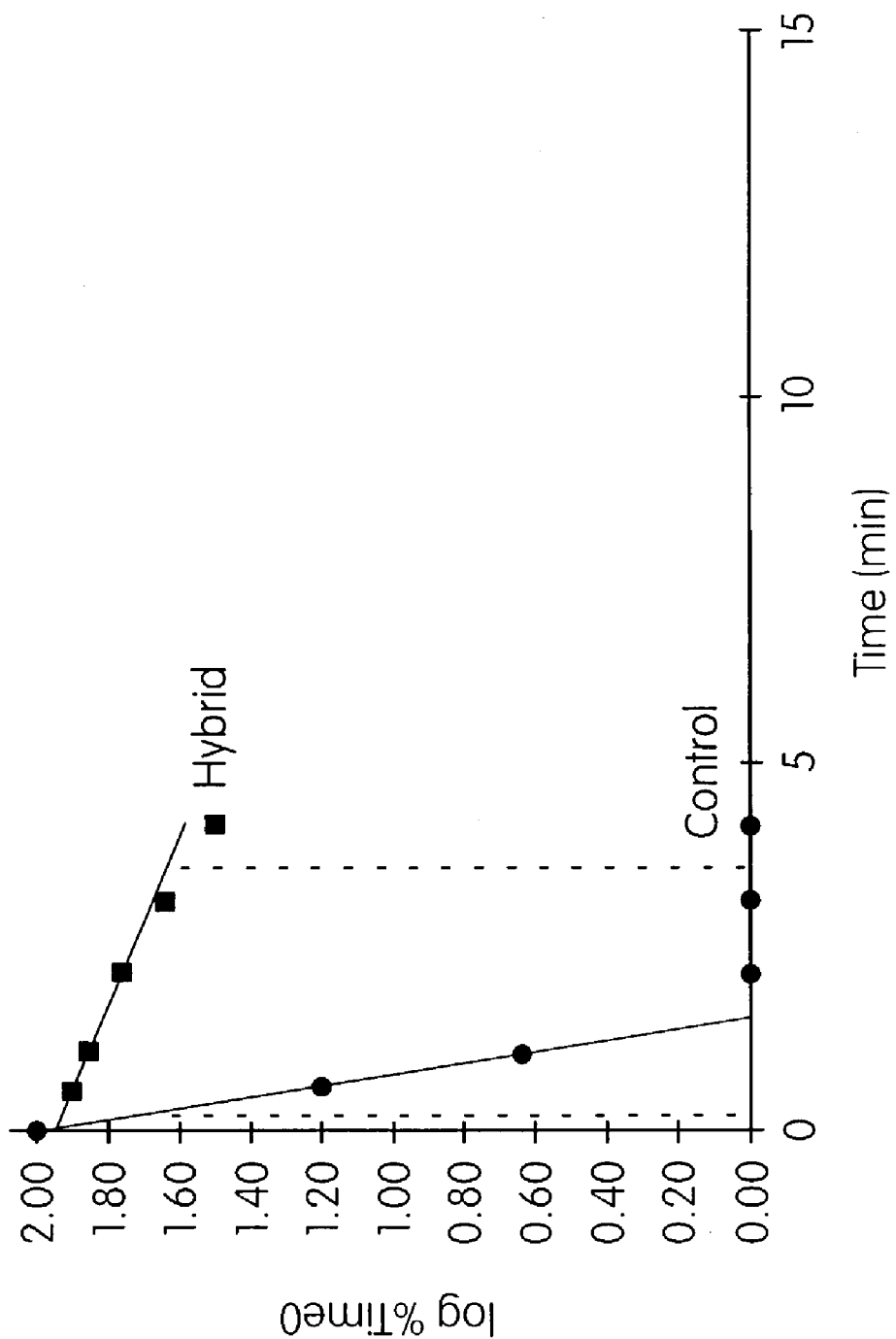

The data set forth in Tables 2–5 was used to generate graphs plotting "log % Time0" on the y-axis versus "Time (min)" on the x-axis for the hybrids (■) and the controls (●), as shown in FIGS. 1 and 2. From these graphs, slopes and $t_{1/2}$ values (time required to hydrolyze 50% of the probe associated acridinium ester label) were determined for the controls and hybrids using standard linear-regression analysis and compared to determine the differential hydrolysis (DH) ratios for Probes 3 and 4. Since DH ratios are a measure of $t_{1/2}$ (hybrid)/$t_{1/2}$ (control), probes having higher DH ratios are more desirable. This is because DH ratios provide an indication as to how well labels associated with particular probes will be protected against hydrolysis when those probes are hybridized to target sequences as opposed to when they remain free in solution. Thus, higher DH ratios translate to mean better sensitivity and more accurate quantification of target sequences. The $t_{1/2}$ values and DH ratios determined from this first experiment are set forth in Table 6 below.

TABLE 6

Differential Hydrolysis Ratios for M. pneumoniae Probes

|  | Probe 4 | Probe 3 |
| --- | --- | --- |
| $t_{1/2}$ (Control) | 0.22 | 0.19 |
| $t_{1/2}$ (Hybrid) | 3.41 | 2.57 |
| DH Ratio | 15.37 | 13.48 |

Probes 1 and 2 were studied in the second experiment. In this experiment, four 12×75 mm polypropylene tubes (Gen-Probe Incorporated; Cat. No. 2440) were set up to include the following amounts and concentrations of probe, target and Hyb/Amp Reagent:

| | |
|---|---|
| Tube 5: | 10 μl Probe 1 (1 pmol) |
| | 7.3 μl Target (20 pmol) |
| | 82.7 μl Hyb/Amp Reagent |
| Tube 6: | 10 μl Probe 2 (1 pmol) |
| | 7.3 μl Target (20 pmol) |
| | 82.7 μl Hyb/Amp Reagent |
| Tube 7: | 10 μl Probe 1 (1 pmol) |
| | 0 μl Target |
| | 90 μl Hyb/Amp Reagent |
| Tube 8: | 10 μl Probe 2 (1 pmol) |
| | 0 μl Target |
| | 90 μl Hyb/Amp Reagent |

The protocol for this experiment was identical to that followed with Probes 3 and 4 above, except for the following particulars: (i) dilutions were prepared in 2 ml Hyb/Amp Reagent instead of 1 ml; (ii) the RLU count for each dilution was about 700,000 per 100 μl instead of 200,000 to 400,000 per 100 μl; and (iii) incubation times in the presence of Selection Reagent for dilutions of Tubes 5 and 6 ("Hybrid") were 0, 5, 10, 15, 20 and 30 minutes as opposed to 0, 0.5, 1, 2, 3 and 4 minutes for the dilutions of Tubes 1 and 2. The results of the second experiment are set forth in Tables 7–10 below.

TABLE 7

Probe 1 (Control): Signal from Dilutions Containing
M. pneumoniae Probe and Target RNA Over Time
Probe 1 (Control)

| Time (minutes) | RLU | Percent of Time 0 |
|---|---|---|
| 0 | 369,932 | 100.00 |
| 0.5 | 186,548 | 50.28 |
| 1 | 111,807 | 30.07 |
| 2 | 32,110 | 8.53 |
| 3 | 7,804 | 1.95 |
| 4 | 2,576 | 0.54 |
| 5 | 1,508 | 0.00 |
| 10 | 498 | 0.00 |

TABLE 8

Probe 1 (Hybrid): Signal from Dilutions Containing
M. pneumoniae Probe and Target RNA Over Time
Probe 1 (Hybrid)

| Time (minutes) | RLU | Percent of Time 0 |
|---|---|---|
| 0 | 464,327.5 | 100.00 |
| 5 | 340,574 | 73.22 |
| 10 | 276,077 | 59.33 |
| 15 | 230,603 | 49.54 |
| 20 | 196,265 | 42.15 |
| 30 | 165,079 | 35.43 |

TABLE 9

Probe 2 (Control): Signal from Dilutions Containing
M. pneumoniae Probe and Target RNA Over Time
Probe 2 (Control)

| Time (minutes) | RLU | Percent of Time 0 |
|---|---|---|
| 0 | 446,172.5 | 100.00 |
| 0.5 | 267,804 | 59.89 |
| 1 | 153,195 | 34.21 |
| 2 | 53,945 | 11.96 |
| 3 | 11,645 | 2.48 |
| 4 | 3,946 | 0.76 |
| 5 | 1,612 | 0.00 |
| 10 | 554 | 0.00 |

TABLE 10

Probe 2 (Hybrid): Signal from Dilutions Containing
M. pneumoniae Probe and Target RNA Over Time
Probe 2 (Hybrid)

| Time (minutes) | RLU | Percent of Time 0 |
|---|---|---|
| 0 | 616,157.5 | 100.00 |
| 5 | 348,843 | 56.52 |
| 10 | 237,647 | 38.48 |
| 15 | 139,097 | 22.48 |
| 20 | 82,667 | 13.32 |
| 30 | 39,559 | 6.33 |

Figure 3:
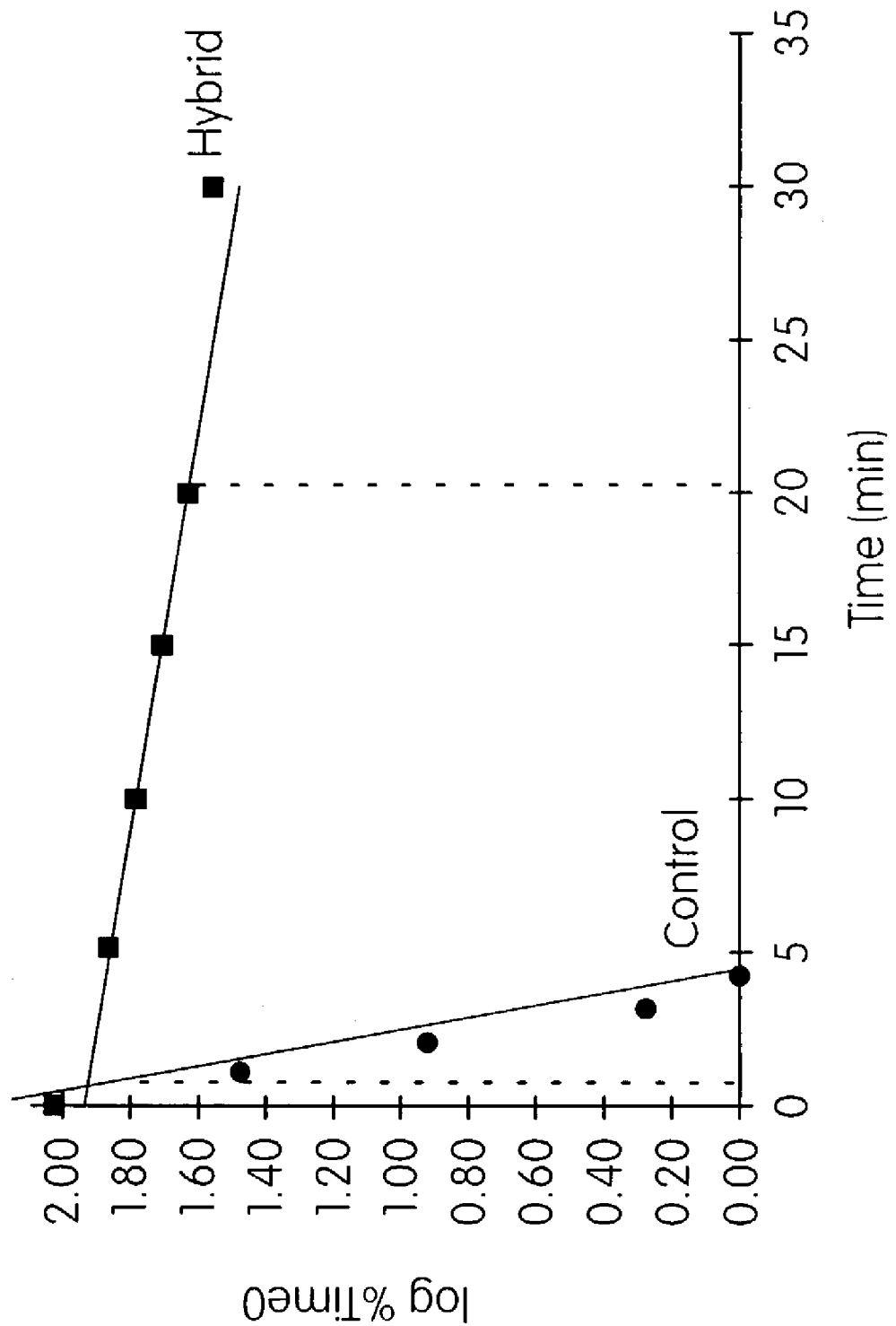
FIGS. 3 and 4 are graphs which were used to determine the differential hydrolysis ratios of two probes according to the present invention. Using the time and signal data set forth in Tables 7–10 of Example 2 infra, these graphs plot the data for hybrids (■) and controls (●) as the log of the percentage of time zero chemiluminescence on the y-axis versus time in minutes on the x-axis. Slopes and associated $t_{1/2}$ values were determined for the controls and hybrids of each probe using standard linear-regression analysis. Based on the $t_{1/2}$ values determined from these graphs, the differential hydrolysis ratio for each probe was calculated by comparing the $t_{1/2}$ value of the hybrid to the $t_{1/2}$ value of the control.
Figure 4:
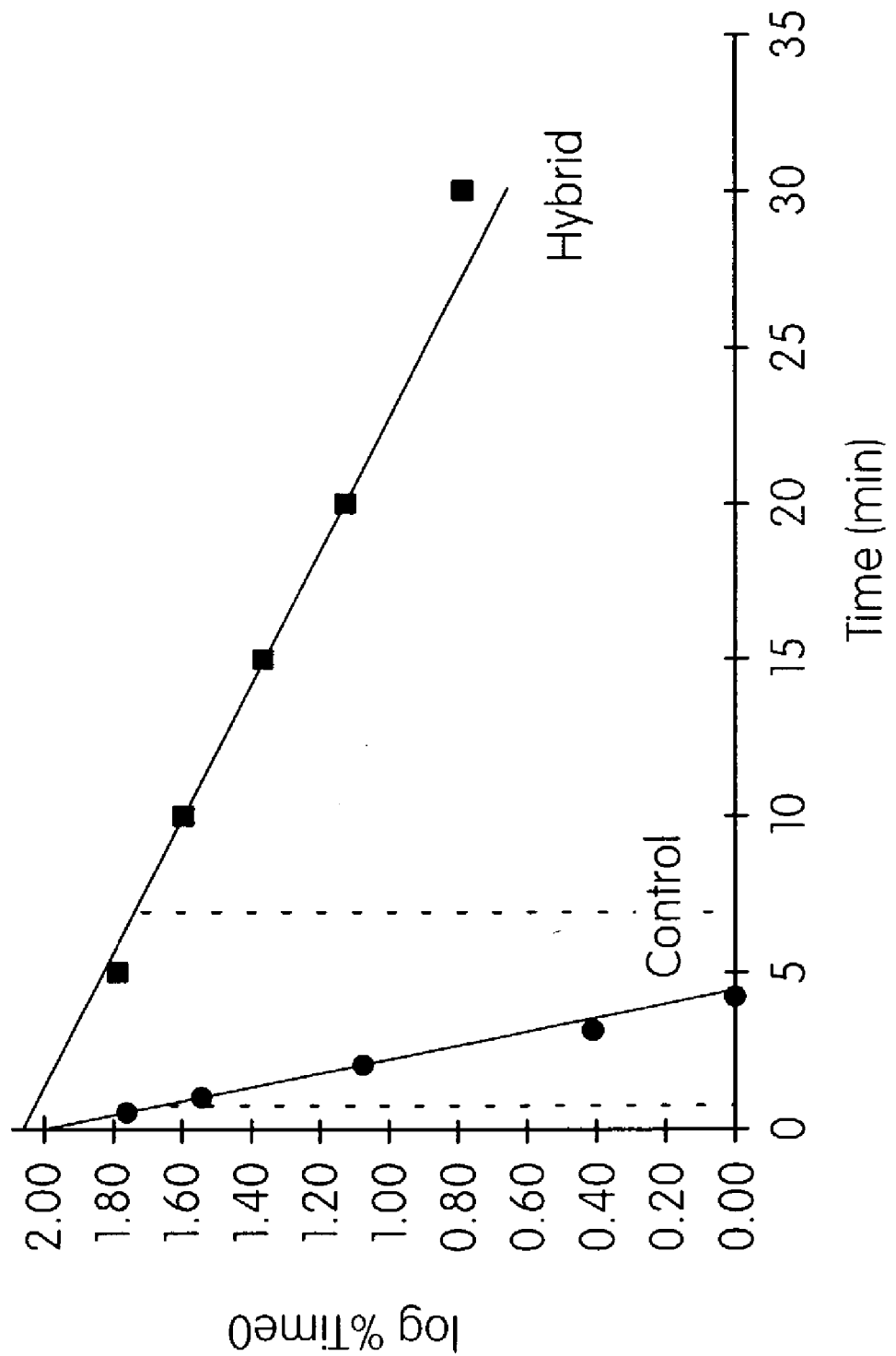

The data of Tables 7–10 was also used to generate graphs plotting "log % Time0" on the y-axis versus "Time (min)" on the x-axis for the hybrids (■) and the controls (■), as shown in FIGS. 3 and 4. From these graphs, $t_{1/2}$ values were determined for the controls and hybrids using standard linear-regression analysis and compared to determine the DH ratios for Probes 1 and 2. The $t_{1/2}$ values and DH ratios determined from this second experiment are set forth in Table 11 below.

TABLE 11

Differential Hydrolysis Ratios for M. pneumoniae Probes

| | Probe 1 | Probe 2 |
|---|---|---|
| $t_{1/2}$ (Control) | 0.58 | 0.65 |
| $t_{1/2}$ (Hybrid) | 20.26 | 6.54 |
| DH Ratio | 35.13 | 10.12 |

A comparison of the DH ratios of Tables 6 and 11 demonstrates that Probe 1 is superior to Probes 3 and 4, having a DH ratio more than twice that of either these probes. In separate experiments, Probes 3 and 4 were determined to have melting temperatures ($T_m$) only slightly higher than those of Probes 1 and 2 (an average $T_m$ of 67.5° C. for Probes 3 and 4 as compared to an average $T_m$ of 64° C. for Probes 1 and 2). Thus, Probe 1 would be expected to have comparable specificity to Probes 3 and 4 and greater sensitivity than either Probe 3 or 4 under similar conditions.

Example 3

Amplification and Detection of *M. pneumoniae* Nucleic Acid

This example illustrates the amplification of a target sequence of *M. pneumoniae* nucleic acid and detection of amplified rRNA using a hybridization assay probe specific for *M. pneumoniae*-derived nucleic acid. In particular, a *M. pneumoniae* hybridization assay probe having the base sequence of SEQ ID NO:42 was synthesized, as described above, to include a non-nucleotide linker positioned between nucleotides 15 and 16, when reading 5' to 3'. This hybridization assay probe was of the same sense as the *M. pneumoniae* target rRNA and was used to detect product of six different transcription-mediated amplifications.

Transcripts were generated from 16S rRNA sequences obtained from *M. pneumoniae* (ATCC Accession No. 15531) and separately amplified using different sets of primers and promoter-primers. The primer/promoter-primer combinations used in these amplification reactions were as follows: (i) a promoter-primer having a 5' end promoter base sequence of SEQ ID NO:41 and a 3' end sense template-specific base sequence of SEQ ID NO:29, and a primer having an antisense template-specific base sequence of SEQ ID NO:21 ("Set 1"); (ii) a promoter-primer having a 5' end promoter base sequence of SEQ ID NO:41 and a 3' end sense template-specific base sequence of SEQ ID NO:33, and a primer having an antisense template-specific base sequence of SEQ ID NO:21 ("Set 2"); (iii) a promoter-primer having a 5' end promoter base sequence of SEQ ID NO:41 and a 3' end sense template-specific base sequence of SEQ ID NO:37, and a primer having an antisense template-specific base sequence of SEQ ID NO:21 ("Set 3"); (iv) a promoter-primer having a 5' end promoter base sequence of SEQ ID NO:41 and a 3' end sense template-specific base sequence of SEQ ID NO:29, and a primer having an antisense template-specific base sequence of SEQ ID NO:25 ("Set 4"); (v) a promoter-primer having a 5' end promoter base sequence of SEQ ID NO:41 and a 3' end sense template-specific base sequence of SEQ ID NO:33, and a primer having an antisense template-specific base sequence of SEQ ID NO:25 ("Set 5"); and (vi) a promoter-primer having a 5' end promoter base sequence of SEQ ID NO:41 and a 3' end sense template-specific base sequence of SEQ ID NO:37, and a primer having an antisense template-specific base sequence of SEQ ID NO:25 ("Set 6").

A total of six stock solution tubes were prepared to include 375 µl Amplification Reagent reconstituted in 750 µl water, 418 µl water, 15 µl promoter-primer from a stock solution at 15 pmol/µl water, and 15 µl primer from a stock solution at 15 pmol/µl water. Each of the six stock solution tubes contained a different primer/promoter-primer combination, as set forth above. An aliquot of 65 µl from each of the six stock solution tubes was then added to each of twelve 12×75 mm polypropylene tubes (Gen-Probe Incorporated; Cat. No. 2440), and duplicate sets of these tubes received a 10 µl solution containing 0 copies ("negative control"), $10^2$ copies, $10^3$ copies, $10^4$ copies, $10^5$ copies or $10^6$ copies of the transcript. Each sample received 200 µl Oil Reagent and was incubated at 60° C. in a water bath (Precision Scientific; Cat. No. 51221035) for 5 minutes. The samples were then transferred to a circulating water bath (Lauda Dr. R. Wobser GmbH & Co. KG, Lauda-Koenigshofen, Germany; Model No. M20-S) and incubated for 5 minutes at 42° C. to denature the transcript before adding 25 µl of reconstituted Enzyme Reagent to each tube. Following a 60 minute incubation at 42° C. in the circulating water bath, 100 µl probe mix (obtained from a stock solution containing 7.5 ml 2× Hybridization Reagent and 75 µl hybridization assay probe at a concentration of 100 fmol/µl 1× Hybridization Reagent) was added to each tube, and the tubes were vortexed before being incubated for 30 minutes in the 60° C. water bath to permit hybridization of probe to amplified target sequences. At the end of this incubation, 300 µl Selection Reagent was added to each tube, and the tubes were vortexed before being incubated in the 60° C. water bath for 8 minutes to hydrolyze acridinium ester labels associated with unhybridized probe. Samples were cooled on ice for 1 minute prior to being analyzed in a LEADER® 450hc luminometer (Gen-Probe Incorporated) equipped with automatic injection of the Detection Regents. Sample sets with an average RLU value greater than 10-fold the average RLU value for the negative control (0 transcript copies) indicated transcript amplification, and sample sets with an average RLU value less than 10-fold the average RLU for the negative control indicated no transcript amplification. The results are set forth in Table 12 below.

TABLE 12

Primer Sets for Amplifying Varying Concentrations of *M. pneumoniae* Target RNA

| Primer Set | Transcript Concentration | Total RLU | Average RLU | Average Net RLU |
|---|---|---|---|---|
| Set 1 | Negative Control | 13,412<br>11,793 | 12,603 | 0 |
| | 100 Copies | 804,451<br>879,811 | 842,131 | 829,529 |
| | 1,000 Copies | 2,421,074<br>2,885,020 | 2,653,047 | 2,640,445 |
| | 10,000 Copies | 3,536,585<br>2,196,561 | 2,866,573 | 2,853,971 |
| | 100,000 Copies | 2,383,740<br>2,588,618 | 2,486,179 | 2,473,577 |
| | 1,000,000 Copies | 3,431,666<br>3,718,718 | 3,575,192 | 3,562,590 |
| Set 2 | Negative Control | 11,090<br>2,125 | 6,608 | 0 |
| | 100 Copies | 809,470<br>38,729 | 424,100 | 417,492 |
| | 1,000 Copies | 559,898<br>1,907,529 | 1,233,714 | 1,227,106 |
| | 10,000 Copies | 3,174,234<br>621,447 | 1,897,841 | 1,891,233 |
| | 100,000 Copies | 953,316<br>2,315,089 | 1,634,203 | 1,627,595 |
| | 1,000,000 Copies | 2,764,490<br>3,378,714 | 3,071,602 | 3,064,995 |
| Set 3 | Negative Control | 3,464<br>16,415 | 9,940 | 0 |
| | 100 Copies | 844,720<br>1,592,898 | 1,218,809 | 1,208,870 |
| | 1,000 Copies | 2,158,914<br>300,296 | 1,229,605 | 1,219,666 |
| | 10,000 Copies | 1,313,685<br>3,929,644 | 2,621,665 | 2,611,725 |
| | 100,000 Copies | 3,487,046<br>3,439,642 | 3,463,344 | 3,453,405 |
| | 1,000,000 Copies | 3,602,755<br>3,583,278 | 4,593,017 | 3,583,077 |
| Set 4 | Negative Control | 12,307<br>23,476 | 17,892 | 0 |
| | 100 Copies | 1,745,788<br>1,699,668 | 1,722,728 | 1,704,837 |
| | 1,000 Copies | 2,921,938<br>3,383,781 | 3,152,860 | 3,134,968 |
| | 10,000 Copies | 2,461,516<br>3,790,080 | 3,125,798 | 3,107,907 |
| | 100,000 Copies | 1,847,467<br>3,191,689 | 2,519,578 | 2,501,687 |

TABLE 12-continued

Primer Sets for Amplifying Varying Concentrations of
M. pneumoniae Target RNA

| Primer Set | Transcript Concentration | Total RLU | Average RLU | Average Net RLU |
|---|---|---|---|---|
|  | 1,000,000 Copies | 3,616,460 3,512,931 | 3,564,696 | 3,546,804 |
| Set 5 | Negative Control | 8,984 6,265 | 7,625 | 0 |
|  | 100 Copies | 506,043 416,427 | 461,235 | 453,611 |
|  | 1,000 Copies | 869,611 1,289,404 | 1,079,508 | 1,071,883 |
|  | 10,000 Copies | 1,410,230 2,563,113 | 1,986,672 | 1,979,047 |
|  | 100,000 Copies | 1,524,770 1,381,898 | 1,453,334 | 1,445,710 |
|  | 1,000,000 Copies | 3,517,281 1,839,223 | 2,678,252 | 2,670,628 |
| Set 6 | Negative Control | 3,900 8,688 | 6,294 | 0 |
|  | 100 Copies | 158,573 392,904 | 275,739 | 269,445 |
|  | 1,000 Copies | 877,290 1,186,305 | 1,031,798 | 1,025,504 |
|  | 10,000 Copies | 1,692,019 2,107,331 | 1,899,675 | 1,893,381 |
|  | 100,000 Copies | 103,007 1,854,974 | 978,991 | 972,697 |
|  | 1,000,000 Copies | 1,629,090 2,538,216 | 2,083,653 | 2,077,359 |

The results of this experiment demonstrate that each of the primer/promoter-primer combinations tested was effective in amplifying the target sequence contained in the transcript. Of these, the primer/promoter-primer combinations of Sets 1 and 4 showed the greatest sensitivity with the least variability in amplifying the target sequence.

Example 4

Amplification and Detection of M. pneumoniae Nucleic Acid Using a Target Capture System This example illustrates the immobilization and amplification of a target sequence of M. pneumoniae nucleic acid, followed by detection of amplified rRNA using a hybridization assay probe specific for M. pneumoniae-derived nucleic acid. In particular, a M. pneumoniae hybridization assay probe having the base sequence of SEQ ID NO:1 was synthesized, as described above, to include a non-nucleotide linker positioned between nucleotides 14 and 15, when reading 5' to 3'. This hybridization assay probe was of the same sense as the M. pneumoniae target rRNA and was used to detect product of a transcription-mediated amplification.

Fifteen 12×75 mm polypropylene tubes (Gen-Probe Incorporated; Cat. No. 2440) were set up and each was provided with 400 µl Transport Medium and 200 µl Target Capture Reagent, the Target Capture Reagent containing the capture probe described above in the section entitled "Target Capture Assay" at a concentration of 25 pmol/ml. Each member of a set of five tubes was provided with a 10 µl solution of water containing 0 ("negative control"), 200 or 2,000 copies of a transcript generated from 16S rRNA sequences obtained from M. pneumoniae (ATCC Accession No. 15531) and then mixed by hand. The tubes were incubated at 60° C. in a water bath (Precision Scientific; Cat. No. 51221035) for 10 minutes and then for 5 minutes at room temperature. The tubes were then transferred to a magnetic separation rack disclosed by Acosta et al. in U.S. Pat. No. 6,254,826, and incubated for an additional 10 minutes at room temperature. Following this incubation, fluid was aspirated from the tubes and 1.0 ml Wash Buffer was added to each tube. The tubes were then briefly vortexed before being returned to the magnetic separation rack for a 5 minute incubation at room temperature. After this incubation, fluid was again aspirated from the tubes, 1.0 ml Wash Buffer was added to each tube, and the tubes were briefly vortexed prior to a second 5 minute incubation in the magnetic separation rack at room temperature. Fluid was aspirated from the tubes a third time before adding 75 µl Amplification Reagent and 100 µl Oil Reagent, in that order, to each tube and briefly vortexing. The Amplification Reagent in this experiment contained 30 µl each of a primer and a promoter-primer from stock solutions containing these reagents at concentrations of 15 pmol/µl water. The promoter-primer reagent was comprised of a 3' end sense template-specific base sequence of SEQ ID NO:29 and a 5' end promoter base sequence of SEQ ID NO:41, and the primer reagent had an antisense template-specific base sequence of SEQ ID NO:21.

At this point, the tubes were incubated for 10 minutes at 60° C. in a water bath (Precision Scientific; Cat. No. 51221035) to denature the transcript. Afterwards, the samples were transferred to a circulating water bath (Lauda Dr. R. Wobser; Model No. M20-S) and incubated for 5 minutes at 42° C. before adding 25 µl of reconstituted Enzyme Reagent to each tube and mixing by hand. Following a 60 minute incubation at 42° C. in the circulating water bath, 100 µl probe mix (obtained from a stock solution containing 2 ml 2× Hybridization Reagent and 20 µl hybridization assay probe at a concentration of 100 fmol/µl 1×Hybridization Reagent) was added to each tube, and the tubes were vortexed before being incubated for 20 minutes in the 60° C. water bath. Following this incubation, 300 µl Selection Reagent was added to each tube, and the tubes were vortexed before being incubated in the 60° C. water bath for 10 minutes to hydrolyze acridinium ester labels associated with unhybridized probe. Samples were cooled on ice for 1 minute prior to being analyzed in a LEADER® 450hc luminometer equipped with automatic injection of the Detection Regents for detecting signal from annealed hybridization assay probe. A sample set with an average RLU value greater than 10-fold the. average RLU value for the negative control (0 transcript copies) indicated transcript amplification, and a sample set with an average RLU value less than 10-fold the average RLU for the negative control would have indicated no transcript amplification. The results are set forth in Table 13 below.

TABLE 13

Signal from Samples Containing Different Initial Concentrations of M. pneumoniae Target RNA Using a Target Capture System

| Transcript Concentration | Total RLU | Average RLU | Average Net RLU |
|---|---|---|---|
| Negative Control | 3,270 7,117 4,467 8,020 10,829 | 6,741 | 0 |
| 200 Copies | 1,721,015 1,258,972 827,025 2,745,802 2,773,824, | 1,865,328 | 1,858,587 |

TABLE 13-continued

Signal from Samples Containing Different Initial Concentrations
of *M. pneumoniae* Target RNA Using a Target Capture System

| Transcript Concentration | Total RLU | Average RLU | Average Net RLU |
|---|---|---|---|
| 2,000 Copies | 2,829,280 | 2,545,003 | 2,538,262 |
| | 2,927,871 | | |
| | 1,616,892 | | |
| | 2,729,446 | | |
| | 2,621,525 | | |

The results of this experiment demonstrate that the target capture system employed, including the hybridization assay probes, capture probes, promoter-primers and primers, is very sensitive in detecting the presence of the targeted transcript.

Example 5

Amplification and Specific Detection of *M. pneumoniae* Nucleic Acid Using a Target Capture System As with Example 4, this example illustrates the immobilization and amplification of a target sequence of *M. pneumoniae* nucleic acid, followed by detection of amplified rRNA using a hybridization assay probe specific for *M. pneumoniae*-derived nucleic acid. Unlike Example 4, however, this experiment included total RNA in the test sample from, in addition to *M. pneumoniae*, non-target organisms which included *M. fermentans, M. gallisepticum, M. genitalium, M. hominis, M. orale, Streptococcus pneumoniae, Ureaplasma urealyticum, Chlamydia pneumoniae, Chlamydia psittaci* and *Chlamydia trachomatis*. This group of non-target organisms represents organisms which are closely related to *M. pneumoniae*, as well as common throat culture organisms. The hybridization assay probe of this experiment was identical to the probe of Example 4 and was used to detect the product of a transcription-mediated amplification.

Stock solutions of RNA for each organism were prepared in Transport Medium so that the final concentration of RNA in each stock solution, except for *C. pneumoniae*, was the equivalent of approximately 1000 cells/µl. The final concentration of RNA in the *C. pneumoniae* stock solution was the equivalent of approximately 100 cells/µl. Negative control and positive control stock solutions were also prepared. Six 12×75 mm polypropylene reaction tubes (Gen-Probe Incorporated; Cat. No. 2440) were then set up for each non-target organism, with each member of a duplicate set of reaction tubes receiving the equivalent of 100, 1,000 or 10,000 cells (all non-target organisms except *C. pneumoniae*) or 10, 100 or 1,000 cells (*C. pneumoniae*). For *M. pneumoniae*, six of the same reaction tubes were set up, each member of a duplicate set of tubes receiving the equivalent of 0. 1, 1 or 10 cells. In all other respects, the reagents, concentrations, conditions, times and instruments were the same as those detailed for the target capture assay set forth in Example 4. Samples were analyzed in a LEADER® 450hc luminometer equipped with automatic injection of the Detection Regents for detecting signal from annealed hybridization assay probe. A sample set with an average RLU value greater than 10-fold the average RLU value for the negative control (no RNA) indicated amplification, and a sample set with an average RLU value less than 10-fold the average RLU for the negative control indicated no amplification. The results are set forth in Table 14 below.

TABLE 14

Signal from Samples Containing Different Initial
Concentrations of *M. pneumoniae* Target RNA and
Non-Target RNA Using a Target Capture System

| Organisms | Concentration of RNA | RLU | Average RLU | Average Net RLU |
|---|---|---|---|---|
| Negative Control | 0 | 7,187 | 6,536 | 0 |
| | 0 | 7,600 | | |
| | 0 | 4,820 | | |
| *M. pneumoniae* | 50 fg | 1,170,920 | 1,907,646 | 1,901,110 |
| | | 2,644,372 | | |
| | 5 fg | 2,038,296 | 2,068,150 | 2,061,614 |
| | | 2,098,005 | | |
| | 0.5 fg | 953,812 | 1,133,114 | 1,126,578 |
| | | 1,312,417 | | |
| *M. fermentans* | 50 pg | 1,905 | 2108 | −4,428 |
| | | 2,311 | | |
| | 5 pg | 2,205 | 3,572 | −2,964 |
| | | 4,939 | | |
| | 500 fg | 2,277 | 3,574 | −2,962 |
| | | 4,871 | | |
| *M. gallisepticum* | 50 pg | 3,631 | 5,290 | −1,246 |
| | | 6,950 | | |
| | 5 pg | 4,577 | 4,598 | −1,937 |
| | | 4,620 | | |
| | 500 fg | 2,109 | 2,480 | −4,055 |
| | | 2,852 | | |
| *M. genitallium* | 50 pg | 1,568 | 4,244 | −2,292 |
| | | 6,919 | | |
| | 5 pg | 5,774 | 8,320 | 1,784 |
| | | 10,865 | | |
| | 500 fg | 6,111 | 5,148 | −1,388 |
| | | 4,185 | | |
| *M. hominis* | 50 pg | 4,449 | 5,316 | −1,219 |
| | | 6,184 | | |
| | 5 pg | 1,862 | 2,204 | −4,332 |
| | | 2,545 | | |
| | 500 fg | 1,668 | 1,590 | −4,946 |
| | | 1,512 | | |
| *M. orale* | 50 pg | 6,483 | 9,553 | 3,017 |
| | | 12,623 | | |
| | 5 pg | 1,739 | 2,994 | −3,542 |
| | | 4,249 | | |
| | 500 fg | 6,410 | 4,036 | −2,500 |
| | | 1,661 | | |
| *S. pneumoniae* | 50 pg | 7,162 | 7,211 | 675 |
| | | 7,260 | | |
| | 5 pg | 6,147 | 5,656 | −880 |
| | | 5,165 | | |
| | 500 fg | 6,651 | 5,922 | −614 |
| | | 5,192 | | |
| *U. urealyticum* | 50 pg | 4,366 | 3,894 | −2,642 |
| | | 3,421 | | |
| | 5 pg | 2,164 | 3,518 | −3,018 |
| | | 4,872 | | |
| | 500 fg | 8,685 | 7,840 | 1,304 |
| | | 6,994 | | |
| *C. pneumoniae* | 5 pg | 9,219 | 7,891 | 1,355 |
| | | 6,563 | | |
| | 500 fg | 4,384 | 5,356 | −1,180 |
| | | 6,328 | | |
| | 50 fg | 1,979 | 2,373 | −4,163 |
| | | 2,767 | | |
| *C. psittaci* | 50 pg | 4,789 | 4,377 | −2,159 |
| | | 3,965 | | |
| | 5 pg | 8,363 | 9,200 | 2,664 |
| | | 10,038 | | |
| | 500 fg | 7,360 | 7,365 | 829 |
| | | 7,370 | | |

TABLE 14-continued

Signal from Samples Containing Different Initial Concentrations of *M. pneumoniae* Target RNA and Non-Target RNA Using a Target Capture System

| Organisms | Concentration of RNA | RLU | Average RLU | Average Net RLU |
|---|---|---|---|---|
| C. trachomatis | 50 pg | 6,318 | 5,289 | −1,247 |
|  |  | 4,260 |  |  |
|  | 5 pg | 1,960 | 2,575 | −3,961 |
|  |  | 3,190 |  |  |
|  | 500 fg | 6,742 | 5,630 | −905 |
|  |  | 4,519 |  |  |

The results of this experiment demonstrate that the target capture system employed, including the hybridization assay probes, capture probes, promoter-primers and primers, is specific for *M. pneumoniae* in the presence of closely related, non-target organisms, as well as common throat organisms.

Example 6

Sensitivity of *M. pneumoniae* Target Capture Assay in the Presence of RNA from Non-Target Organisms This example illustrates the effectiveness of the target capture assay described in Example 4 above for detecting *M. pneumoniae* target nucleic acid in the presence of non-target nucleic acid from closely related organisms and common throat pathogens. Inthis experiment, each sample tested contained the RNA equivalent of 1 cell of *M. pneumoniae* and the RNA equivalent of one of the following: 100 cells of *C. pneumoniae*, 1,000 cells of *C. psittaci* or *C. trachomatis*, and 10,000 cells of *M. fermentans, M. gallisepticum, M. genitalium, M. hominis, M. orale, S. pneumoniae* or *U. urealyticum*. Negative controls and positive controls containing no added nucleic acid and the RNA equivalent of 1 cell of *M. pneumoniae*, respectively, were also included in this experiment. The basic protocol of Example 4 was followed for this experiment, except that 100 µl hybridization assay probe at a concentration of 100 fmol/100 µl was used instead of 20 µl hybridization assay probe at a concentration of 100 fmol/µl, and 200 µl Oil Reagent was used instead of 100 µl Oil Reagent. The results of this experiment are set forth in Table 15 below.

TABLE 15

Signal from Samples Containing *M. pneumoniae* Target RNA and Non-Target RNA Using a Target Capture System

| Sample | RLU | Average RLU | Average Net RLU |
|---|---|---|---|
| Negative Control | 18,056 | 9,719 | 0 |
|  | 9,062 |  |  |
|  | 8,290 |  |  |
|  | 8,415 |  |  |
|  | 4,772 |  |  |
| Positive Control | 4,923,785 | 10,446,107 | 10,436,388 |
|  | 11,475,165 |  |  |
|  | 12,698,836 |  |  |
|  | 11,074,638 |  |  |
|  | 12,058,112 |  |  |
| M. fermentans | 13,015,384 | 10,723,356 | 10,713,637 |
|  | 12,023,612 |  |  |
|  | 9,959,722 |  |  |

TABLE 15-continued

Signal from Samples Containing *M. pneumoniae* Target RNA and Non-Target RNA Using a Target Capture System

| Sample | RLU | Average RLU | Average Net RLU |
|---|---|---|---|
|  | 12,568,266 |  |  |
|  | 6,049,798 |  |  |
| M. gallisepticum | 10,205,671 | 11,521,574 | 11,511,855 |
|  | 12,054,638 |  |  |
|  | 11,738,520 |  |  |
|  | 11,991,393 |  |  |
|  | 11,617,649 |  |  |
| M. genitalium | 111,631 | 105,476 | 95,757 |
|  | 92,063 |  |  |
|  | 93,271 |  |  |
|  | 127,013 |  |  |
|  | 103,401 |  |  |
| M. hominis | 11,405,206 | 10,859,583 | 10,849,846 |
|  | 11,788,559 |  |  |
|  | 7,912,821 |  |  |
|  | 11,390,741 |  |  |
|  | 11,800,590 |  |  |
| M. orale | 9,831,637 | 9,957,989 | 9,948,270 |
|  | 11,790,690 |  |  |
|  | 4,519,802 |  |  |
|  | 12,128,623 |  |  |
|  | 11,519,194 |  |  |
| S. pneumoniae | 11,443,711 | 11,690,756 | 11,681,037 |
|  | 11,226,151 |  |  |
|  | 12,288,957 |  |  |
|  | 12,182,387 |  |  |
|  | 11,312,575 |  |  |
| U. urealyticum | 11,797,208 | 10,521,908 | 10,512,189 |
|  | 12,702,841 |  |  |
|  | 11,606,749 |  |  |
|  | 5,980,833 |  |  |
| C. pneumoniae | 7,518,897 | 9,264,619 | 9,254,900 |
|  | 12,658,402 |  |  |
|  | 12,468,268 |  |  |
|  | 12,481,368 |  |  |
|  | 1,196,162 |  |  |
| C. psittaci | 11,971,074 | 8,113,914 | 8,104,195 |
|  | 2,896,343 |  |  |
|  | 11,927,341 |  |  |
|  | 12,953,801 |  |  |
|  | 821,011 |  |  |
| C. trachomatis | 9,367,627 | 7,266,740 | 7,257,021 |
|  | 1,058,578 |  |  |
|  | 2,530,696 |  |  |
|  | 12,591,743 |  |  |
|  | 10,785,055 |  |  |

The results of this experiment suggest no significant interference by RNA from from any organism other than *M. genitalium*, the most closely related organism to *M. pneumoniae*.

Example 7

Sensitivity of *M. pneumoniae* Target Capture Assay at Varying Concentrations of RNA from *M. pneumoniae* and *M. genitalium*

This example further examines the effectiveness of the target capture assay described in Example 4 above for detecting the presence of *M. pneumoniae* target nucleic acid in the presence of non-target nucleic acid from *M. genitalium*. For this experiment, each sample tested contained the RNA equivalent of 1, 10 or 100 cells of *M. pneumoniae* and, for each concentration of *M. pneumoniae* RNA tested, samples contained the RNA equivalent of 100, 1,000 or 10,000 cells of *M. genitalium*. Each combination was tested in sets of five. Negative controls containing no added nucleic acid were also included. The protocol of Example 4 was generally followed, except for the differences noted in Example 6 above. The results of this experiment are set forth in Table 16 below.

TABLE 16

Signal from Samples Containing Different Combinations of M. pneumoniae Target RNA and Non-Target RNA Using a Target Capture System

| M. pneumoniae (Cell Number) | M. genitalium (Cell Number) | RLU | Average RLU | Average Net RLU |
|---|---|---|---|---|
| 0 | 0 | 3,706 | 4477 | 0 |
|  |  | 5,994 |  |  |
|  |  | 3,766 |  |  |
|  |  | 5,245 |  |  |
|  |  | 3,675 |  |  |
| 1 | 10,000 | 76,576 | 70,760 | 66,283 |
|  |  | 94,086 |  |  |
|  |  | 73,156 |  |  |
|  |  | 54,763 |  |  |
|  |  | 55,221 |  |  |
| 1 | 1,000 | 214,808 | 265,738 | 261,261 |
|  |  | 242,365 |  |  |
|  |  | 348,265 |  |  |
|  |  | 232,113 |  |  |
|  |  | 291,137 |  |  |
| 1 | 100 | 1,202,864 | 983,771 | 979,294 |
|  |  | 950,784 |  |  |
|  |  | 778,668 |  |  |
|  |  | 1,168,746 |  |  |
|  |  | 817,792 |  |  |
| 10 | 10,000 | 307,934 | 364,826 | 360,349 |
|  |  | 410,299 |  |  |
|  |  | 338,253 |  |  |
|  |  | 278,428 |  |  |
|  |  | 489,217 |  |  |
| 10 | 1,000 | 1,006,075 | 1,054,078 | 1,049,601 |
|  |  | 906,978 |  |  |
|  |  | 1,483,268 |  |  |
|  |  | 917,174 |  |  |
|  |  | 956,897 |  |  |
| 10 | 100 | 2,469,284 | 2,477,553 | 2,473,076 |
|  |  | 2,178,209 |  |  |
|  |  | 2,887,385 |  |  |
|  |  | 2,168,899 |  |  |
|  |  | 2,683,987 |  |  |
| 100 | 10,000 | 2,564,911 | 2,080,209 | 2,075,732 |
|  |  | 2,029,568 |  |  |
|  |  | 1,897,549 |  |  |
|  |  | 1,887,921 |  |  |
|  |  | 2,021,097 |  |  |
| 100 | 1,000 | 4,125,926 | 3,980,633 | 3,976,156 |
|  |  | 3,835,937 |  |  |
|  |  | 4,602,968 |  |  |
|  |  | 3,442,157 |  |  |
|  |  | 3,896,175 |  |  |
| 100 | 100 | 3,613,805 | 4,657,212 | 4,652,735 |
|  |  | 4,864,564 |  |  |
|  |  | 4,724,593 |  |  |
|  |  | 5,157,550 |  |  |
|  |  | 4,925,546 |  |  |

The results of this experiment indicate that at an RNA equivalent concentration of 100 M. pneumoniae cells, the presence of M. genitalium RNA up to an RNA equivalent concentration of least 10,000 cells does not affect the sensitivity of the target capture assay of Example 4 above in detecting the presence of M. pneumoniae target nucleic acid. Test samples positive for M. pneumoniae would be expected to have at least 100 M. pneumoniae cells.

Example 8

Amplification and Detection of *Mycoplasma genitalium*-Derived Nucleic Acid

This example demonstrates the ability of four different hybridization assay probes to differentiate between M. genitalium and M. pneumoniae amplicon at different temperatures. In this example, three hybridization assay probes having the base sequence of SEQ ID NO:5 (Probes 1–3) and one hybridization assay probe having the base sequence of SEQ ID NO:9 (Probe 4) were synthesized to include a non-nucleotide linker, as described above. Reading 5' to 3', the non-nucleotide linker was included in each probe sequence as follows: (i) between nucleotides 13 and 14 for Probe 1; (ii) between nucleotides 14 and 15 for Probe 2; (iii) between nucleotides 16 and 17 for Probe 3; and (iv) between nucleotides 9 and 10 for Probe 4. The hybridization assay probes were of the same sense as the M. genitalium target rRNA and were used to detect the product of a transcription-mediated amplification.

Transcripts were generated from 16S rRNA sequences obtained from M. genitalium (ATCC Accession No. 49123) and M. pneumoniae (ATCC Accession No. 15531) using a primer set which included a promoter-primer having a 5' end promoter base sequence of SEQ ID NO:41 and a 3' end primer having a sense template-specific base sequence of SEQ ID NO:29 and a primer having an antisense template-specific base sequence of SEQ ID NO:21. The primer sequences of the primer set bound to nucleic acid derived from both M. genitalium and M. pneumoniae and were extended under the conditions described below.

The reconstituted amplification reagent used in this experiment contained 44.1 mM HEPES, 0.003% (v/v) Phenol Red, 0.5%, 9.4 mM rATP, 1.8 mM rCTP, 11.8 mM rGTP, 1.8 mM rUTP, 0.47 mM each of dATP, dCTP, dGTP and dTTP, 2.82% (w/v) trehalose, 33.0 mM KCl, 30.6 mM $MgCl_2$, 0.30% (v/v) ethyl alcohol, absolute, 0.1% (w/v) methyl paraben, 0.02% (w/v) propyl paraben, and 4 M NaOH to pH 7.7. The primer and promoter-primer were provided to amplification reagent so that the final concentration of each of these reagents was approximately 0.2 pmol/μl.

The amplification and hybridization reactions of this example were carried out in three sets of six integral test tube units (TTUs), each unit being comprised of ten 12×75 mm polypropylene test tubes. The TTUs of each set received the same amount of target nucleic acid and probe, and each set included a total of five replicates for each target nucleic acid/probe combination tested. The target nucleic acid/probe combinations for each set of six TTUs are provided in Table 17 below, with only the temperature of the hybridization reaction varying between the three sets of TTUs.

TABLE 17

Target Nucleic Acid/Probe Combinations Tested

| Tube Number | Target Nucleic Acid | Probe |
|---|---|---|
| 1–5 | Negative Control | Probe 1 |
| 6–10 | M. genitalium | Probe 1 |
| 11–15 | M. pneumoniae | Probe 1 |
| 16–20 | Negative Control | Probe 2 |
| 21–25 | M. genitalium | Probe 2 |
| 26–30 | M. pneumoniae | Probe 2 |
| 31–35 | Negative Control | Probe 3 |
| 36–40 | M. genitalium | Probe 3 |

TABLE 17-continued

Target Nucleic Acid/Probe Combinations Tested

| Tube Number | Target Nucleic Acid | Probe |
|---|---|---|
| 41–45 | M. pneumoniae | Probe 3 |
| 46–50 | Negative Control | Probe 4 |
| 51–55 | M. genitalium | Probe 4 |
| 56–60 | M. pneumoniae | Probe 4 |

For amplification of the target nucleic acid, three stock solution tubes were prepared, each tube containing 4.8 ml of reconstituted amplification reagent and separately containing: (i) 32 µl Wash Buffer in Tube 1 (negative control); (ii) 64.3 µl Wash Buffer containing M. pneumoniae rRNA to bring final concentration of M. pneumoniae to 6.7 fg/µl in Tube 2; and (iii) 32 µl Wash Buffer containing M. genitalium rRNA to bring final concentration of M. genitalium to 3.47 fg/µl in Tube 3. From these stock solution tubes, 75 µl amplification reagent was provided to each set of TTUs in the manner indicated in Table 17. Each tube of the TTUs then received 200 µl Oil Reagent before being vortexed.

To facilitate binding of the promoter-primer to the target nucleic acids prior to amplification, the reaction tubes were incubated at 60° C. in a circulating water bath (Precision Scientific; Cat. No. 51221035) for 5 minutes. The TTUs were then transferred to another circulating water bath (Precision Scientific; Cat. No. 51221035) and incubated for another 5 minutes at 42° C. to denature target nucleic acid before adding 25 µl of reconstituted enzyme reagent to each tube. The reconstituted enzyme reagent in this experiment contained 58 mM HEPES, 50 mM NALC, 1.0 mM EDTA, 10% (v/v) TRITON X-100, 3% (w/v) trehalose, 120 mM KCl, 20% (v/v) glycerol, 360 U/µl MMLV reverse transcriptase, 80 U/µl T7 RNA polymerase, and 4M NaOH to pH 7.0. (A "unit" of activity for the enzymes is defined above under "Enzyme Reagent" definition in the "Reagents" section.) After adding the reconstituted enzyme reagent to the tubes, the TTUs were covered and shaken by hand and before amplification was carried out for 60 minutes in the 42° C. circulating water bath.

Following amplification, the TTUs were removed from the water bath and 100 µL of probe-containing hybridization reagent was added to each tube in the manner indicated in Table 17 above. Probe-containing 2× Hybridization Reagent was prepared in four 15 ml high density polyethylene tubes, each tube containing 12.0 ml 2× Hybridization Reagent and separately containing one of the following: (i) 3.0 µl Probe 1 from a stock solution containing 4.0 pmol of Probe/µl; (ii) 5.0 µl Probe 2 from a stock solution containing 2.38 pmol of Probe 2/µl; (iii) 4.5 µl Probe 3 from a stock solution containing 2.66 pmol of Probe 3/µl; and (iv) 5.1 µl Probe 4 from a stock solution containing 2.34 pmol of Probe 4/µl. The TTUs were then vortexed before being incubated for 20 minutes in circulating water baths (Precision Scientific; Cat. No. 51221035) at temperatures of 60° C. ("Set 1"), 62° C. ("Set 2"), and 64° C. ("Set 3"). After incubating, the TTUs were removed from the water bath and each tube received 250 µl of a selection reagent containing 150 mM sodium borate, 1% (v/v) TRITON X-100, and 4M NaOH to pH 8.5. The TTUs were again vortexed before being incubated in the water baths for another 10 minutes at the same temperatures to hydroyze acridinium ester labels associated with unhybridized probe. The TTUs were then cooled for five minutes in an ambient water bath before being analyzed in a LEADER® HC+luminometer (Gen-Probe Incorporated) equipped with automatic injection of the APTIMA® Auto Detection Reagents I and II (Gen-Probe Incorporated; Catalog No. 1048). The results are set forth in Tables 18–21 below.

TABLE 18

Signal from Samples Containing Target RNA Derived from
M. genitalium and Non-Target RNA Derived from
M. pneumoniae at 60° C. Hybridization Temperature

| Sample Tubes (Set 1) | Target Nucleic Acid | Probe | Average RLU | % CV |
|---|---|---|---|---|
| 1–5 | Negative Control | 1 | 2,497 | 8.7 |
| 6–10 | M. genitalium | 1 | 5,319,042 | 2.2 |
| 11–15 | M. pneumoniae | 1 | 664,105 | 39.2 |
| 16–20 | Negative Control | 2 | 2,103 | 12.3 |
| 21–25 | M. genitalium | 2 | 6,431,167 | 2.2 |
| 26–30 | M. pneumoniae | 2 | 629,704 | 42.1 |
| 31–35 | Negative Control | 3 | 1,570 | 17.7 |
| 36–40 | M. genitalium | 3 | 4,900,267 | 2.7 |
| 41–45 | M. pneumoniae | 3 | 14,019 | 69.5 |
| 46–50 | Negative Control | 4 | 3,843 | 5.7 |
| 51–55 | M. genitalium | 4 | 9,277,431 | 1.0 |
| 56–60 | M. pneumoniae | 4 | 94,182 | 26.5 |

TABLE 19

Signal from Samples Containing Target RNA Derived from
M. genitalium and Non-Target RNA Derived from M. Pneumoniae
at 62° C. Hybridization Temperature

| Sample Tubes (Set 2) | Target Nucleic Acid | Probe | Average RLU | % CV |
|---|---|---|---|---|
| 61–65 | Negative Control | 1 | 2,677 | 6.7 |
| 66–70 | M. genitalium | 1 | 4,474,752 | 1.8 |
| 71–75 | M. pneumoniae | 1 | 72,830 | 44.4 |
| 76–80 | Negative Control | 2 | 2,230 | 10.8 |
| 81–85 | M. genitalium | 2 | 5,272,019 | 1.5 |
| 86–90 | M. pneumoniae | 2 | 81,854 | 15.6 |
| 91–95 | Negative Control | 3 | 1,639 | 23.1 |
| 96–100 | M. genitalium | 3 | 4,012,082 | 2.5 |
| 101–105 | M. pneumoniae | 3 | 5,640 | 14.9 |
| 106–110 | Negative Control | 4 | 3,518 | 4.5 |
| 111–115 | M. genitalium | 4 | 7,936,926 | 4.1 |
| 116–120 | M. pneumoniae | 4 | 7,260 | 9.1 |

TABLE 20

Signal from Samples Containing Target RNA Derived from
M. genitalium and Non-Target RNA Derived from M. Pneumoniae
at 64° C. Hybridization Temperature

| Sample Tubes (Set 3) | Target Nucleic Acid | Probe | Average RLU | % CV |
|---|---|---|---|---|
| 121–125 | Negative Control | 1 | 2,730 | 6.1 |
| 126–130 | M. genitalium | 1 | 3,959,893 | 1.8 |
| 131–135 | M. pneumoniae | 1 | 12,936 | 20.8 |
| 136–140 | Negative Control | 2 | 2,098 | 26.7 |
| 141–145 | M. genitalium | 2 | 4,543,193 | 10.4 |
| 146–150 | M. pneumoniae | 2 | 13,537 | 29.4 |
| 151–155 | Negative Control | 3 | 1,474 | 32.9 |
| 156–160 | M. genitalium | 3 | 3,657,316 | 2.9 |
| 161–165 | M. pneumoniae | 3 | 2,865 | 23.6 |
| 166–170 | Negative Control | 4 | 3,217 | 2.9 |
| 171–175 | M. genitalium | 4 | 7,495,610 | 1.9 |
| 176–180 | M. pneumoniae | 4 | 5,180 | 22.8 |

TABLE 21

Signal Ratios for *M. genitalium* Probes Tested Under Different Hybridization Conditions

| Probe | Hybridization Temperature (° C.) | *M. genitalium*/ Negative Control Ratio | *M. genitalium*/ *M. pneumoniae* Ratio | *M. pneumoniae*/ Negative Control Ratio |
|---|---|---|---|---|
| 1 | 60 | 2,129.83 | 8.01 | 265.92 |
| 2 | 60 | 3,057.80 | 10.21 | 299.40 |
| 3 | 60 | 3,120.79 | 349.55 | 8.93 |
| 4 | 60 | 2,414.36 | 98.51 | 24.51 |
| 1 | 62 | 1,671.80 | 61.44 | 27.21 |
| 2 | 62 | 2,364.35 | 64.41 | 36.71 |
| 3 | 62 | 2,448.48 | 711.43 | 3.44 |
| 4 | 62 | 2,256.22 | 1,093.21 | 2.06 |
| 1 | 64 | 1,450.30 | 306.11 | 4.74 |
| 2 | 64 | 2,165.69 | 335.62 | 6.45 |
| 3 | 64 | 2,481.22 | 1,276.37 | 1.94 |
| 4 | 64 | 2,330.14 | 1,447.14 | 1.61 |

The results of this experiment demonstrate that Probes 3 and 4 were superior in distinguishing between nucleic acid derived from *M. genitalium* and *M. pneumoniae*. Probe 3, in particular, exhibited excellent ratios at each of the hybridization temperatures tested.

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

---

What we claim is:

1. A hybridization assay probe for use in determining the presence of *Mycoplasma pneumoniae* in a sample, said probe comprising a target binding region, wherein the base sequence of said target binding region consists of a base sequence selected from the group consisting of SEQ ID NO:1, SEQ ID NO:2, SEQ ID NO:3 and SEQ ID NO:4, and a detectable label joined to a non-nucleotide linker positioned between nucleotides 14 and 15 or 16 and 17 of SEQ ID NO:1 or SEQ ID NO:2 or joined to a non-nucleotide linker positioned between nucleotides 16 and 17 or 18 and 19 of SEQ ID NO:3 or SEQ ID NO:4,
   wherein said target binding region is capable of forming a detectable hybrid with nucleic acid derived from *Mycoplasma pneumoniae* under stringent hybridization conditions,
   wherein said probe is not capable of forming a detectable hybrid with nucleic acid derived from *Mycoplasma genitalium* under said conditions, and
   wherein said probe does not comprise another base sequence region overlapping with or in addition to said target binding region which is capable of forming a stable hybrid with nucleic acid derived from *Mycoplasma pneumoniae* under said conditions.

2. The probe of claim 1, wherein the base sequence of said probe consists of the base sequence of SEQ ID NO:1, SEQ ID NO:2, SEQ ID NO:3 or SEQ ID NO:4.

3. The probe of claim 1, wherein said probe comprises at least one base sequence region in addition to said target binding region.

4. The probe of claim 1, wherein said probe comprises a pair of base sequence regions which hybridize to each other when said probe is not hybridized to nucleic acid derived from *Mycoplasma pneumoniae* under said conditions.

5. The probe of claim 1, wherein said target binding region includes at least one ribonucleotide modified to include a 2'-O-methyl substitution to the ribofuranosyl moiety.

6. The probe of claim 1, wherein a pseudo peptide backbone joins at least a portion of the bases of said target binding region.

7. The probe of claim 1, wherein said detectable label is a chemiluminescent molecule.

8. The probe of claim 1, wherein said conditions comprise 50 mM succinic acid, 1% (w/v) LLS, 7.5 mM aldrithiol-2, 0.6 M LiCl, 50 mM LiOH, 10 mM EDTA, 1.5% (v/v) ethyl alcohol (absolute), pH to 4.7, and a temperature of about 60° C.

9. A composition comprising said probe of claim 1 hybridized to nucleic acid derived from *Mycoplasma pneumoniae* under said conditions.

10. A kit comprising:
    said probe of claim 1; and
    a first oligonucleotide, wherein the base sequence of said first oligonucleotide consists of a base sequence selected from the group consisting of SEQ ID NO:29, SEQ ID NO:30, SEQ ID NO:31 and SEQ ID NO:32, and, optionally, a 5' sequence which is recognized by an RNA polymerase or which enhances initiation or elongation by an RNA polymerase.

11. The kit of claim 10, wherein the base sequence of said first oligonucleotide includes the 5' sequence which is recognized by an RNA polymerase or which enhances initiation or elongation by an RNA polymerase.

12. The probe of claim 10, wherein said detectable label is a chemiluminescent molecule.

13. The kit of claim 10 further comprising a second oligonucleotide consisting of a base sequence selected from the group consisting of SEQ ID NO:21, SEQ ID NO:22, SEQ ID NO:23 and SEQ ID NO:24 and, optionally, a 5' sequence which is recognized by an RNA polymerase or which enhances initiation or elongation by an RNA polymerase.

14. The kit of claim 13, wherein the base sequence of said first or second oligonucleotide includes the 5' sequence which is recognized by an RNA polymerase or which enhances initiation or elongation by an RNA polymerase.

15. The probe of claim 13, wherein said detectable label is a chemiluminescent molecule.

16. The kit of claim 13 further comprising a third oligonucleotide, said third oligonucleotide comprising a target binding region, wherein the base sequence of said target binding region consists of a base sequence selected from the group consisting of SEQ ID NO:13, SEQ ID NO:14, SEQ ID NO:15 and SEQ ID NO:16, wherein said target binding region is capable of forming a stable hybrid with nucleic acid derived from *Mycoplasma pneumoniae* under hybridization conditions, and wherein said third oligonucleotide does not comprise another base sequence region overlapping with or in addition to said target binding region which is capable of forming a stable hybrid with nucleic acid derived from *Mycoplasma pneumoniae* under said conditions.

17. The kit of claim 16, wherein the base sequence of said first or second oligonucleotide includes the 5' sequence which is recognized by an RNA polymerase or which enhances initiation or elongation by an RNA polymerase.

18. The probe of claim 16, wherein said detectable label is a chemiluminescent molecule.

19. A kit comprising:
    said probe of claim 1; and
    an oligonucleotide comprising a target binding region, wherein the base sequence of said target binding region consists of a base sequence selected from the group consisting of SEQ ID NO:13, SEQ ID NO:14, SEQ ID NO:15 and SEQ ID NO:16, wherein said target binding region is capable of forming a stable hybrid with nucleic acid derived from *Mycoplasma pneumoniae* under hybridization conditions, and wherein said oligonucleotide does not comprise another base sequence region overlapping with or in addition to said target binding region which is capable of forming a stable hybrid with nucleic acid derived from *Mycoplasma pneumoniae* under said conditions.

20. The probe of claim 19, wherein said detectable label is a chemiluminescent molecule.

* * * * *